US007885833B2

(12) United States Patent
Giles

(10) Patent No.: US 7,885,833 B2
(45) Date of Patent: Feb. 8, 2011

(54) SYSTEM AND METHOD OF TREATING TEMPRO MANDIBULAR DISORDERS UTILIZING A PROTOCOL OF EXAMINATIONS, DIAGNOSTICS, PROCEDURES AND TREATMENTS TO GENERATE LETTERS, REPORTS AND CODED INSURANCE CLAIM FORMS TO MAXIMIZE BENEFIT PAYMENTS

(75) Inventor: Grant E. Giles, Midland, TX (US)

(73) Assignee: Group Technologies, Inc., Cypress, TX (US)

( * ) Notice: Subject to any disclaimer, the term of this patent is extended or adjusted under 35 U.S.C. 154(b) by 735 days.

(21) Appl. No.: 11/899,208

(22) Filed: Sep. 5, 2007

(65) Prior Publication Data

US 2009/0063192 A1    Mar. 5, 2009

(51) Int. Cl.
*G06Q 40/00* (2006.01)
(52) U.S. Cl. .............................. 705/4; 705/2; 715/226; 600/300; 433/24
(58) Field of Classification Search .................... 705/2; 715/226; 600/300; 433/24
See application file for complete search history.

(56) References Cited

U.S. PATENT DOCUMENTS

| | | | | |
|---|---|---|---|---|
| 5,915,241 A | * | 6/1999 | Giannini | 705/2 |
| 6,688,885 B1 | * | 2/2004 | Sachdeva et al. | 433/24 |
| 6,954,730 B2 | * | 10/2005 | Lau et al. | 705/2 |
| 7,409,632 B1 | * | 8/2008 | DiRienzo | 715/226 |
| 2005/0148830 A1 | * | 7/2005 | Arnett | 600/300 |
| 2006/0089862 A1 | * | 4/2006 | Anandarao et al. | 705/4 |

* cited by examiner

*Primary Examiner*—Dilek B Cobanoglu
(74) *Attorney, Agent, or Firm*—Christopher L. Makay

(57) ABSTRACT

An interactive system and a method for diagnosing, evaluating and treating the condition of Temporomandibular Disorder, where through a series of steps, consultations, procedures and protocols associated with individual appointments, information is gathered and entered into a database by a user through a personal computing device, which is added to or updated as treatment progresses in future appointments. The information gained during the appointments is used to generate printed or electronic reports, letters and insurance claim forms supporting the services rendered, reduce the errors involved in manual insurance claim form coding, supply consistent and proven successful treatment codes to insure payment, and which seek reimbursement from medical insurance coverage by the dentist as opposed to dental insurance coverage in order to maximize the benefits received and allow the patient to avail themselves of the generally higher coverage limits and lower deductibles associated with medical insurance.

16 Claims, 71 Drawing Sheets

PATIENT INFO

*Date: 8/8/2007    Patient #: 1*

*Required fields

*Last Name: [redacted]    *First Name: suzy    *M.I.

*D.O.B.:    Sex:    SS#:    Dr. Lic. #:

*Street Address:

*City:    *State:    *Zip Code:

Home Phone:    Work Phone:    *Patient Status:

*Employed: ☐  Part-Time Student: ☐  Full-Time Student: ☐  *Patient Signature Date:

Person Responsible for Account

Person Responsible:

Last Name:    First Name:    M.I.

D.O.B.:    Sex:    SS#:    Dr. Lic. #:

Street Address:

City:    State:    Zip Code:

Home Phone:    Work Phone:

Employed by:    How Long?

Employer's Address:

City:    State:    Zip Code:

Employer's Phone:

Fig. 6B    197

225 — Health Questionnaire - price, suzy

| Section 1 | Patient's medical & dental history. (Part 1) |
| Section 1b | Patient's medical & dental history. (Part 2) |
| Section 2 | Patient's craniofacial pain symptoms. (Part 1) |
| Section 2b | Patient's Cranio Facial Pain Symptoms. (Part 2) |
| Section 3 | Patient's craniofacial symptoms, Postural, lifestyle, TMJ, trauma relationship problems. (Part 3) |
| Section 4 | Patient's practitioner; former &/or referred |
| Section 5 | Patient's pain summary. |

Trauma - price, suzy

| Section | Description |
|---|---|
| Section 1 | Patient's current problems from accident & any pre-existing problems; Accident description (Part 1) cause. |
| Section 2 | Accident description (Part 2) sequence of injuries. |
| Section 3 / Section 3b | Accident description (Part 3), description of injuries, degree of pain & hospital admission. |
| Section 4 / Section 4b | Accident description (Part 4), diagnosis, treatment ordered & pain description. |
| Section 5 / Section 5b | Accident description (Part 6), pain description (cont). |
| Section 6 / Section 6b | Accident related pain problems, headache & jaw pain. |
| Section 7 | Physicians consulted since accident. |
| Section 8 | Patient's previous treatment for the injury & affirmation of causation of symptoms. |

Fig. 7B

| Date: | 02-Oct-07 | Patient #: | |
|---|---|---|---|
| | price, suzy | | |

MANDIBULAR RANGE OF MOTION (ROM)

A. LIMITATIONS

1. Opening Movement..................................................... [ ]
2. Lateral Movement
   a. WNL.................................................(12mm-14mm) [ ]
   b. Slight Restriction.................................(10mm-12mm) [ ]
   c. Moderate Restriction............................(7mm-10mm) [ ]
   d. Mod. to Severe Restriction....................(4mm-7mm) [ ]
   e. Severe Restriction.................................(0mm-4mm) [ ]
3. Protrusive Restriction............................................... [ ]

B. PAIN IN ROM

1. WNL........................................................................ [ ]
2. Only at Max Opening................................................ [ ]
3. At 3/4 Opening......................................................... [ ]
4. At 1/2 Opening......................................................... [ ]
5. At 1/4 Opening......................................................... [ ]

Fig. 9B     252

| Date: | 09-Aug-07 | Patient #: | 1 | price, suzy

D. DOPPLER AUSCULTATION FINDINGS

1. Arterial Flow
   a. Normal............................................................
   b. Increased.........................................................
   c. Decreased........................................................

2. Venous Flow
   a. Normal............................................................
   b. Increased.........................................................
   c. Decreased........................................................

3. Click on Opening................................................
4. Click on Closing.................................................
5. Retrodiscal Tissue Tension...................................

Press ✓ (Done) To
Continue the Examination

I. Dental Screening

A. Developmental Stage

B. General Condition of Teeth & Mouth
1. Condition Of Restorations
2. Oral Hygiene
3. Abrasions
4. Quantity of Plaque
5. Quantity of Calculus
6. Stains
7. Tongue Coating
8. Facets /Attrition
9. Erosion
10. Sensitivity Light colored buttons are selected. Dark colored means NOT selected.

C. Missing Teeth

Justification Letters

- Justification Letter 20999
- Justification Letter 21485
- Justification Letter 41899
- Justification Letter 64550
- Justification Letter 78300
- Justification Letter 93875
- Justification Letter 95831

- Justification Letter 95851
- Justification Letter 95999c
- Justification Letter 97120
- Justification Letter 99080
- Justification Letter 99075
- Justification Letter 99090

| Date: | 02-Oct-07 | Patient #: | 3 | price, suzy

I. DIAGNOSTIC TEST AND X-RAYS

A. STUDY MODELS

1. Mounted ☐
2. Unmounted ☐

B. X-RAY

1. Orthopantogram/Panoramic ☐
2. Transcranials ☐
3. Tomograms ☐
4. Arthrogram ☐
5. Cervical Spine Series ☐
6. Cephalogram- Lateral ☐
7. Cephalogram- AP ☐
8. Submental Vertex ☐
9. Bregma-Menton ☐

| Date: | 02-Oct-07 | Patient #: | 3 | price, suzy

I SUMMARY OF SUBJECTIVE COMPLAINTS

A. CHIEF COMPLAINTS AND DEGREE OF PAIN AND DISCOMFORT

1. Headaches..........................................
2. Facial Pain..........................................
3. Jaw Pain............................................
4. Neckaches..........................................
5. Backaches..........................................
   a. Upper Backache..............................
   b. Lower Backache..............................
6. Dizziness............................................
7. Lightheadedness................................
8. Loss of Balance (Disequilibrium)........
9. Fatigue...............................................
10. Eye Pain............................................
11. Visual Disturbances..........................

II JOINT SOUNDS (stethoscopic exam)

A. OPENING CLICK
1. Early
2. Intermediate
3. Full Opening (Late)
4. Eminence

B. CLOSING CLICK
1. Early
2. Intermediate
3. Terminal Closure (Late)
4. Eminence

C. LOUDNESS
1. Audible with Stethoscope
2. Audible w/o Stethoscope
3. Loud

D. DOPPLER AUSCULTATION FINDINGS
1. Arterial Flow
   a. Normal
   b. Increased
   c. Decreased

III NEUROLOGICAL SCREENING

A. Within Normal Limits (WNL)

B. OLFACTORY NERVE I
   1. Smell Compromised

C. OPTIC NERVE II
   1. Can't Read Small Print
   2. Vision Impaired

D. OCULOMOTOR NERVE III
   1. Eyes Don't Move Together
   2. Unequal Reaction to Light
   3. Eyelid Droop E. TROCHLEAR NERVE IV
   1. Lack of Superior Movement F. TRIGEMINAL NERVE V
   1. Corneal Reflex Compromised
   2. Palatal Reflex Compromised
   3. Mandibular Movement Compromised

Date: 14 Nov 07   Patient #: 1 doe, joe l.

IV JOINT AND MUSCLE PALPATION

A. MASSETER
1. Zygoma..................................... R: [ ] L: [ ]
2. Superficial................................. R: [ ] L: [ ]
3. Deep........................................ R: [ ] L: [ ]
4. Lateral Surface (angle of mandible)..... R: [ ] L: [ ]

B. PTERYGOID
1. Lateral (external)........................ R: [ ] L: [ ]
2. Medial (internal)
      a. Body.................................... R: [ ] L: [ ]
      b. Insertion............................... R: [ ] L: [ ]

C. CORONOID/TEMPORAL TENDINITIS..... R: [ ] L: [ ]

D. DIGASTRICS
1. Anterior Belly............................. R: [ ] L: [ ]
2. Posterior Belly............................ R: [ ] L: [ ]

E. MYLOHYOID................................ R: [ ] L: [ ]

F. TEMPORALIS
1. Anterior Fibers............................ R: [ ] L: [ ]
2. Middle Fibers.............................. R: [ ] L: [ ]

Date: 02-Oct-07    Patient #: 3
price, suzy

V MANDIBULAR RANGE OF MOTION (ROM)

A. LIMITATIONS

1. Opening Movement..................................................

2. Lateral Movement
   a. WNL.................................................................. (12mm-14mm)
   b. Slight Restriction............................................... (10mm-12mm)
   c. Moderate Restriction......................................... (7mm-10mm)
   d. Mod. to Severe Restriction................................ (4mm-7mm)
   e. Severe Restriction............................................. (0mm-4mm)

3. Protrusive Restriction............................................

B. PAIN IN ROM

1. WNL.......................................................................
2. Only at Max Opening............................................
3. At 3/4 Opening......................................................
4. At 1/2 Opening......................................................
5. At 1/4 Opening......................................................

Digital Sonogram and Frequency Interpretation # 2

Click Title Box to Change JVA/Sono

A. Right TM Joint:

1. Opening Sound Range
    a. Early............................................................................ ☐
    b. Intermediate................................................................ ☐
    c. Late............................................................................. ☐
2. Closing Sound Range
    a. Early............................................................................ ☐
    b. Intermediate................................................................ ☐
    c. Late............................................................................. ☐
3. Opening Sounds Initiate ................................................. 0 msec/mm
4. Complete Disc Seating ................................................... 0 msec/mm
5. Maximal Vertical Opening .............................................. 0 mm
6. Open Peaks
    a. Number of.................................................................
    b. Size(s) of..................................................

I. DIAGNOSTIC IMPRESSIONS 1. 524-61 Adhesions/Ankylosis (Fibrous/Osseous).................................................P ☐
2. 524-01 Anomalies/Hyper maxilla.........................................................................P ☐
3. 524-02 Anomalies/Hyper mandible......................................................................P ☐
4. 524-02 Anomalies/Hyper mandible......................................................................P ☐
5. 524-04 Anomalies/Hypo mandible.......................................................................P ☐
6. 524-62 Arthralgia of TM Joint..............................................................................P ☐
7. 350-2 Atypical Facial Pain...................................................................................P ☐
8. 351-0 Bell's Palsy................................................................................................P ☐
9. 337-0 Carotidynia................................................................................................P ☐
10. 739-1 Cervical Dysfunction...............................................................................P ☐
11. 723-1 Cervicalgia..............................................................................................P ☐
12. 723-4 Cervical Radiculitis.................................................................................P ☐
13. 723-1 Cervical Strain........................................................................................P ☐
14. 723-5 Cervical Torticollis..................................................................................P ☐
15. 722-0 Cervical Derangement............................................................................P ☐
16. 213-1 Chondroma (Mandible)...........................................................................P ☐
17. 733-92 Chondromalacia....................................................................................P ☐
18. 524-5 Dentofacial Functional Abnormalities.....................................................P ☐

Diagnostic Orthotic Therapy - price, suzy  Appointment 1

Seat Orthotic (Only use on the initial seating) —————— 305

Orthotic Evaluation ——— 306

Orthotic Adjustment ——— 307

ROM Evaluation ——— 308

Myo-Testing ——— 309

Doctor Prescriptions ——— 310

311
Progress Report (At appointments 6&10 and as required)

Doppler Exam ——— 320

↖ 304

Date: 14-Nov-07  Patient #: 1
doe, joe l.

1. Orthotic Evaluation

A. Pain or Soreness Intraorally

1. Right Side — None / Buccal / Lingual
2. Left Side — None / Buccal / Lingual
3. Anterior — None / Buccal / Lingual

B. Pain in or around TM Joints — None / Right / Left / Both

C. TM Joint Pain on...

1. Opening — None / Right / Left / Both
2. Closing — None / Right / Left / Both
3. Chewing — None / Right

D. Locking or Catching in TM Joint

1. Right Side — None / Opening / Closing
2. Left Side — None / Opening / Closing

E. Number of Headaches since last visit — None / One / Daily / Constantly

Fig. 21D          313

3. ROM Evaluation

A. Patient's TM Joint(s) Pain

1. TM Joint(s) in pain at Lateral Position
   - None
   - Right
   - Left
   - Both 2. TM Joint(s) in pain at External Auditory Meatal (Exam) Position
   - None
   - Right
   - Left
   - Both 3. The pain is when
   - None
   - Beginning
   - 1/4 open
   - 1/2 open
   - 3/4 open
   - Full open Jaw Deviation to the...
   - None
   - Right
   - Left was noted... None

B. Jaw Deviation on
   - None
   - Opening
   - Closing

C. Maximum Jaw Opening
   - 20 mm
   - 25 mm
   - 30 mm
   - 35 mm
   - 40 mm
   - 45 mm
   - 50 mm
   - 55 mm
   - 60 mm of...
   - None
   - 1 mm
   - 2 mm
   - 3 mm
   - 4 mm

4. MUSCLE TESTING (Myo-Testing)

The following muscle systems were painful on palpation. Right (R) & left(L) side responses equal degree of pain: Moderate, Severe. Record responses below. Use the drop boxes to display the selection menu. The Blue text will display a picture for the named muscle group when clicked.

1. All systems positive to pain on palpation.............................................. ☐
2. All systems negative to pain on palpation............................................. ☐

A. MASSETER
   1. Zygoma..................................... R: [ ]  L: [ ]
   2. Superficial................................ R: [ ]  L: [ ]
   3. Deep......................................... R: [ ]  L: [ ]
   4. Lateral Surface (angle of mandible) R: [ ]  L: [ ]

B. PTERYGOID
   1. Lateral (external)...................... R: [ ]  L: [ ]
   2. Medial (internal)
      a. Body................................... R: [ ]  L: [ ]
      b. Insertion............................. R: [ ]  L: [ ]

C. CORONOID/TEMPORAL TENDINITIS.. R: [ ]  L: [ ]

D. DIGASTRICS
   1. Anterior Belly............................ R: [ ]  L: [ ]
   2. Posterior Belly.......................... R: [ ]  L: [ ]

E. MYLOHYOID.................................... R: [ ]  L: [ ]

D. DOPPLER AUSCULTATION FINDINGS     Appointment Number:

1. Arterial Flow
   a. Normal
   b. Increased
   c. Decreased

2. Venous Flow
   a. Normal
   b. Increased
   c. Decreased

3. Click on Opening
4. Click on Closing
5. Retrodiscal Tissue Tension

Press √ (Done) To
Continue the Examination

5. Doctor Prescriptions

1. Patient to Re-Appoint in...
   - None
   - 24 Hours
   - 3 to 4 days
   - 1 week
   - 1 month 2. Patient to orthotic wear...
   - None
   - 24hrs
   - Daytime only
   - Nightime only
   - 2 hr less/day til pain returns 3. Patient to continue physical therapy prescribed?
   - Yes
   - No

4. Patient to continue medication prescribed?
   - Yes
   - No

5. Patient Diet...
   - Normal
   - Soft
   - Semi-Soft

Press √ (Done) To Continue the Examination

Fig. 23A — 318

6. Progress Report

1. TM Joint Sounds..................................................
2. TM Joint Pain....................................................
3. TM Joint Dysfunction.............................................
4. Masticatory Muscle Spasm.........................................
5. Other Muscle Spasm...............................................
6. Pain of:
    a. Head........................................................
    b. Neck........................................................
    c. Shoulders...................................................
7. Headaches.......................................................
8. Pain Associated with ears.......................................
9. Bruxing and Clenching...........................................

10. Teeth Sensitivity..............................................
11. Tinnitus.......................................................
12. Dizziness......................................................
14. "Clogged" Ears.................................................
15. Sinus Symptoms.................................................
16. Other..........................................................

| Doctor Id: 2 | | NPI#: | |
|---|---|---|---|
| Treating Physician: | Dr. Aleve, DDS | | |
| Practice Name: | | | |
| Street Address: | 1234 Broadway | | |
| City: San Antonio | | State: Tx | Zip Code: 78209 |
| Phone #: (123) 456-7890 | | Fax #: | |
| Fed Tax I.D.: 74-342343 | PIN#: 12345 | | Blue Cross: 12345 |
| ID # Type: EIN | Medicare: 12345 | | Commercial: 12345 |
| SS#: 096-76-5432 | Medicaid: 12345 | | Champus: 12345 |

Letter Head

Dr. A. Aleve
1234 Broadway
San Antonio, TX
78209

| Name | Service Code | Work Comp | Charge |
|---|---|---|---|
| 3-D CT (invalid) | 76375 | 76375 | |
| Acupuncture, Electro/Aricular | 97813 | 97813 | 125 |
| Acupuncture, Electro/Aricular (Old) | XXXX | XXXX | 0 |
| Airway Closing Vol, sgl breath tests | 94370 | 94370 | 0 |
| Airway Obstruct,Nonpressure Inhalation | 94640 | 94640 | 0 |
| Analysis info in computer (PtLtr) | 99090 | 99090 | 65 |
| Arthrocentesis w/ Report | 20600 | 20600 | 1250 |
| Arthroplasty, Assistant Surg | 21240 80 | 21240 80 | 1905 |
| Arthroscopy, TMJ Assistant Surg (invali | 29804 80 | 29804 80 | 1057 |
| Arthroscopy, Diagnostic | 29800 | 29800 | 2900 |
| Attorney Letter # 1 (invalid) | Z4001 | Z4001 | 0 |
| Bio-conductive TENS w/ Report (invalid) | 97039 | 97014 | 65 |
| Biofeedback | 90901 | 90991 | 85 |
| Breathing Capacity, max vol ventilation | 94200 | 94200 | 0 |
| Chronic Pain Battery Test(by Physician) | 96100 | 90830 | 145 |
| Chronic Pain Battery Test(by Physician)( | 96101 | 96101 | 145 |
| Comp Clinical Exam, est pt(CME II) | 99245 | 99245 | 325 |
| Comp Clinical Exam, est pt(CME II)(old) | 99215 | 90080 | 125 |
| Coronoplasty Limited (invalid) | 20999b | 22299b | 150 |
| Coronoplasty, Comprehensive | 21299 | 21299 | 375 |
| CT (Computerized Tomography) | 70486 | 70486 | 615 |
| Determination of Airway Closing Volume | 94370a | 94370a | 0 |
| Diagnostic Report (invalid) | Z6000 | Z6000 | 0 |
| Diagnostic Study Casts | 41899 | 41899 | 95 |
| Doctor Letter # 1 (invalid) | Z4000 | Z4000 | 0 |
| Doppler Exam Art., BiLat., Rpt | 93875 | 93875 | 65 |
| Doppler Excrnl Art.,BiLat.,w/Report(2)(inv | Z1000 | Z1000 | 0 |
| Electromyography, Craniel Nerve Bilat. | 95868 | 95868 | 195 |
| Electromyography, sgl fiber,ea myo (inval | 95872 | 95868 | 145 |
| Emergency Office Visit | 99284 | 99284 | 275 |
| Emergency Office Visit (old) | 99244(old) | 90660 | 97 |
| EMG Electrodes | 99070 | 99070 | 35 |
| Hearing Screen-air only w/Report | 92552 | 92552 | 50 |
| Hearing Screen-air only w/Report (Old) | 92551 | 92551 | 48 |

SYSTEM AND METHOD OF TREATING TEMPRO MANDIBULAR DISORDERS UTILIZING A PROTOCOL OF EXAMINATIONS, DIAGNOSTICS, PROCEDURES AND TREATMENTS TO GENERATE LETTERS, REPORTS AND CODED INSURANCE CLAIM FORMS TO MAXIMIZE BENEFIT PAYMENTS

BACKGROUND OF THE INVENTION

1. Field of the Invention

The present invention relates to a method and interactive system which establis a protocol of appointments, examinations, diagnostics, procedures and therapy in the treatment of Temporomandibular Disorders (TMD) by a dentist, from which properly coded medical insurance claim forms are generated, increasing the probability of approval of payments to the dentist.

2. Description of the Related Art

Two common health benefits employers provide to employees are medical insurance plans and dental insurance plans. Both medical insurance and dental insurance plans can vary in the types of coverages that are offered. The term "insurance plan" extends to any contractual or other legal arrangement whereby medical and other related expenses are paid on behalf of a beneficiary. Examples of insurance plans include health maintenance organizations, preferred provider organizations, fee-for-service health care plans, employer-sponsored insurance plans, etc. Most insurance plans cover illness and injuries at certain percentage levels and may include co-payments, deductibles and coverage limits. A typical medical insurance plan might be one where the insurer will pay 80% of physician's bill associated with the diagnosis and treatment of a condition. The patient would be expected to pay the remaining 20% of the bill, after paying a deductible (a predetermined minimum contractual amount that must be paid before the insurance plan begins coverage) and co-payment (a per visit amount paid before coverage is extended).

Dental insurance plans can be similar to medical insurance plans, but typically coverages are at lower levels and have higher co-payments and deductible amounts than medical insurance plans. A typical dental insurance plan might cover preventive and diagnostic services at 100% (generally cleanings and checkups), but will cover more involved treatments at lower percentages. For example, basic services might be covered at 80%, major services and orthodontics might be covered at only 50%. In addition, dental insurance plans often have both annual and lifetime maximum benefits, for example, an annual per person maximum of $1,200 or a lifetime per person of $1,500 for orthodontics are routinely used limitations. Further, deductibles and co-payments may apply, further limiting benefit coverage.

Typically, medical doctors diagnose and treat medical conditions, and look to medical insurance plans for reimbursement. Dentists diagnose and treat dental conditions, and seek reimbursement from dental insurance plans.

In situations where a Dentist provides treatment to a patient where, under medical and dental industry standards, medical insurance coverage could be utilized instead of dental insurance coverage, several advantages could be realized. Because medical insurance coverage percentages and limits are generally higher, a Dentist able to process an insurance claim under a medical insurance plan rather than dental insurance plan could recover greater amounts from the insurer and less from the patient, reducing the need for arranging patient payment of uninsured costs and payment collections, as well as higher patient satisfaction in obtaining services for lower out-of-pocket cost to the patient.

Medical claim forms are filled out and submitted to insurance companies containing industry standard numerical descriptions known as ICD 9 (International Statistical Classification of Diseases and Related Health Problems codes) codes and CPT (Current Procedural Terminology) codes. An ICD 9 code describes a specific medical condition or diagnosis. CPT codes describe medical, surgical, radiology, laboratory, anesthesiology, and evaluation/management services of physicians, hospitals, and other health care providers. An additional 2 digit modifier may be added to a CPT code following a decimal point to clarify or modify a procedure.

The purpose of the coding system is to provide uniform and standardized descriptions that accurately describes medical conditions and the medical, surgical, and diagnostic services used to treat these conditions. The rules for assigning ICD 9 and CPT codes are complicated and extremely detailed. Training and experience is necessary to consistently and properly apply the appropriate codes in a manner to insure medical health claims are processed correctly and paid promptly.

A submitted medical insurance claim form typically contains ICD-9 code or codes, describing a condition. For each ICD code listed in an insurance claim form, a health care provider may decide to implement a treatment or treatments, each of which has a CPT Code that describes it. Together, the ICD code is matched with the appropriate CPT code or codes detailing the diagnosis and treatment of a condition. The codes used are examined, both manually and by the use of computer software to insure that the procedure and the diagnosis are related and that the procedure is one of medical necessity for that diagnosis.

A large portion of the medical expenses incurred by patients in this country are paid by private or government based insurance plans. Agencies such as health insurers, health care consultants, government offices (i.e. Medicare/Medicaid) routinely examine health claim forms to verify that the treatments being administered fall within accepted guidelines to avoid paying for unnecessary or unconventional treatments, as well as to prevent overpayments due to improper coding. Also, because of the high rates of insurance fraud, these agencies rely on computer and manual audits to analyze submitted documentation and deny claims when these audits detect irregularities. This necessitates that forms be coded properly the first time to avoid the red tape and bureaucracy that is involved to correct mistakes that result in denial of claims. By automating the process, human error is minimized and coding is done correctly according to industry standards, thereby reducing the rates of claim rejection.

The temporomandibular joint connects the lower jaw (mandible), to the temporal bone at the side of the head. Because these joints are flexible, the jaw can move smoothly up and down and side to side, enabling actions such as speech, chewing and yawning. Muscles attached to and surrounding the jaw joint control its position and movement.

Temporomandibular Disorder (TMD) describes a group of conditions that affect the Temporomandibular Joint (TMJ) and the related muscles. TMD generally refers to the more general diagnosis of one of the following specific conditions:

TMJD (Temporo-Mandibular Joint Dysfunction)
TMJ (Temporo-Mandibular Joint)
TMD (Temporo-Mandibular Disorder)
CFD (Cranio-Facial Disorder)
CCD (Cranio-Cervical Disorder)
CMD (Cranio-Mandibular Disorders)

These various disorders usually involve similar symptoms, which include pain, dysfunction and impairment involving the head, neck, ears and jaws. TMD diagnosis and treatment fall into 2 general categories:

Extra-capsular—any condition outside the TMJ capsule

Intra-capsular—involving in the working inside the TMJ capsule.

Extra-capsular TMDs are considered soft tissue injuries and are typically covered by dental insurance, whereas intra-capsular conditions are considered hard tissue problems involving trauma-related injuries, and may be covered by the patients' medical insurance since they are considered to be medical rather than dental treatments.

Because treatment may involve either category of insurance, it is important that not only the proper coding be used but that the coding be classified under the proper type of insurance. Because medical and dental insurance coverages are fundamentally different, proper claim submission for Intra-capsular Temporomandibular Disorders would involve experience and knowledge in two very different areas of insurance claim coding.

Because intra-capsular injuries are non-surgical problems, claims may be submitted under a patient's medical insurance coverage. A dentist treating these conditions must have the ability to effectively code both diagnosis and treatment under the proper ICD 9 and CPT medical codes to insure medical insurance claims will be paid promptly and not rejected.

SUMMARY OF THE INVENTION

In accordance with the present invention, an interactive system and a method for generating properly coded medical insurance claim forms in the treatment of Temporomandibular Disorders by dental care providers, by using a protocol of steps consisting of appointments, diagnostics, examinations and procedures and compiling the information gained from these steps to effectively treat the condition and classify the treatments to maximize successful health benefit recovery.

It is therefore an object of the present invention to provide an interactive system and method to logically, systematically, and efficiently detail a consistent course of evaluation and treatment of Temporomandibular Disorders in which these evaluations and treatments are performed in specific appointments.

It is another object of the present invention to provide a system and method that will classify the evaluation and treatment procedures of patients with Temporomandibular Disorders as health insurance claims as opposed to dental insurance claims for purposes of greater insurance coverage, and generate properly coded medical insurance claim forms and other supporting reports and letters as documents in printed or electronic form.

It is a further object of the present invention to provide a system and method for preparing properly coded insurance claim forms according to American Medical Association standards for submission, thereby reducing errors and denial or delay in claim reimbursement.

Still other objects, features, and advantages of the present invention will become evident to those of ordinary skill in the art in light of the following. Also, it should be understood that the scope of this invention is intended to be broad, and any combination of any subset of the features, elements, or steps described herein is part of the intended scope of the invention.

BRIEF DESCRIPTIONS OF THE DRAWINGS

FIGS. 4, 5, 6A-6D, 7A-7C, 8, 9A-9C, 10A, 10B, 11A-11D, 12A-12C show examples of user menus and data entry screens associated with the flowchart described in FIG. 3.

FIG. 14 shows an example of data entry screens associated with the flowchart described in FIG. 13.

Figure 17C:
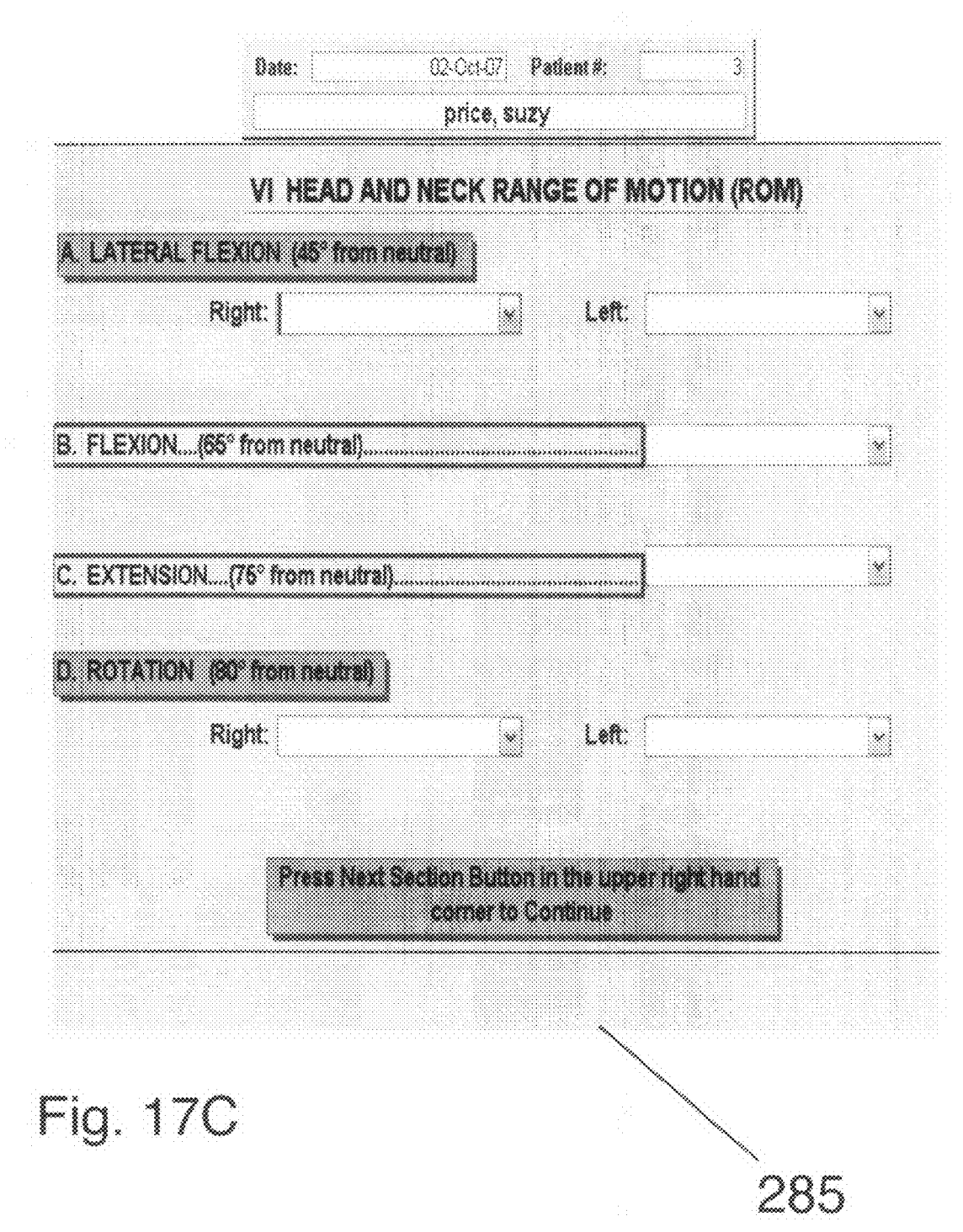
Figure 19A:
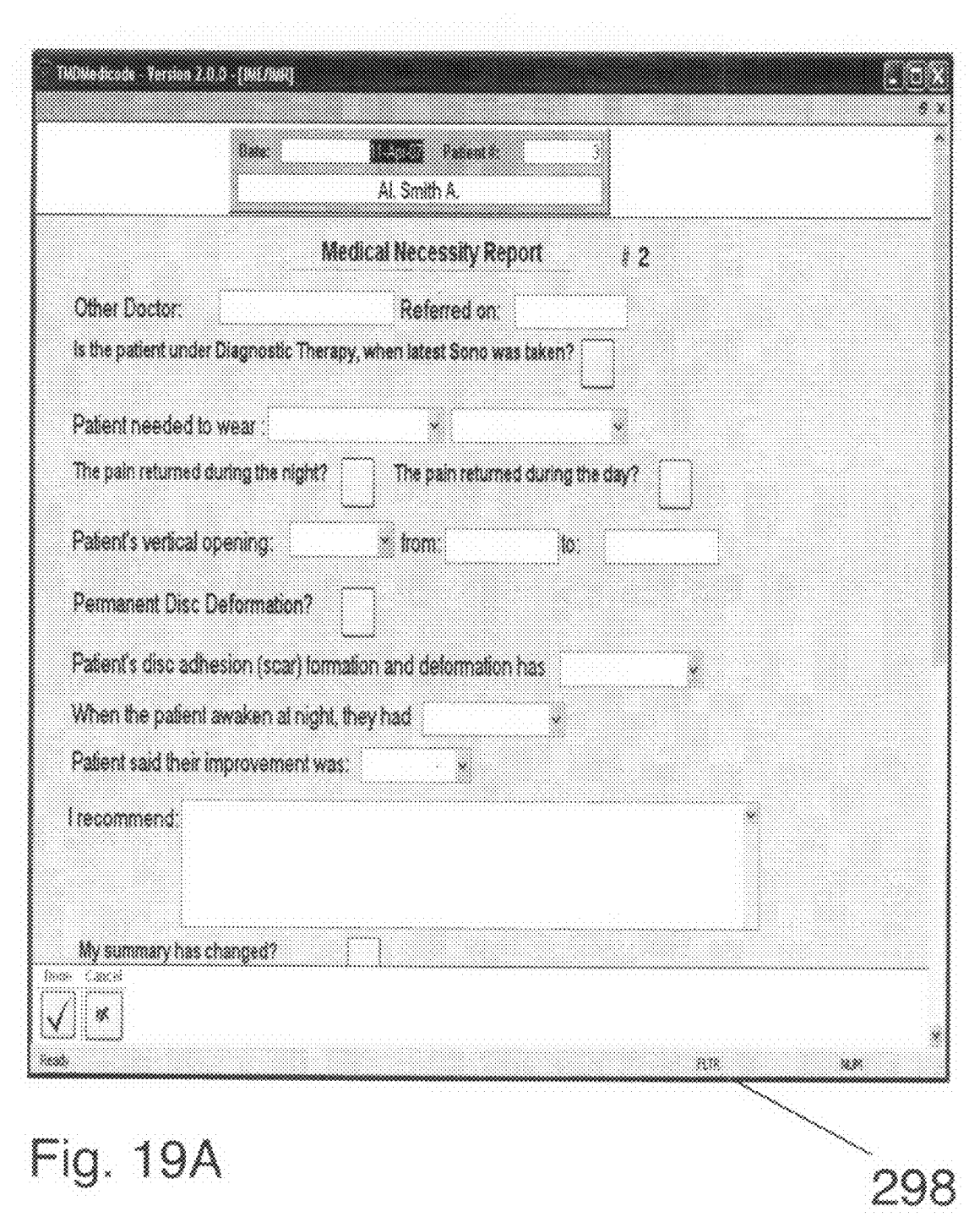

FIGS. 16A-16D, 17A-17D, 18A-18D, 19A, 19B show examples of user menus and data entry screens associated with the flowchart described in FIG. 15.

FIGS. 21A-21D, 22A-22D, 23A-23B show examples of user menus and data entry screens associated with the flowchart described in FIG. 20.

Figure 30A:
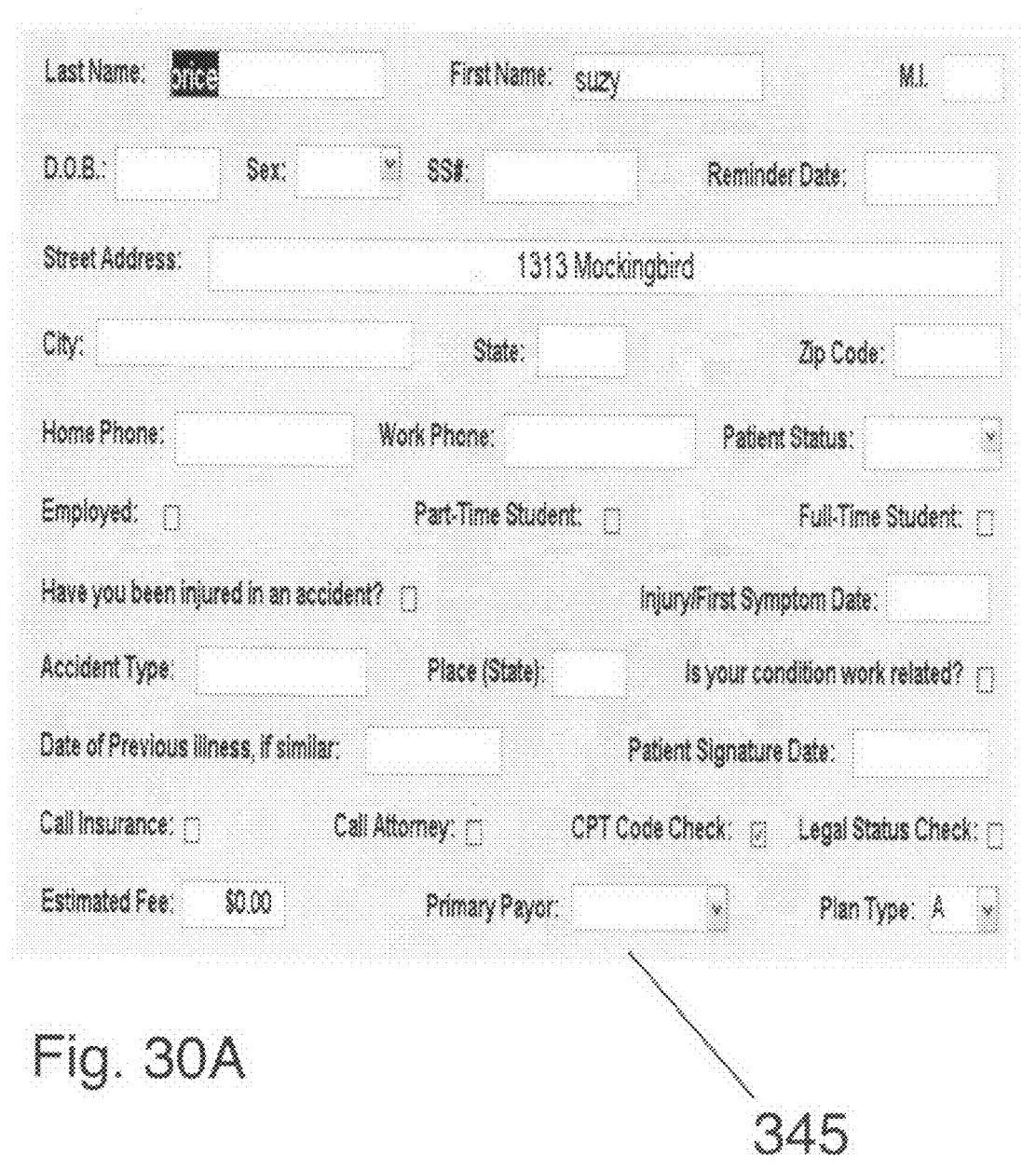
Figure 30B:
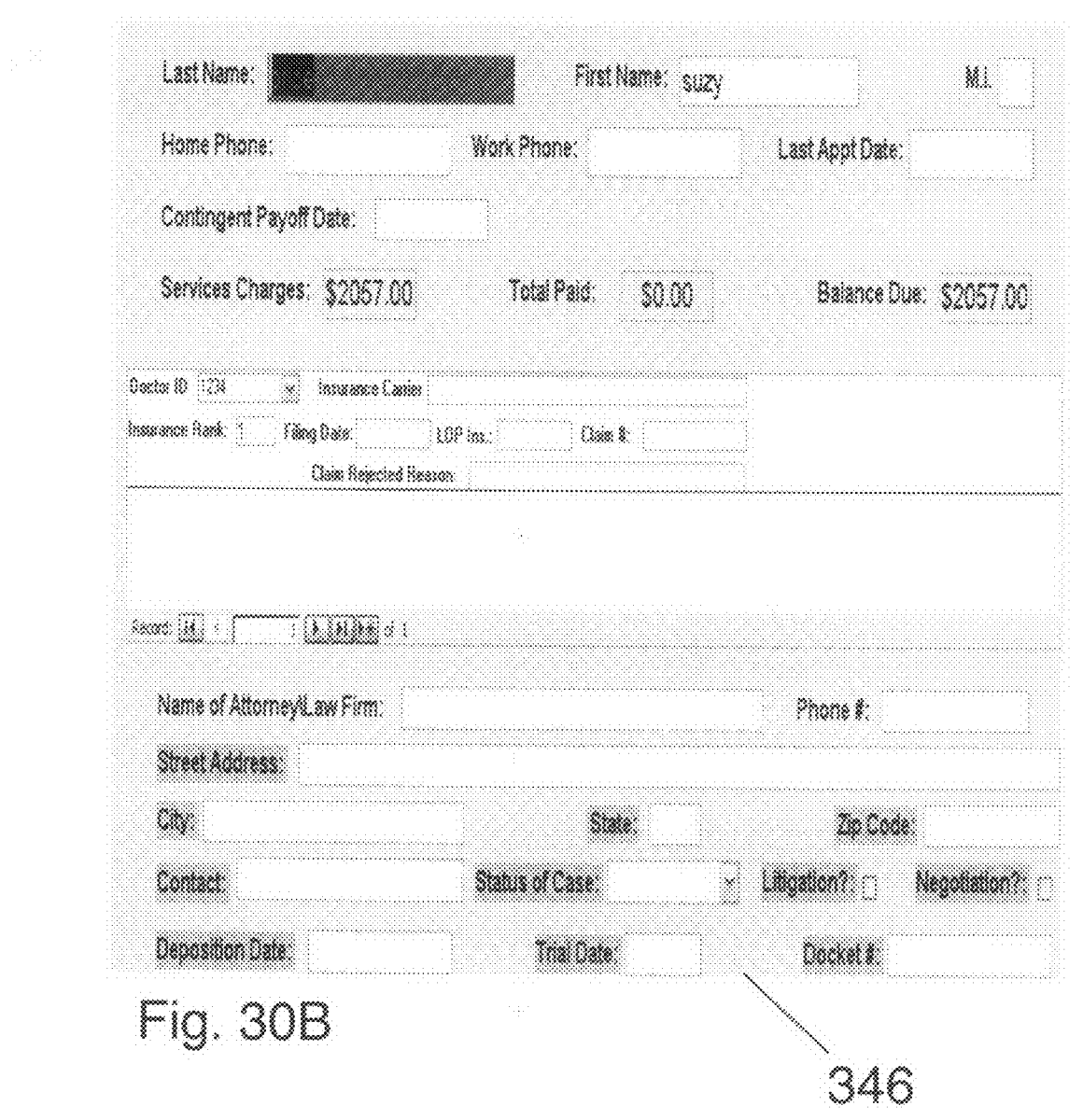
Figure 30C:
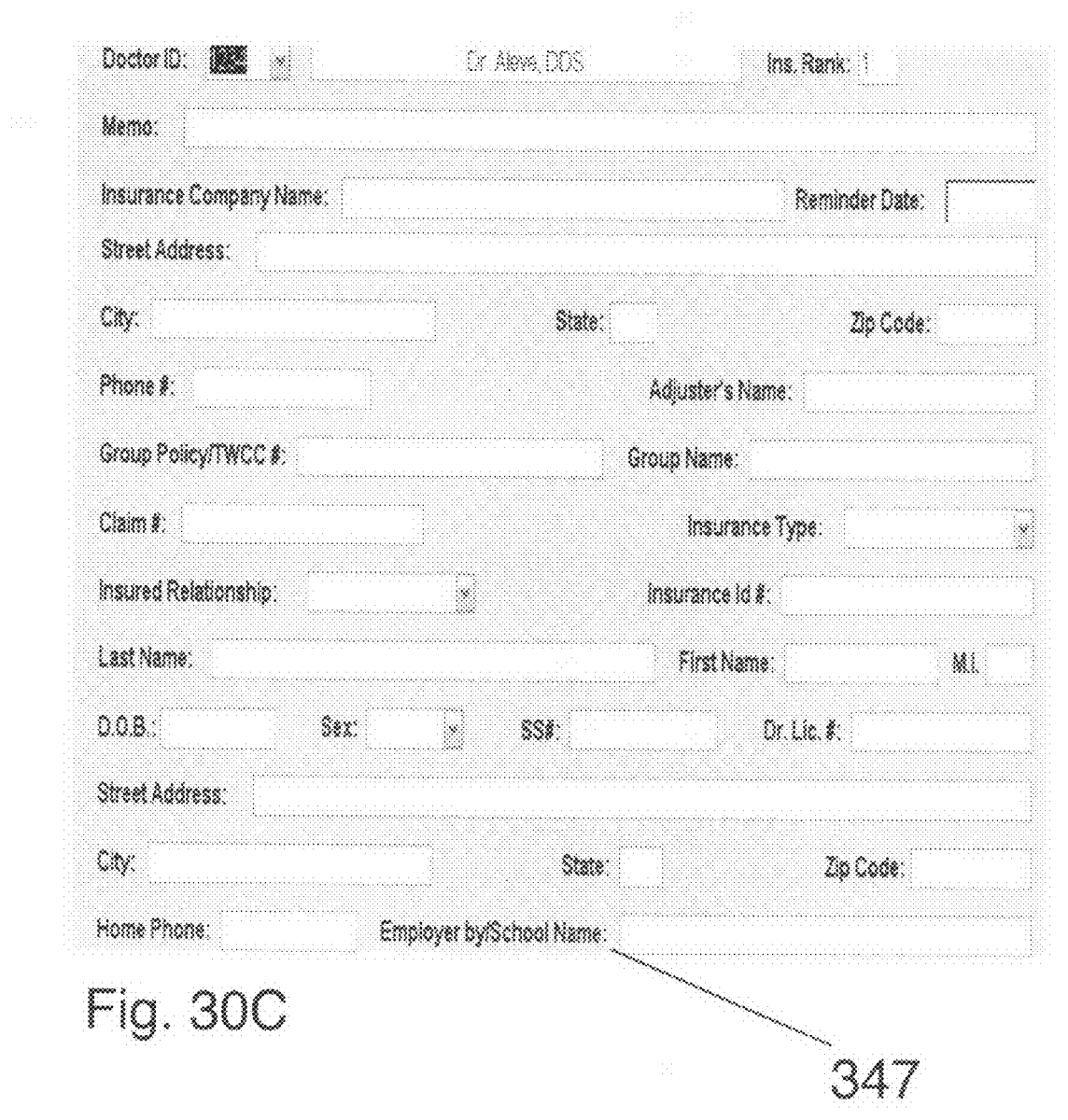
Figure 30D:
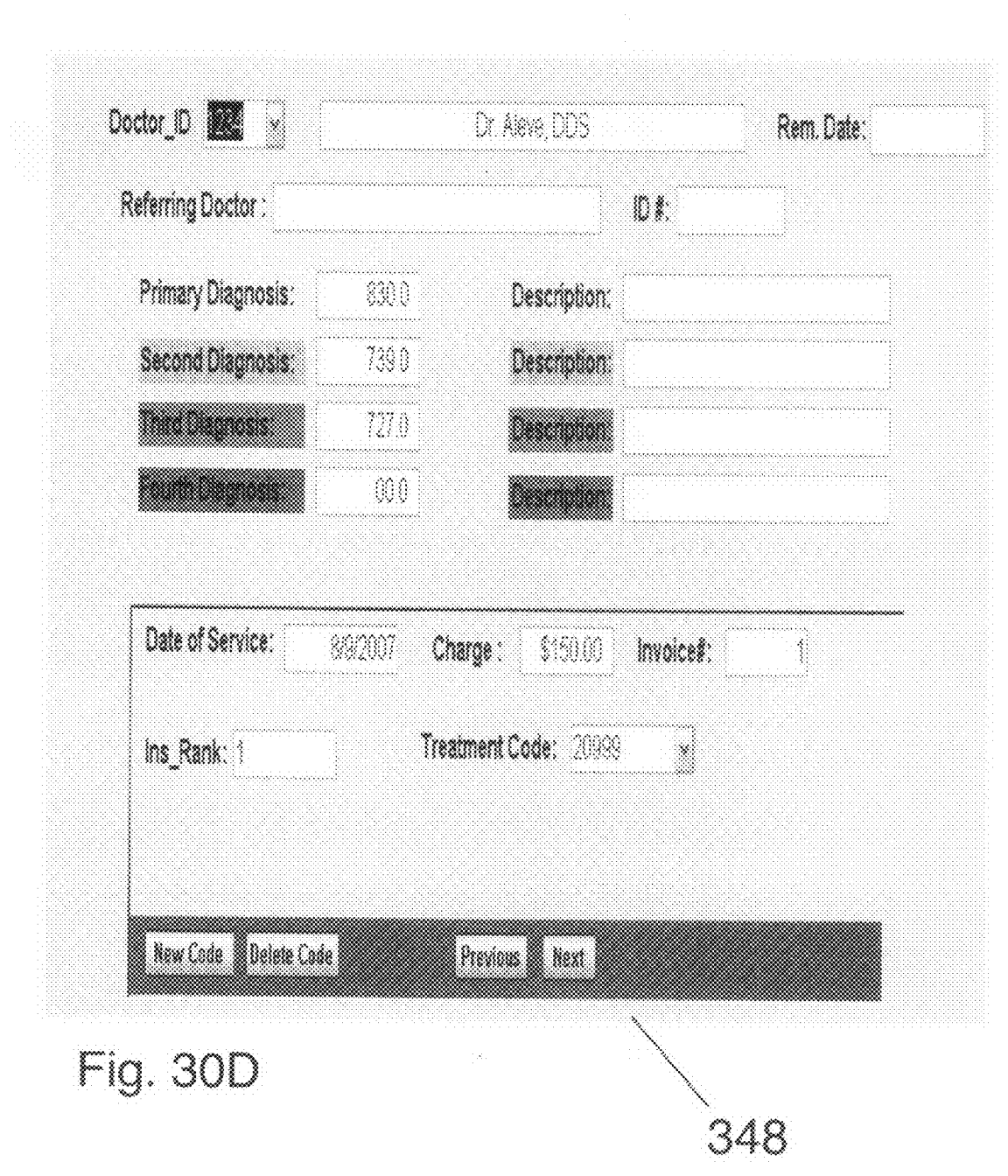
Figure 31C:
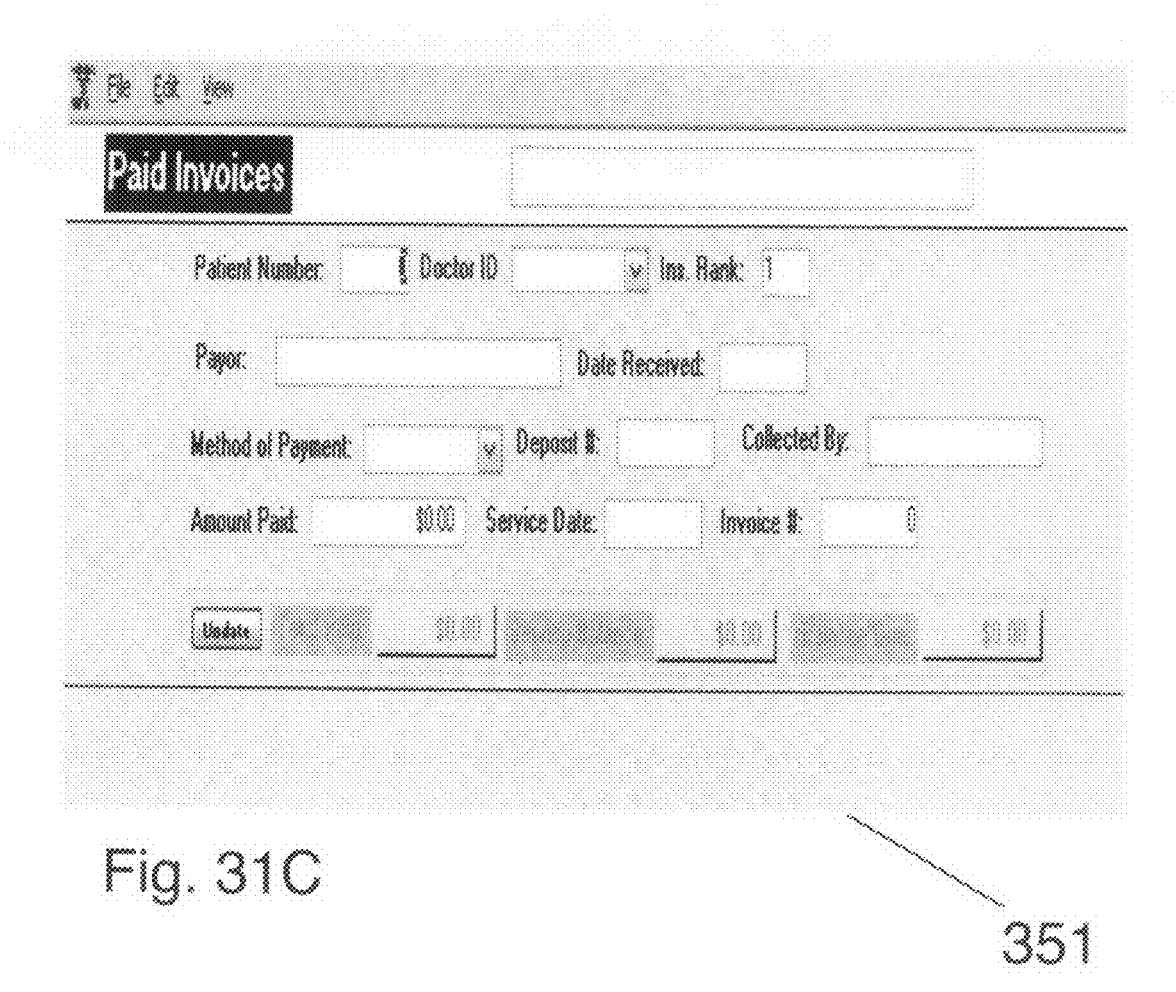
Figure 32B:
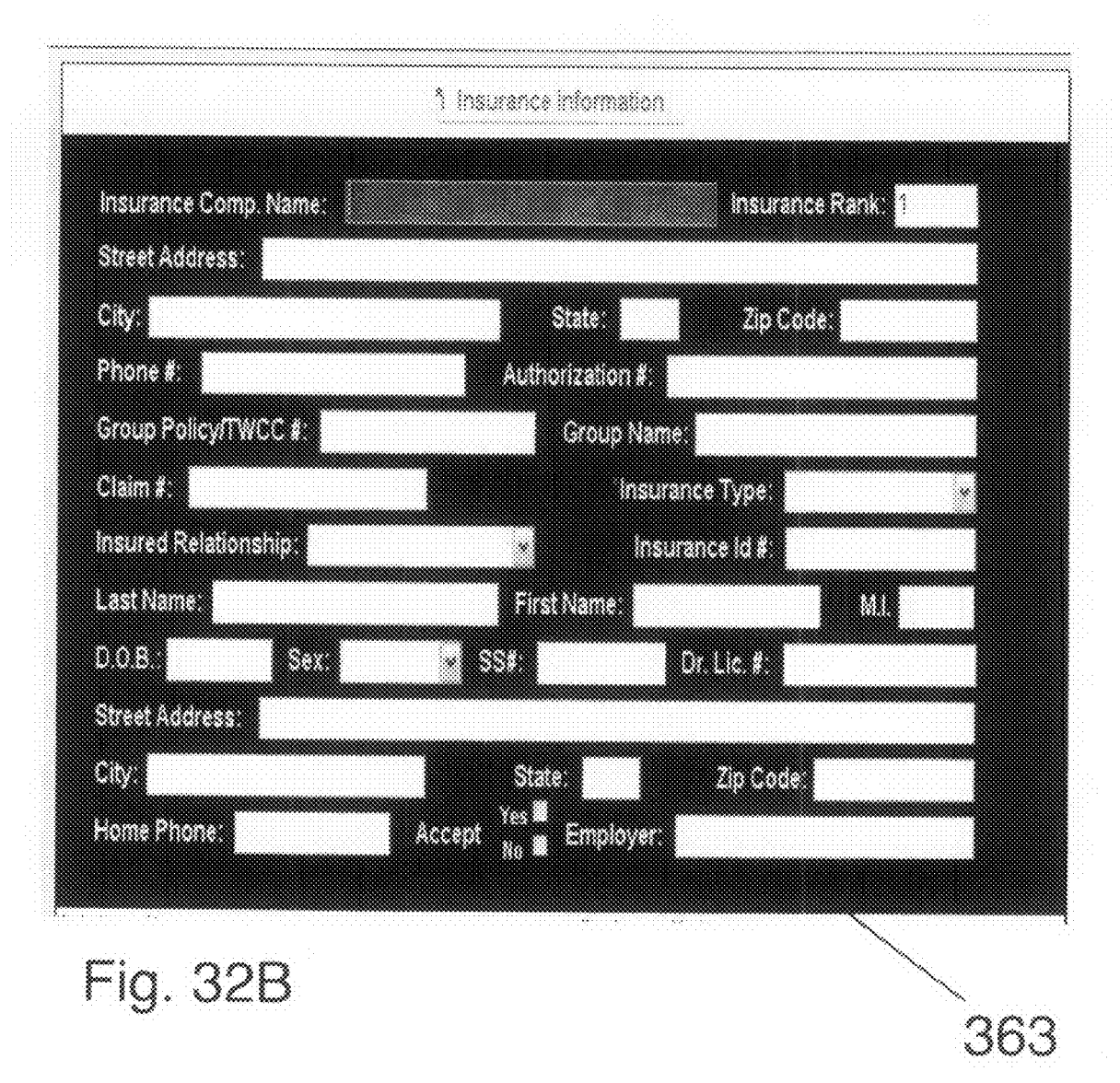
Figure 33:
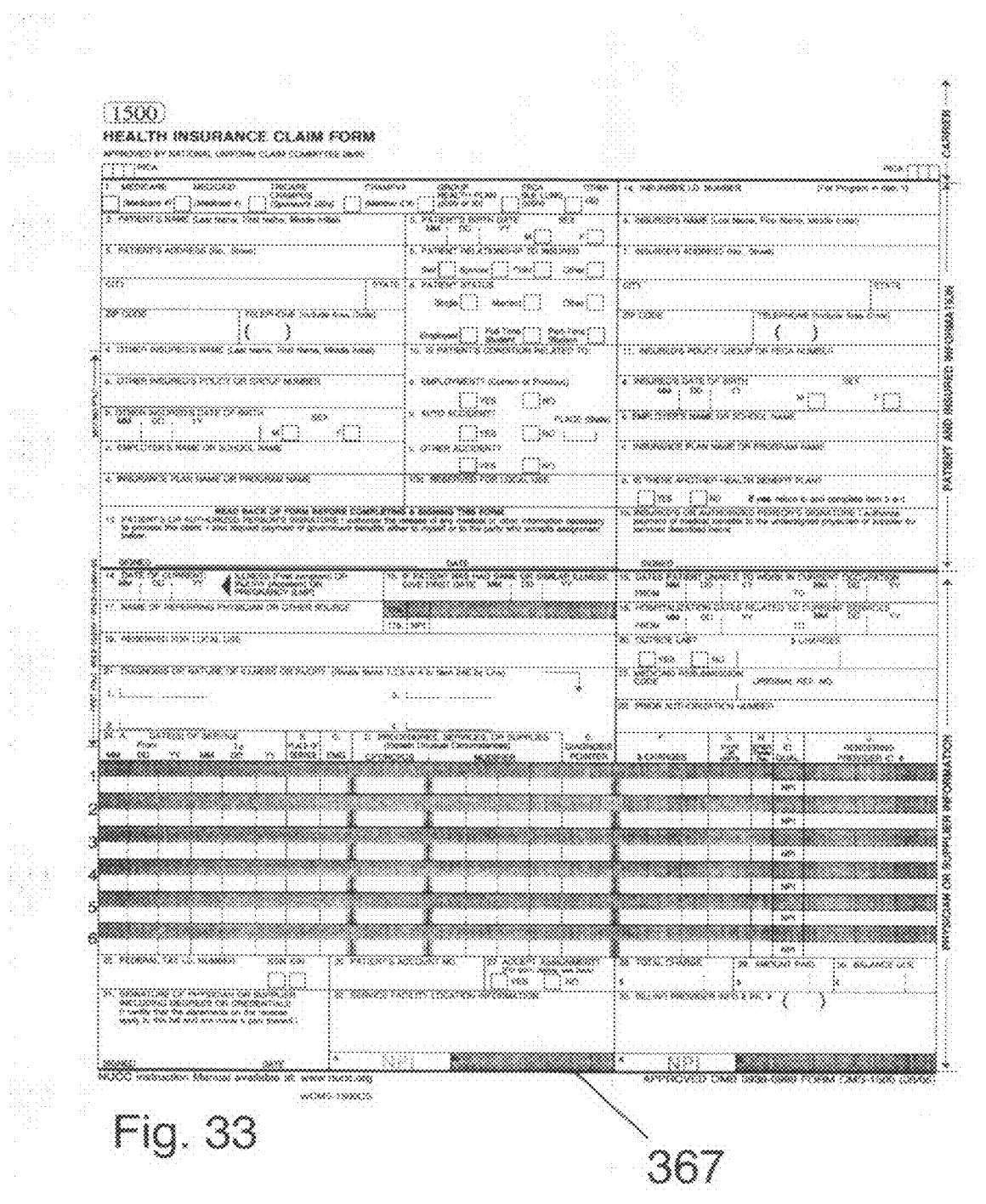

FIGS. 29, 30A-30D, 31A-31C, 32A-32C, 33, 34A-34C show examples of user menus and data entry screens associated with administrative and System Setup subroutines.

DETAILED DESCRIPTION OF THE PREFERRED EMBODIMENTS

The present invention relates to a method and system for following a course of treatment, examinations, diagnostics, evaluations and procedures in the treatment of Temporomandibular Disorders, and obtaining and processing data to prepare properly coded medical insurance claims and supporting documents in a dental office.

Figure 1:
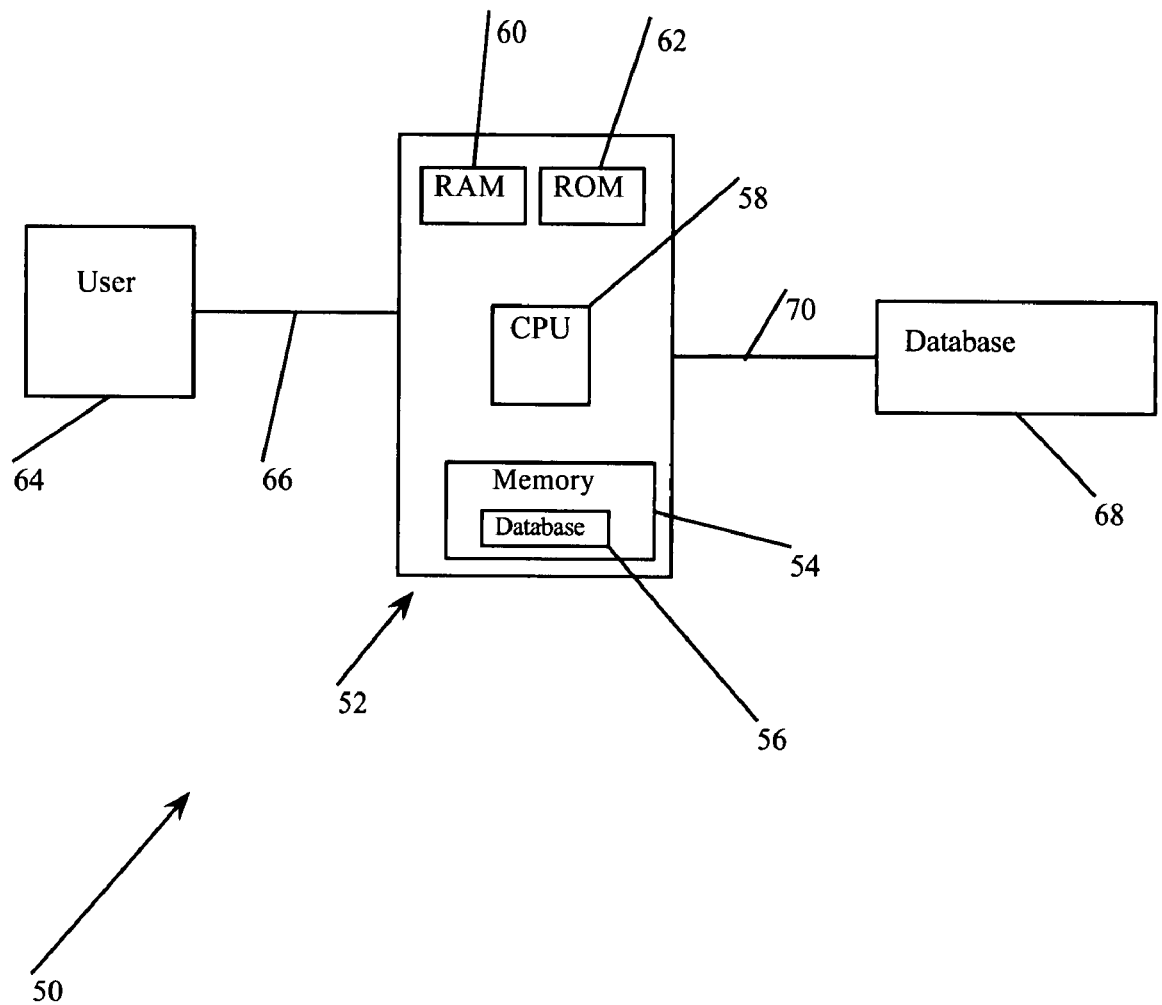
FIG. 1 illustrates the client-server-database configuration for the system.

The system 50 depicted in FIG. 1 includes a server 52 having a memory 54, and a database 56 defined in memory 54. The server 52 may be a dedicated server, a minicomputer, a microcomputer, a UNIX machine, a mainframe computer, a personal computer with an Intel Pentium (or the like) processor, a Macintosh computer, or any other suitable computer. The memory 54 is preferably non-volatile and includes storage devices, such as CD-ROMs, hard disks, tape drives, etc. The server 52 has a central processing unit (CPU) 58, input devices such as a keyboard and mouse (not shown), output devices such as a monitor and printer (not shown), random access memory (RAM) 50, read-only (ROM) 52, as well as input/output (i.e. serial, parallel, USB, Firewire (IEEE 1394) ports and the like) ports (not shown). There may also be additional memory (not shown) remote from the server 52 and connected to the server 52 via one of the aforementioned ports. The server 12 may also connect to the Internet via a modem or other networking hardware (not shown). In one embodiment, system 50 is a single computer where the server 52 and components are a single workstation. In another embodiment, server 52 is a separate server, such as a World Wide Web server connected to the Internet. In this embodiment, the server 52 has an operating system that is capable of multiple users and multi-tasking, such as UNIX, Windows NT, or LINUX. FIG. 1 depicts a user 64, but could include one or more users 64 and one or more external databases 68 which communicate with the server 52. FIG. 1 does not disclose the specific interconnections between and among the various components in the system 50 as this information is well known. User 64 may be an individual directly accessing server 52, or a minicomputer, a microcomputer, a UNIX machine, a mainframe computer, a personal computer with an Intel Pentium processor, a Macintosh personal computer, a laptop, a personal data assistant (PDA), a pen computer, a kiosk or any other suitable computer on a network.

The user 64 may communicate directly to the server 52 in the single computer embodiment or by communication links 66 in an embodiment where server 52 is a separate server, and the external databases 68 may be connected to the server 52 by communication links 70. The communication links 66, 70 between the server 52 and the client machines 64 and between the server 52 and the external databases 68, respectively, may include a large variety of connections, including a telephone link, a hard-wired connection, a satellite link or other wireless connection, an Internet connection, a local area network (LAN), a wide area network (WAN), any combination of the preceding, or any other suitable type of connection. Multiple users 64 may communicate simultaneously with the server 52, and each connection may be by a different type of link, e.g., one connection may be by telephone while another may be by the Internet. Similarly, multiple external databases 68 may communicate simultaneously with the server 52, and each connection may be a different type of link as discussed above.

The server 52 may communicate, via communication link 70, with a particular database 68 by a variety of communication protocols, including file transfer protocol (FTP), electronic mail (e-mail), transfer control protocol/Internet protocol (TCP/IP), ASCII, X-MODEM, Y-MODEM, KERMIT, any combination of the preceding protocols, or any other suitable type of protocol. The server 52 may gather information from a database 68 automatically, e.g., at regularly scheduled intervals, only in response to data requested from a user 64, or both automatically and in response to a request from a user 64. Depending on the nature of the information provided by a database 68, the connection between the server 52 and the database 68 may be "live" at all times or may be established intermittently.

After a link is established between the server 52 and user 64, communication may take place via a variety of communication protocols, as described above with respect to communication between the server 52 and database 68. The software used by user 64 that accesses information on the server 52 may be a known Internet browser such as Netscape Navigator or Internet Explorer or may be any other type of software suitable for transmitting information to and receiving information from the server 52.

In an embodiment involving multiple users 64, the server 52 is an independent server. With this platform, CPUs, memory, networking capabilities, storage, and software may be modified as appropriate to meet specific requirements. The selection of a suitable server requires consideration of CPU speed as well as disk subsystem performance and network bandwidth. For example, a disk with a 7200 RPM rotational speed may be a suitable disk subsystem. Once the RAID is selected (RAID 0, 1, 2, 3, 4, or 5), the size of the database and its projected growth must be analyzed as part of the known design considerations.

The database 56 on the server 52 may be of any suitable type that may be used for large database applications.

In a one embodiment, a user 64 connects to the server 52 via a communication link 66. The user 64 may then log onto the database 56.

After accessing the server 52, a user 64 may enter pertinent information into the database 56 concerning the type or types of information desired. As discussed below, a wide variety of data may be entered into database 56. The server 52 may be connected to one or more databases 56, 68, located internal to the server, external to the server, or in combination of internal and external locations. Once the information from one or more of the databases 56, 68 is entered or further processed within the database 56, a search may be performed using server 52 to identify information requested by a user 64. The server 52 may then format the requested information appropriately. Once the information is formatted, it may then be transmitted to user 64.

Figure 2:
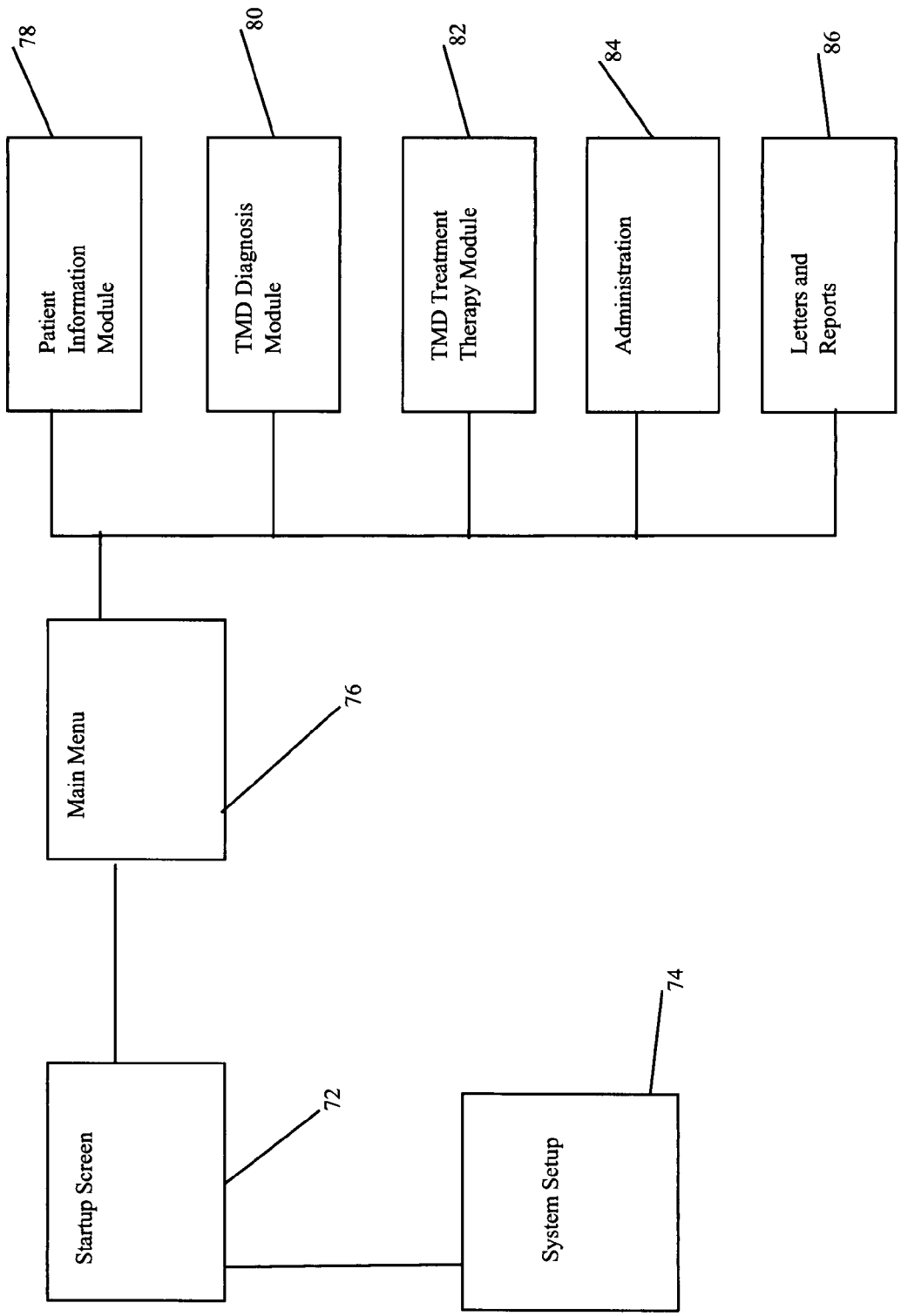
FIG. 2 illustrates an overview of the various modules and subroutines of the system.
Figure 3:
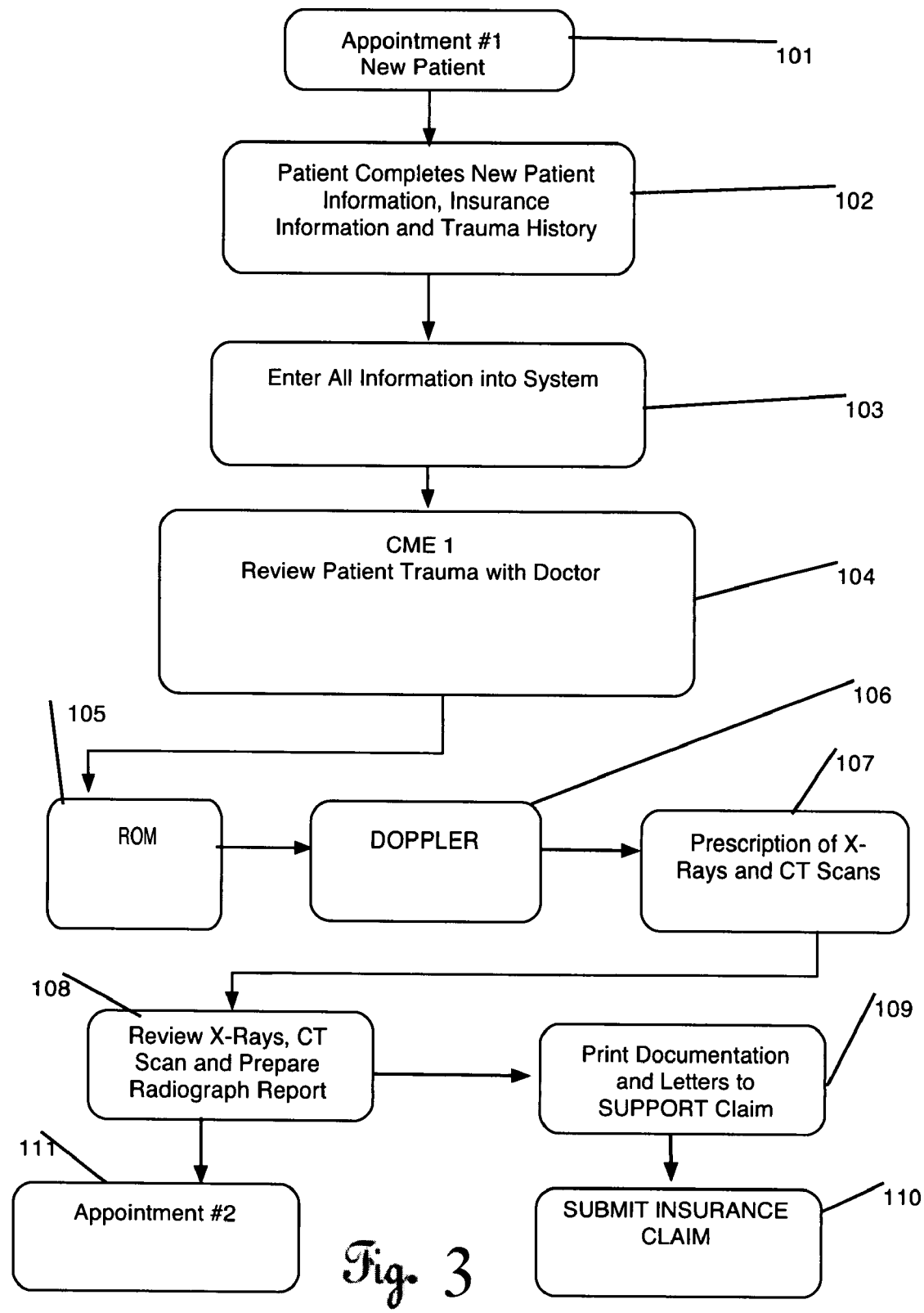
FIG. 3 is a flowchart describing the general method of obtaining, entering and processing background information and preliminary medical findings for new Temporomandibular Disorder patients for the First Appointment.
Figure 4:
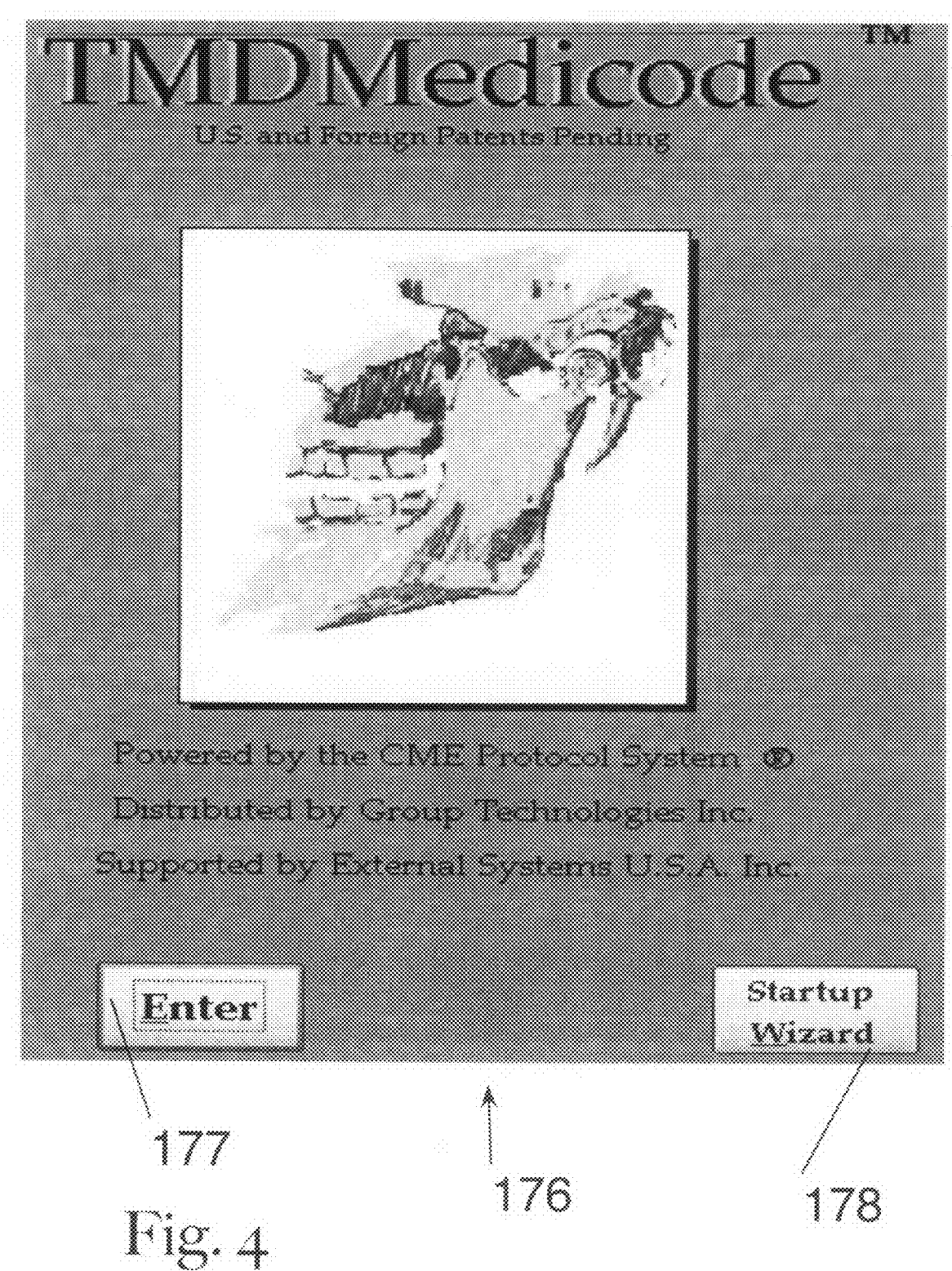
Figure 5:
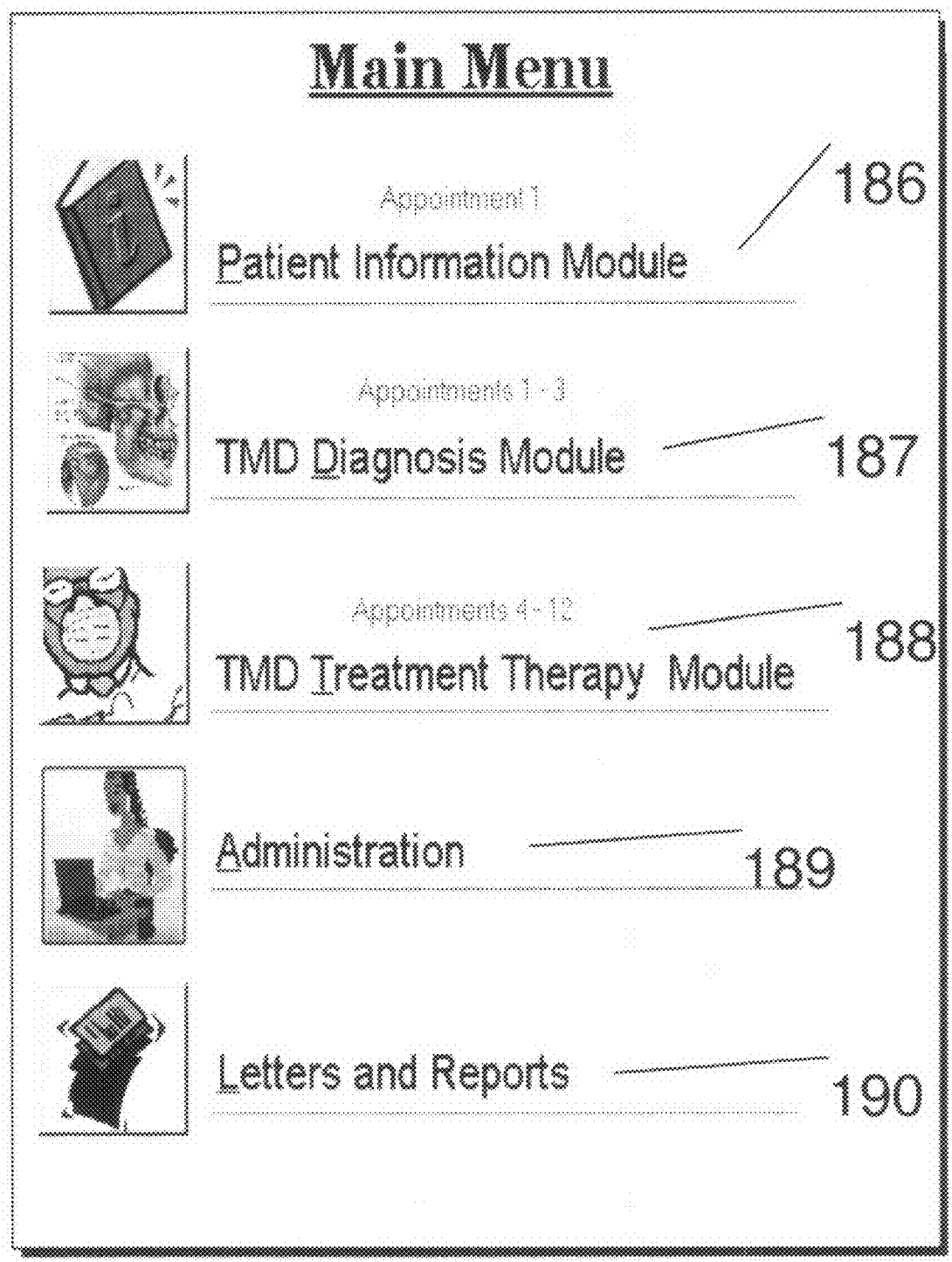
Figure 6A:
Figure 6C:
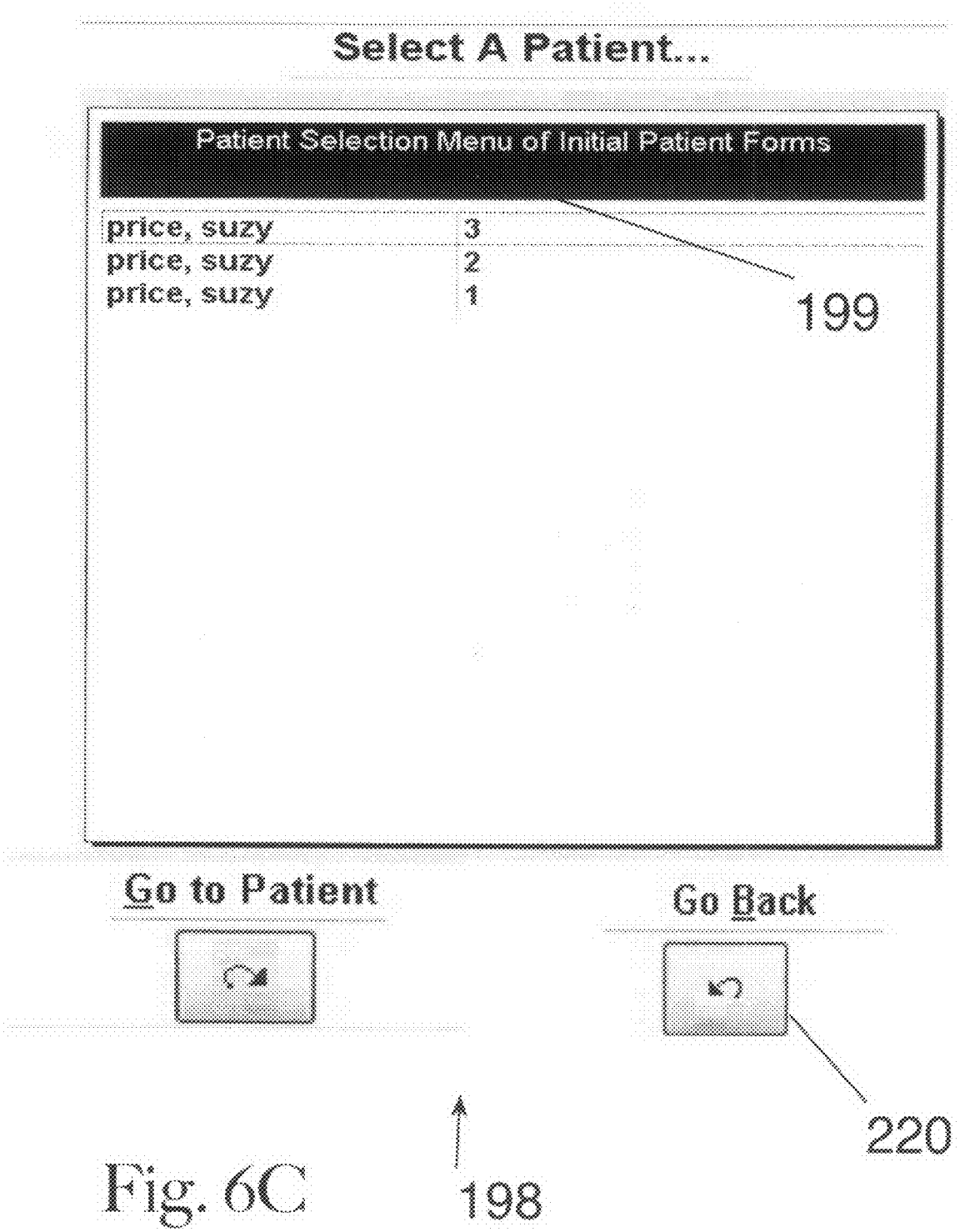
Figure 7C:
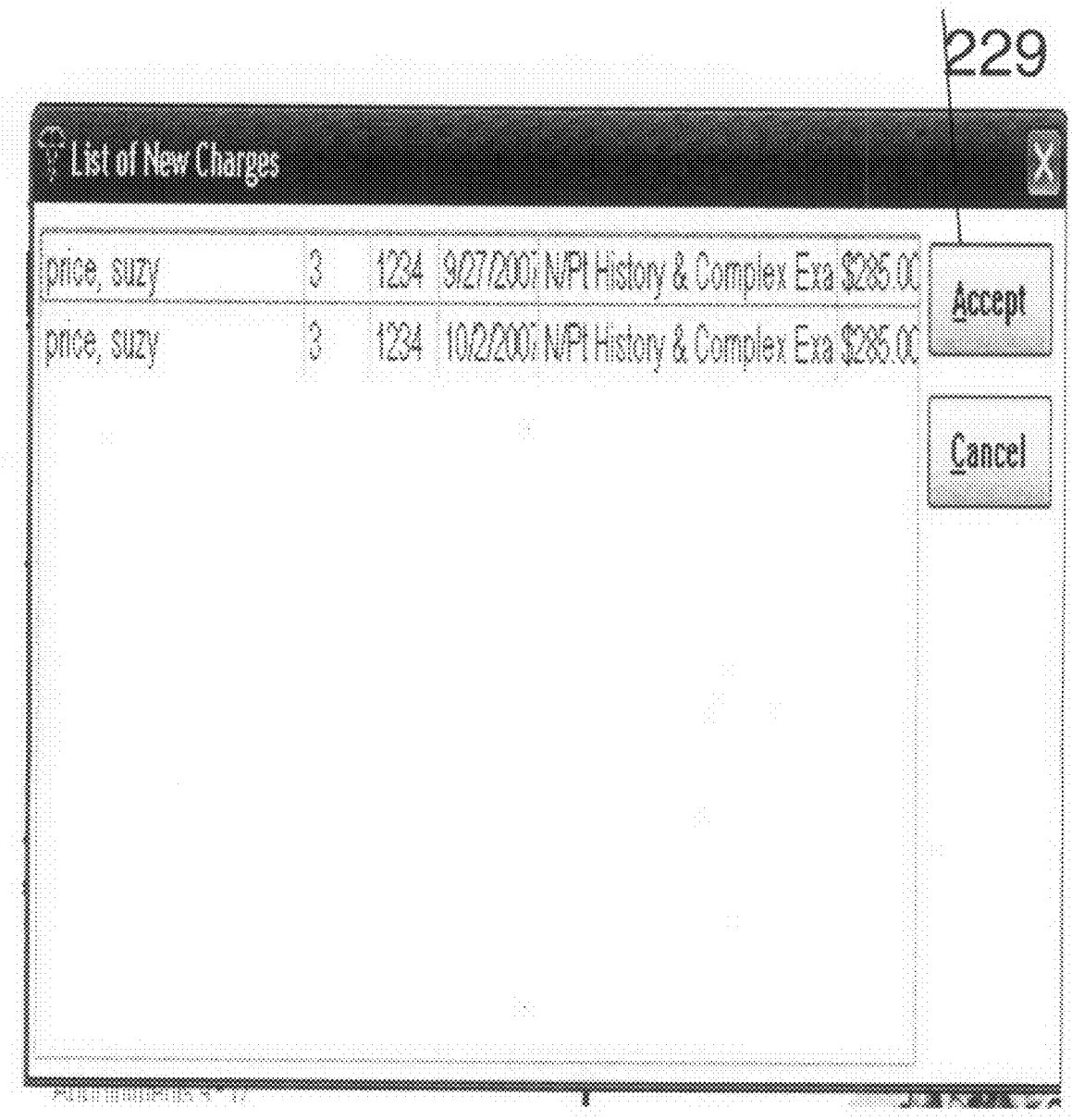
Figure 8:
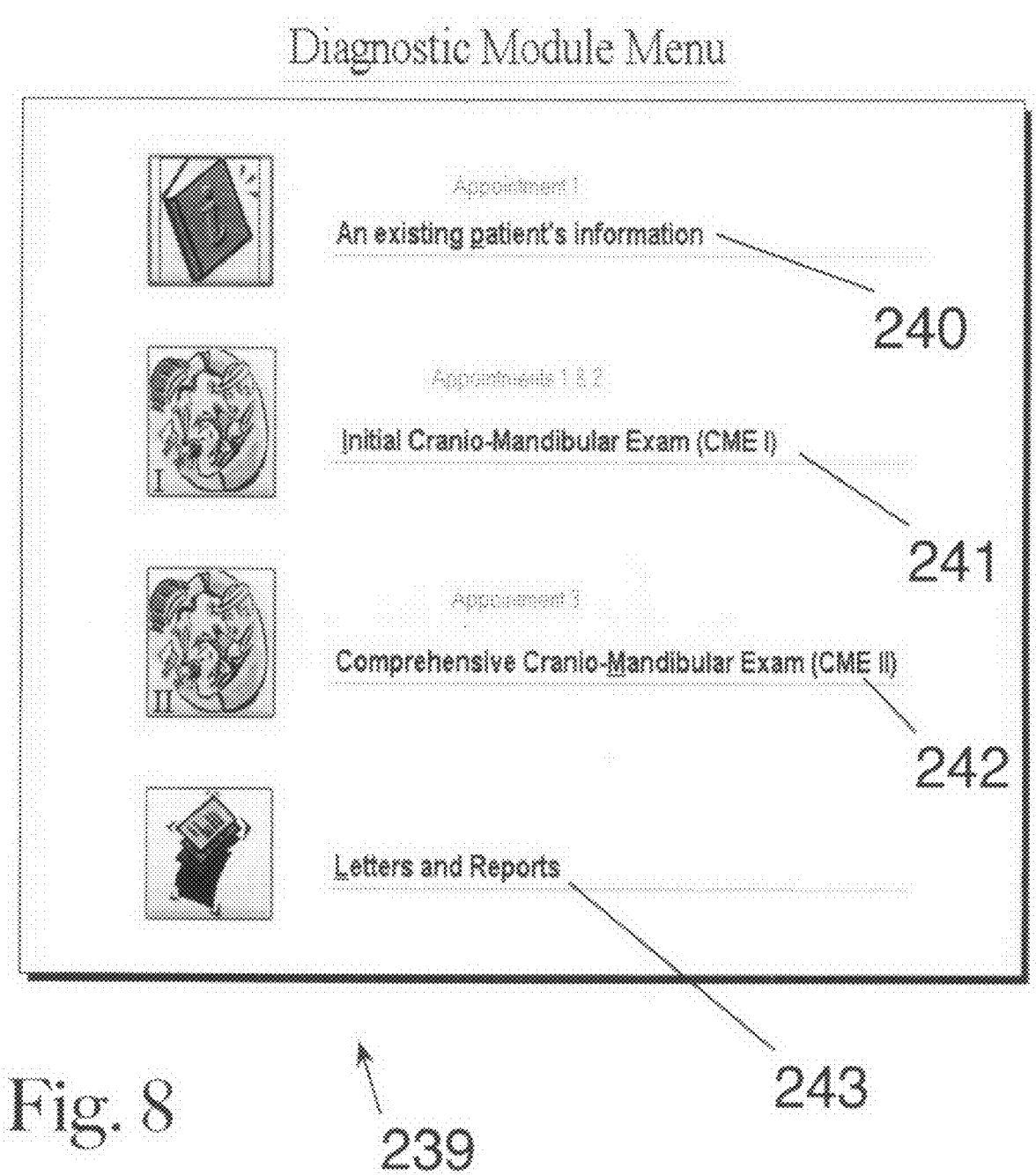
Figure 9A:
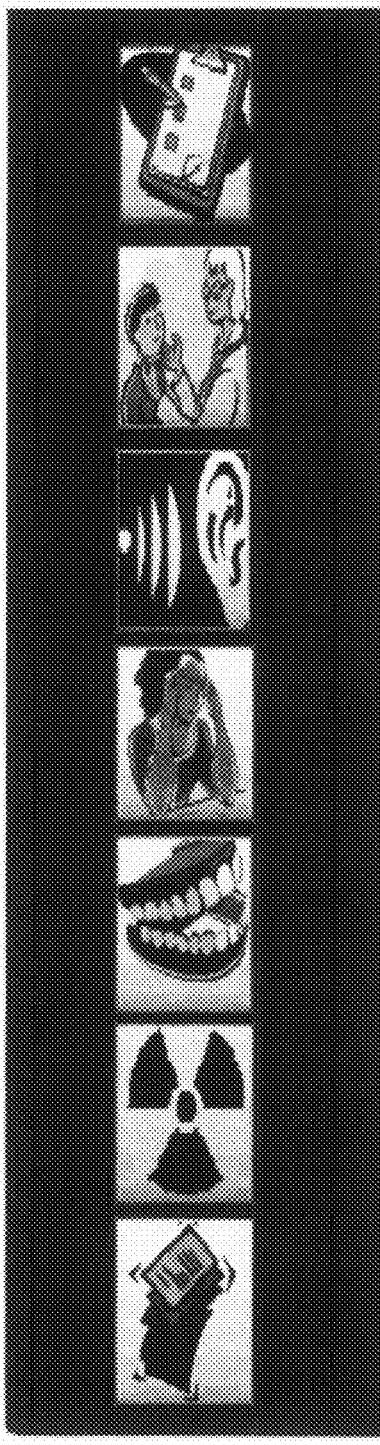
Figure 10A:
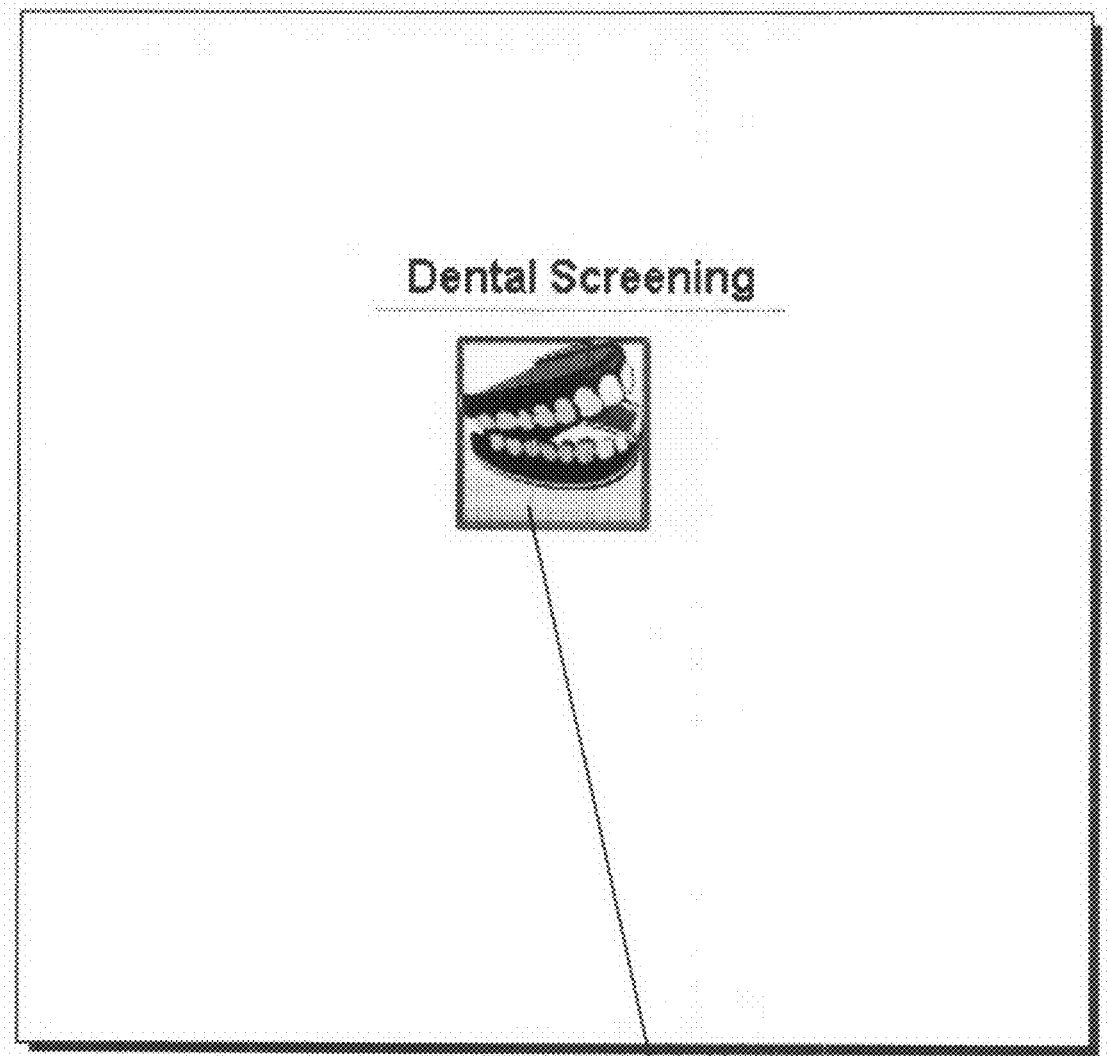
Figure 11A:
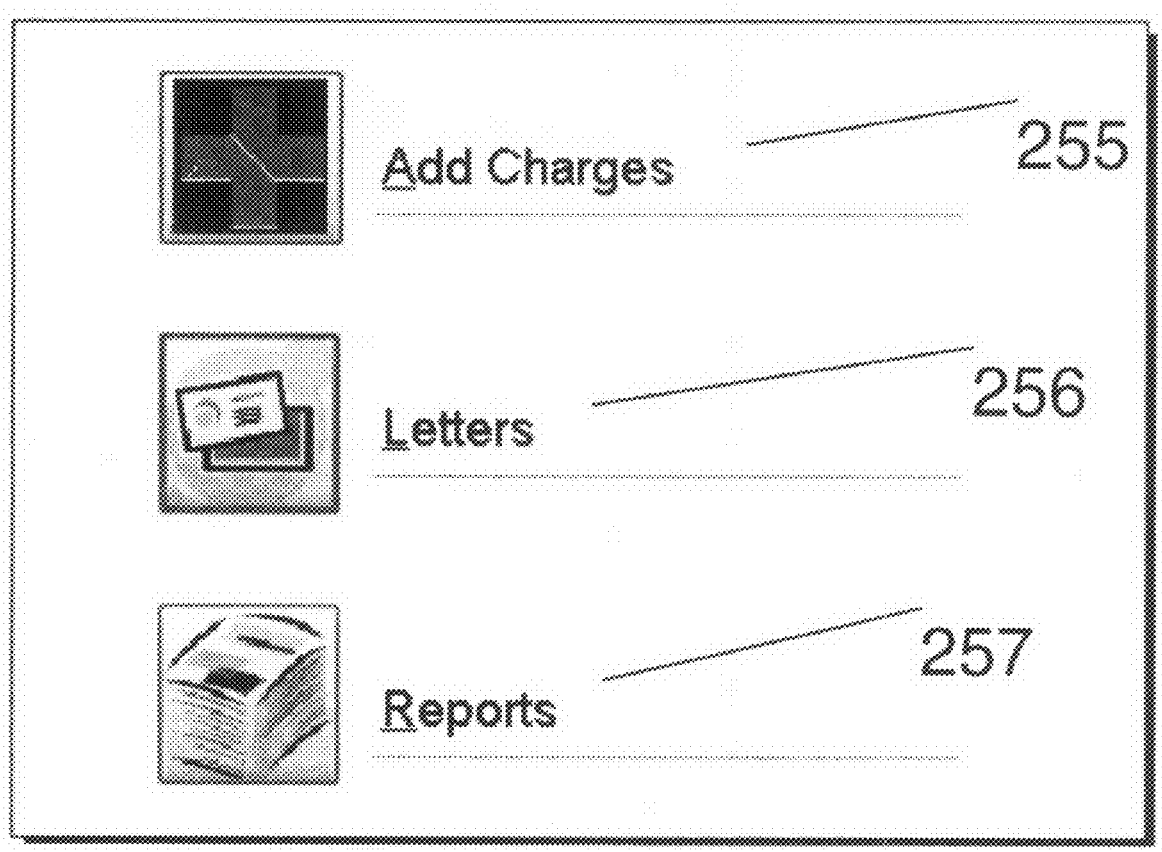
Figure 11B:
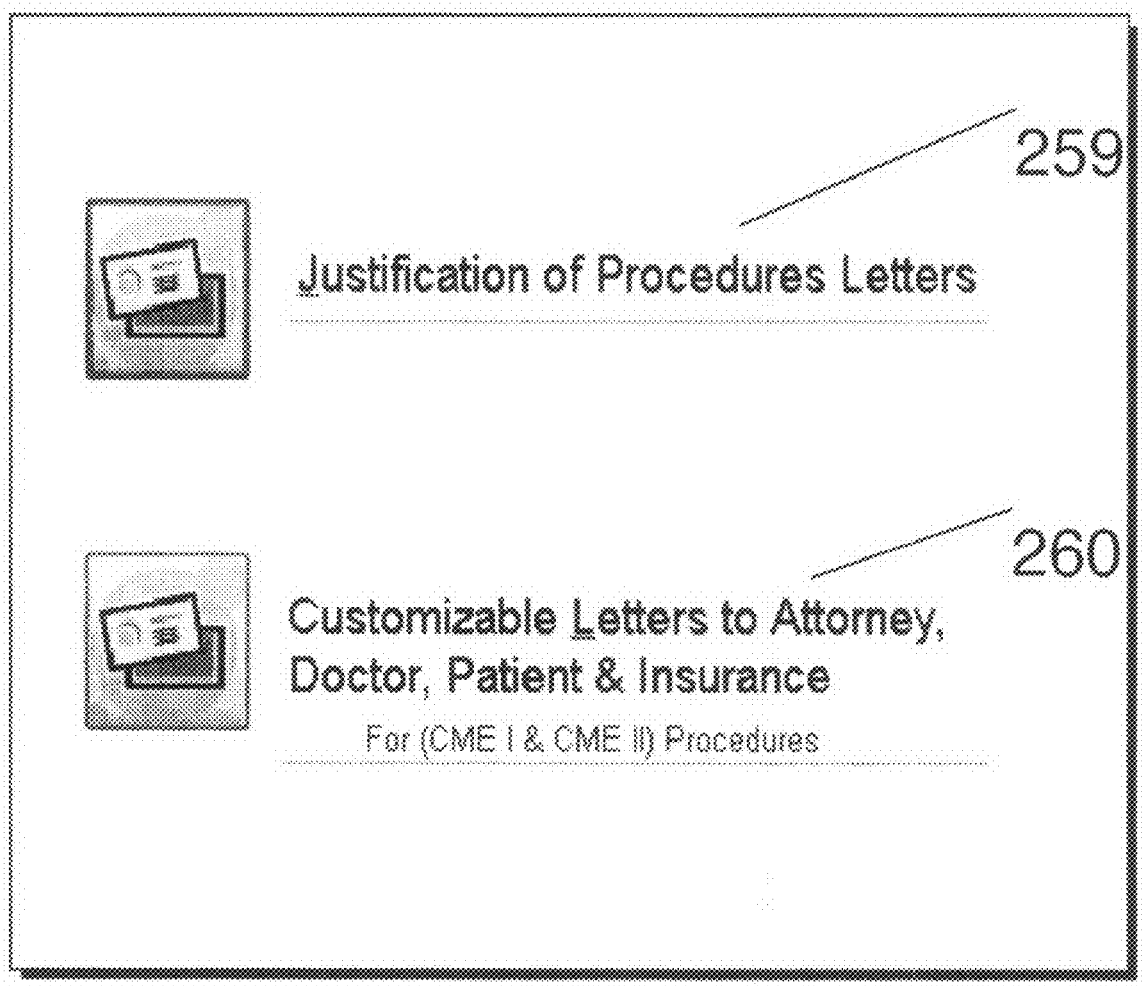
Figure 12A:
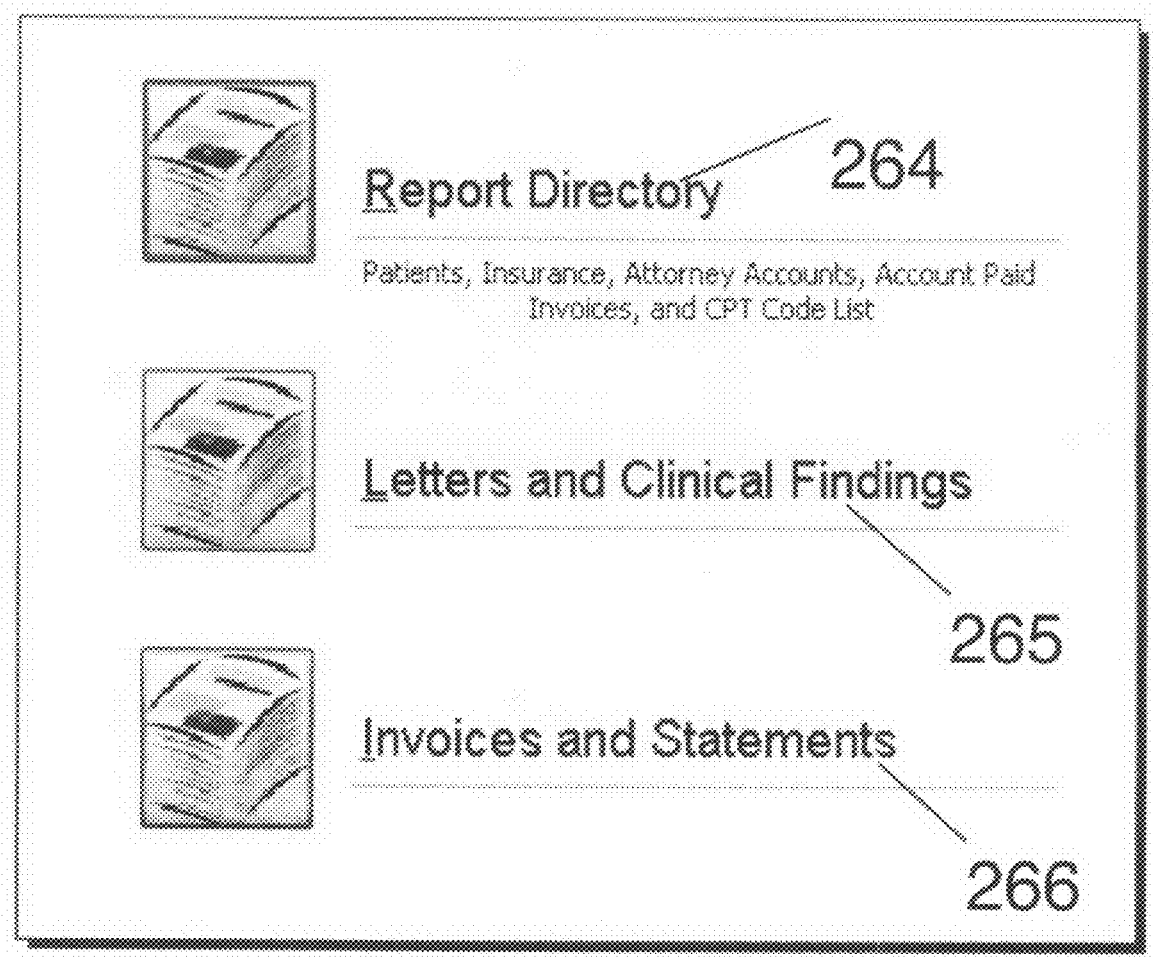
Figure 12B:
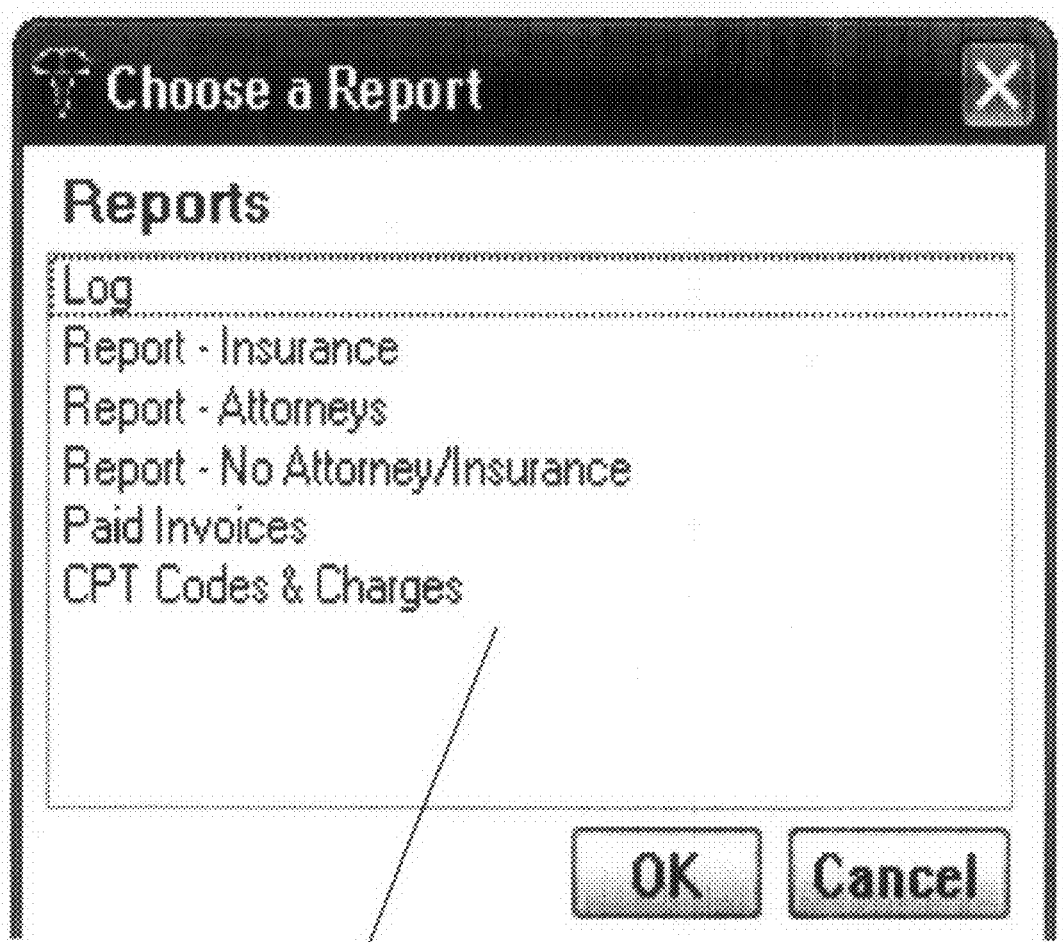
Figure 12C:
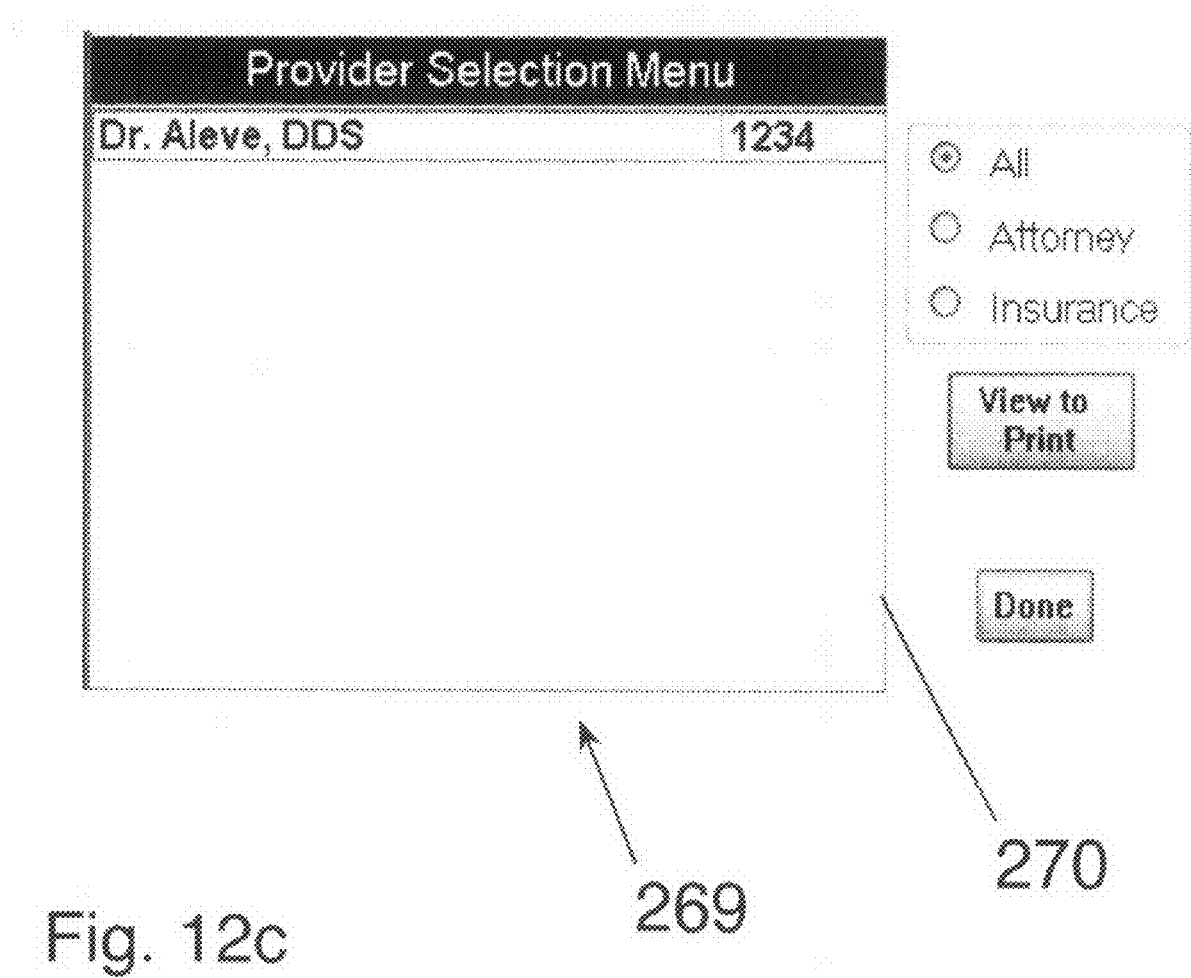
Figure 13:
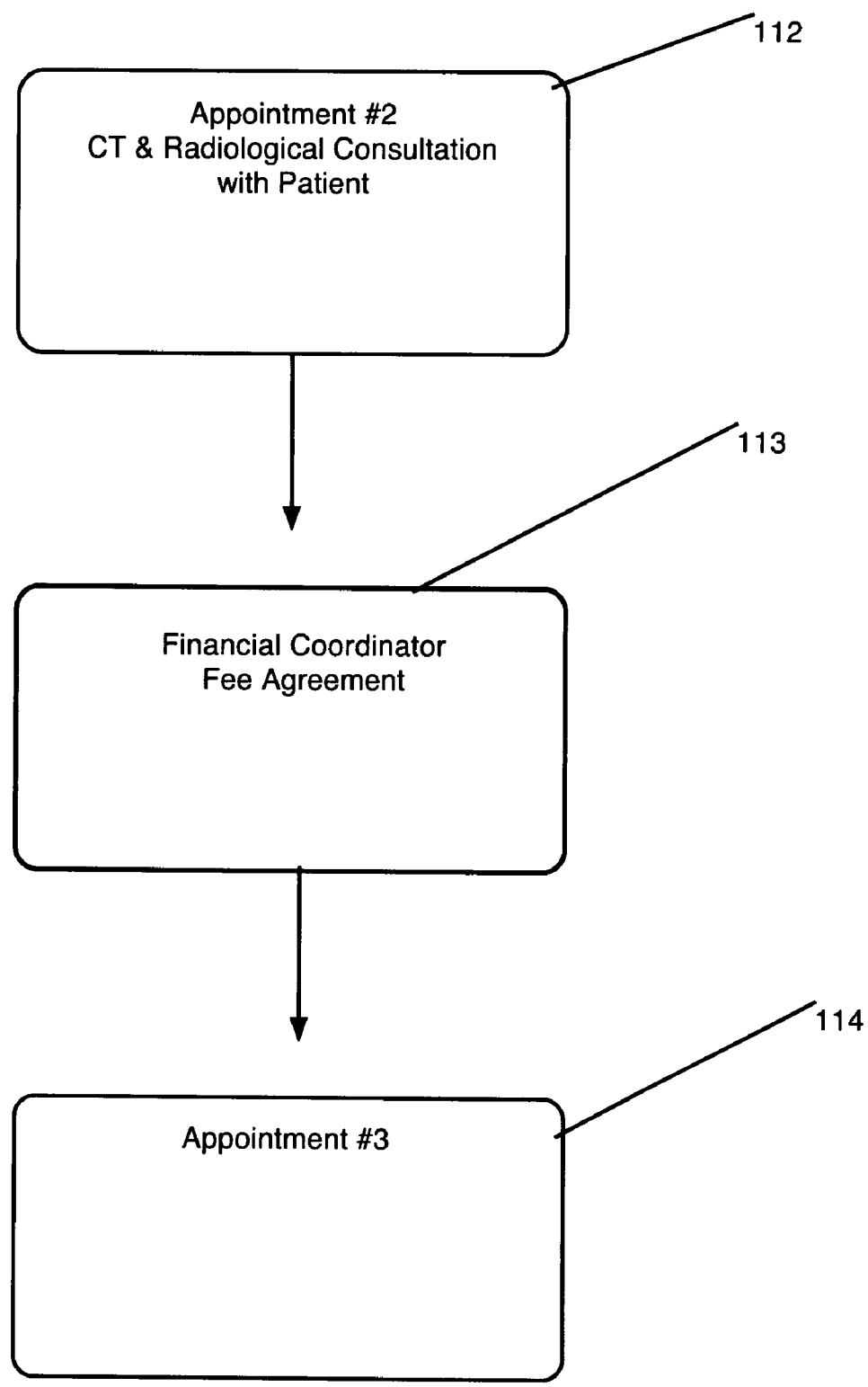
FIG. 13 is a flowchart describing the general method of obtaining, entering and processing of CT and Radiological consultation information for the Second Appointment.
Figure 15:
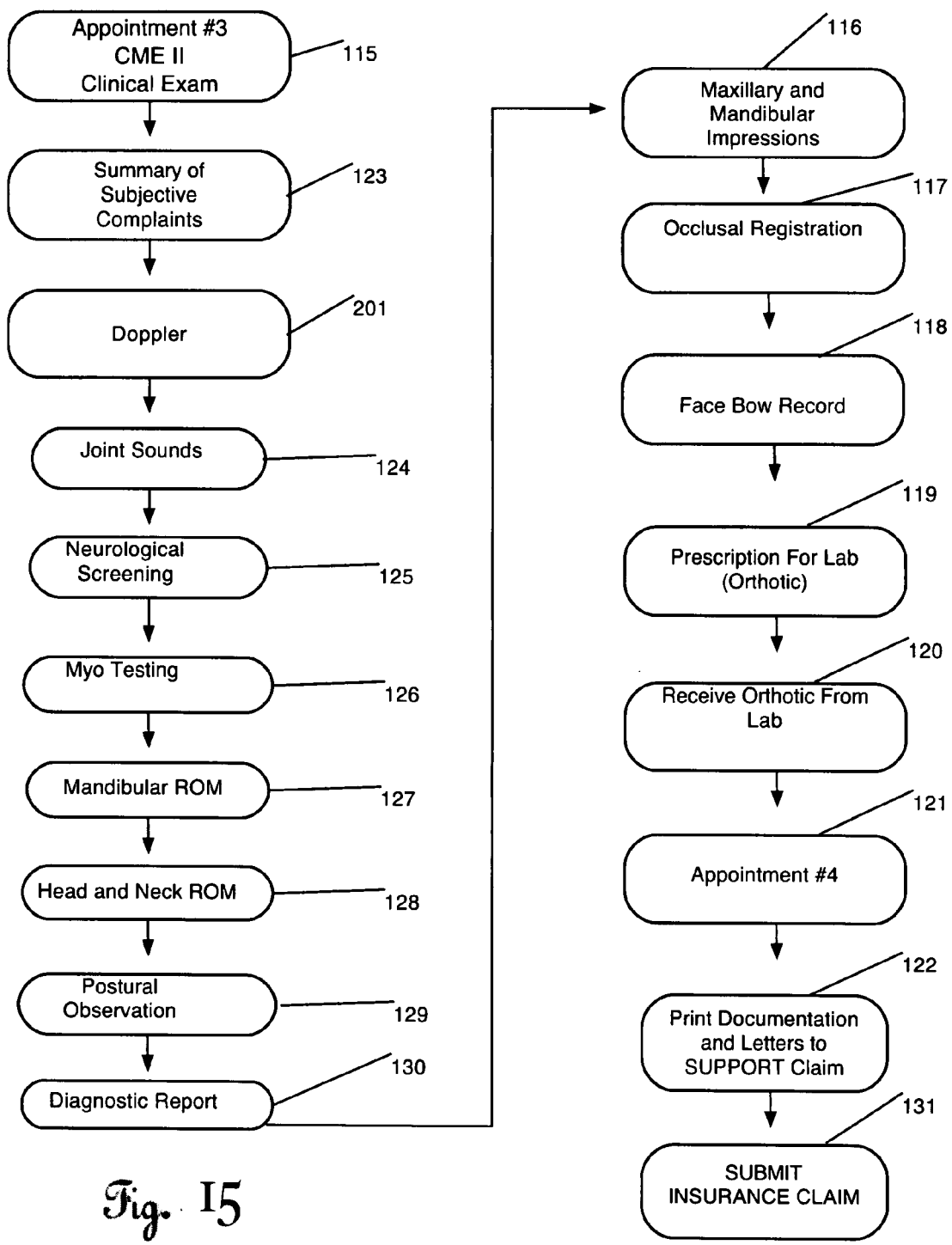
FIG. 15 is a flowchart describing the general method of obtaining, entering and processing clinical examination information, and preparing a customized orthotic treatment device for the Third Appointment.
Figure 16A:
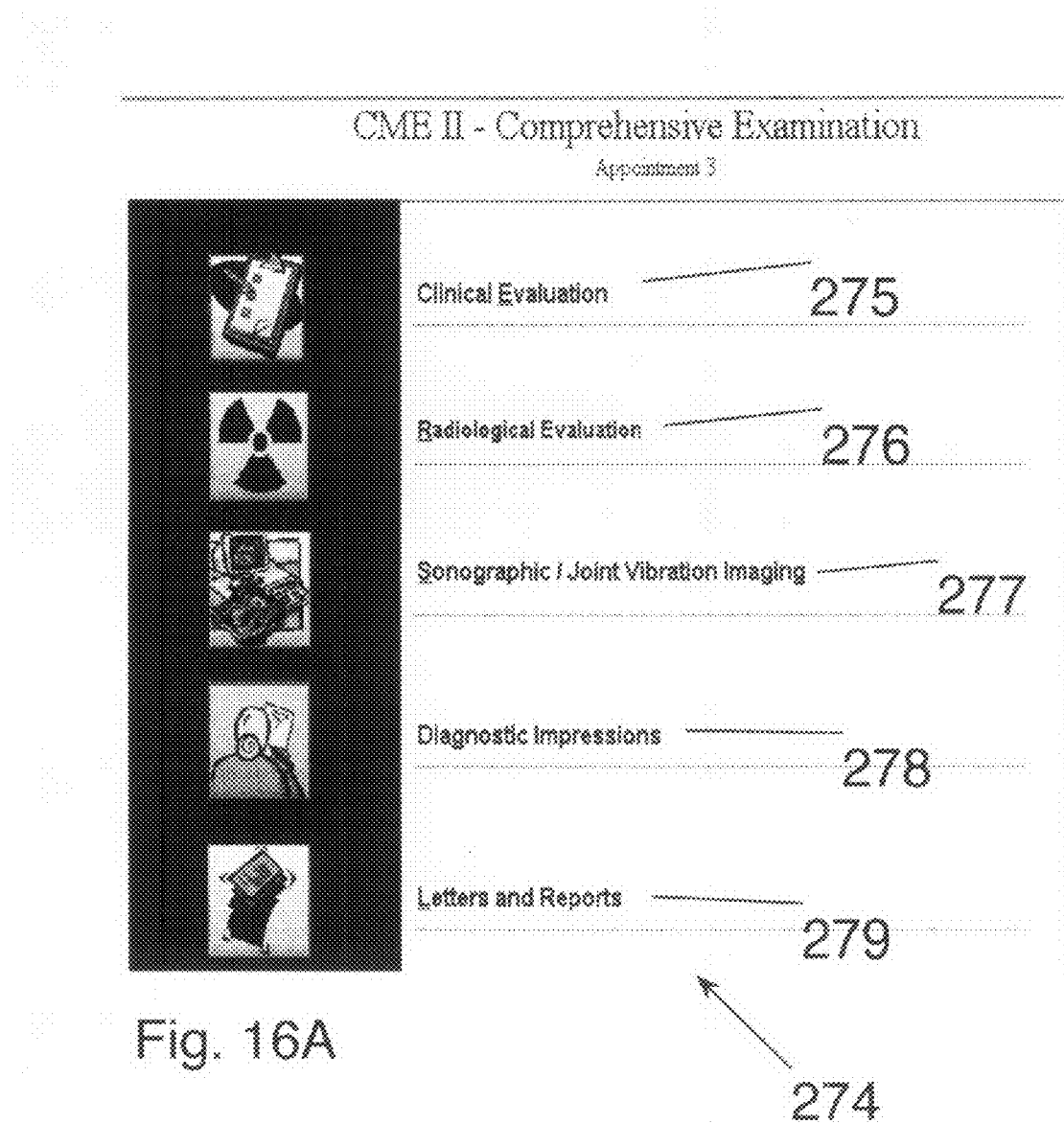
Figure 18A:
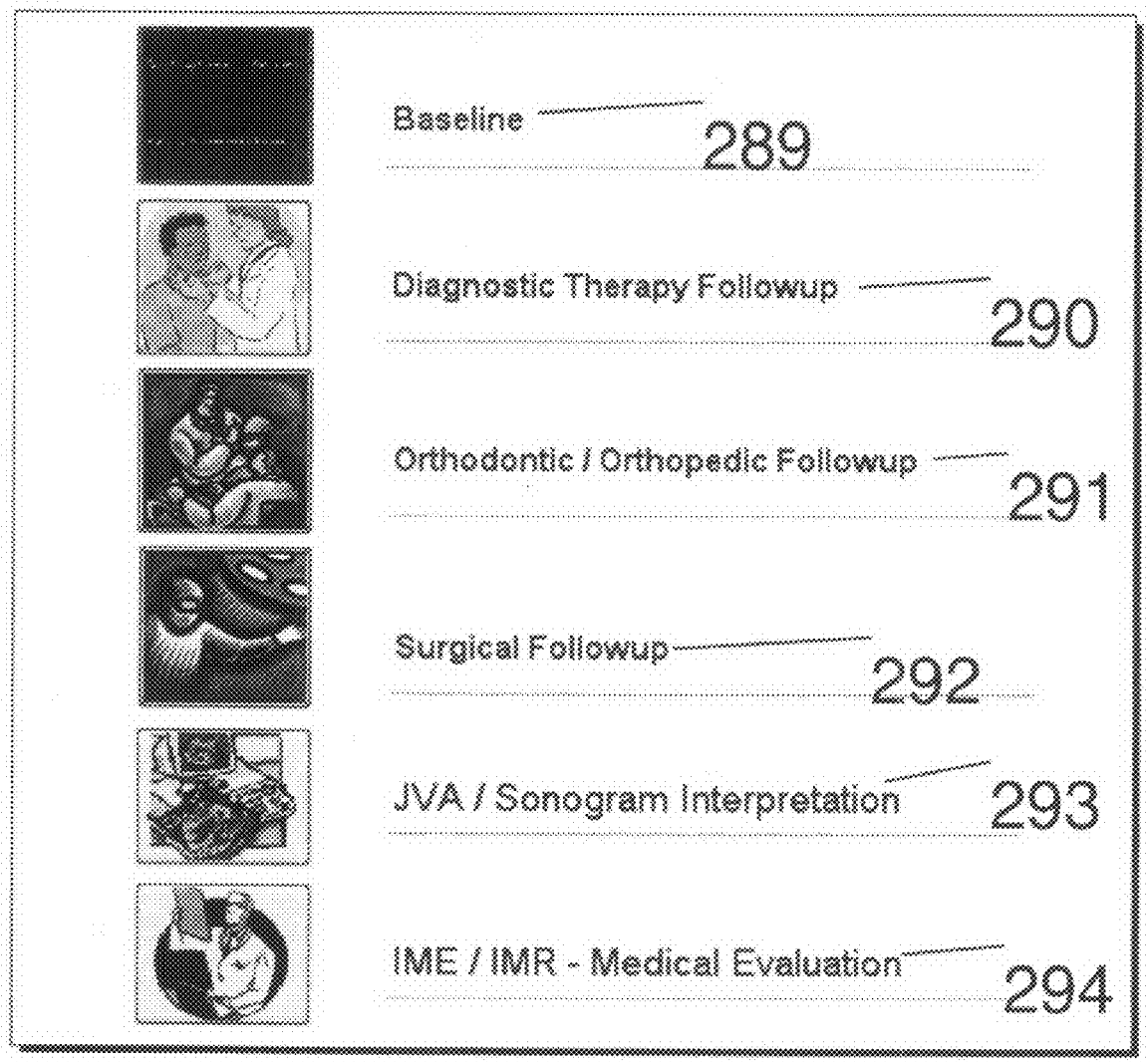
Figure 18B:
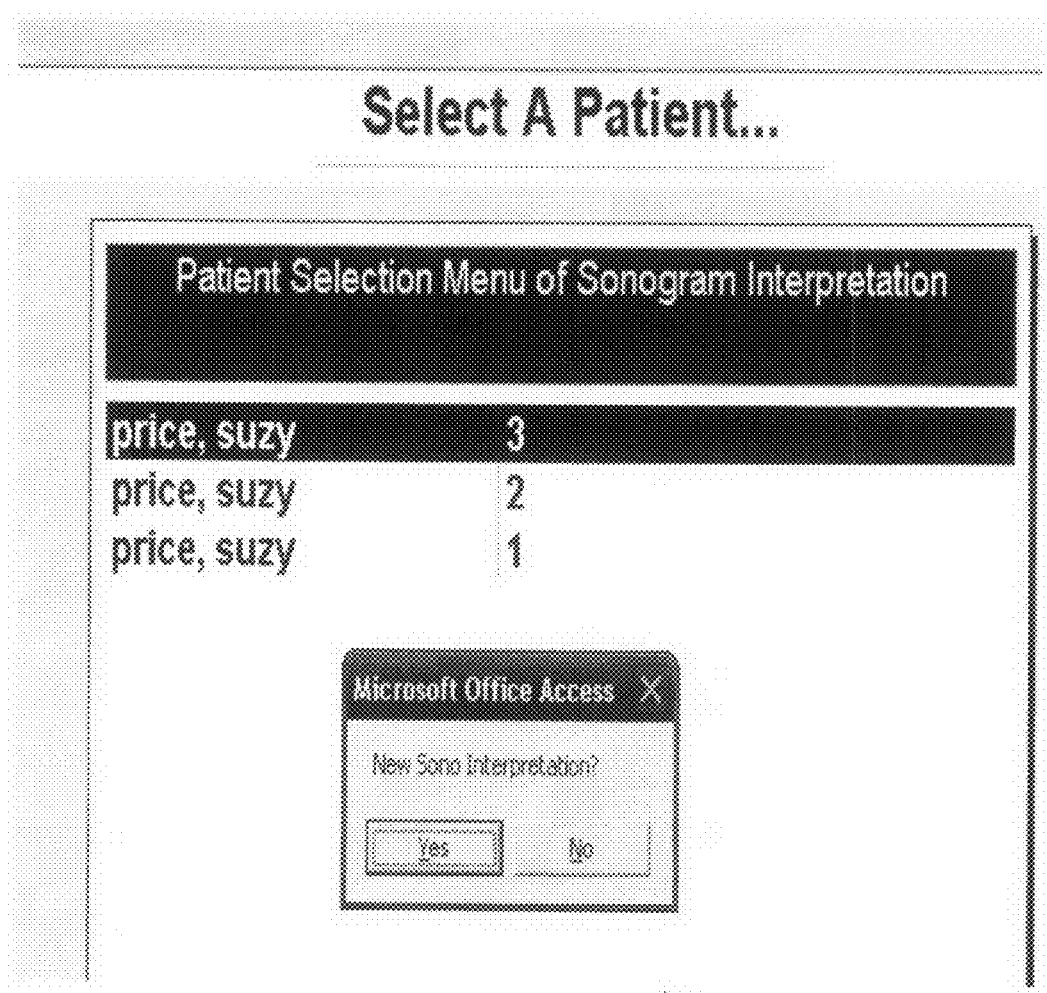
Figure 18D:
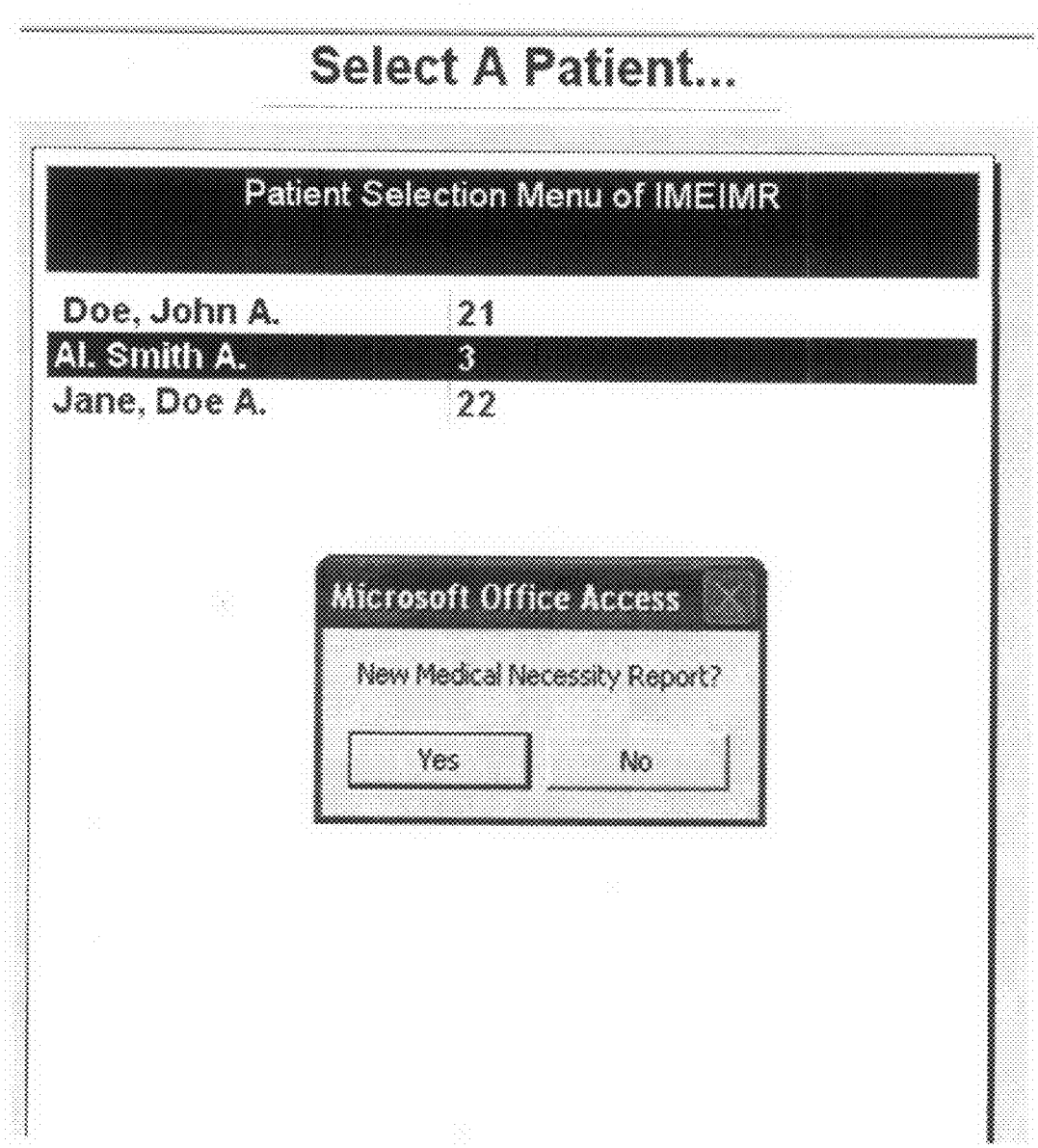
Figure 20:
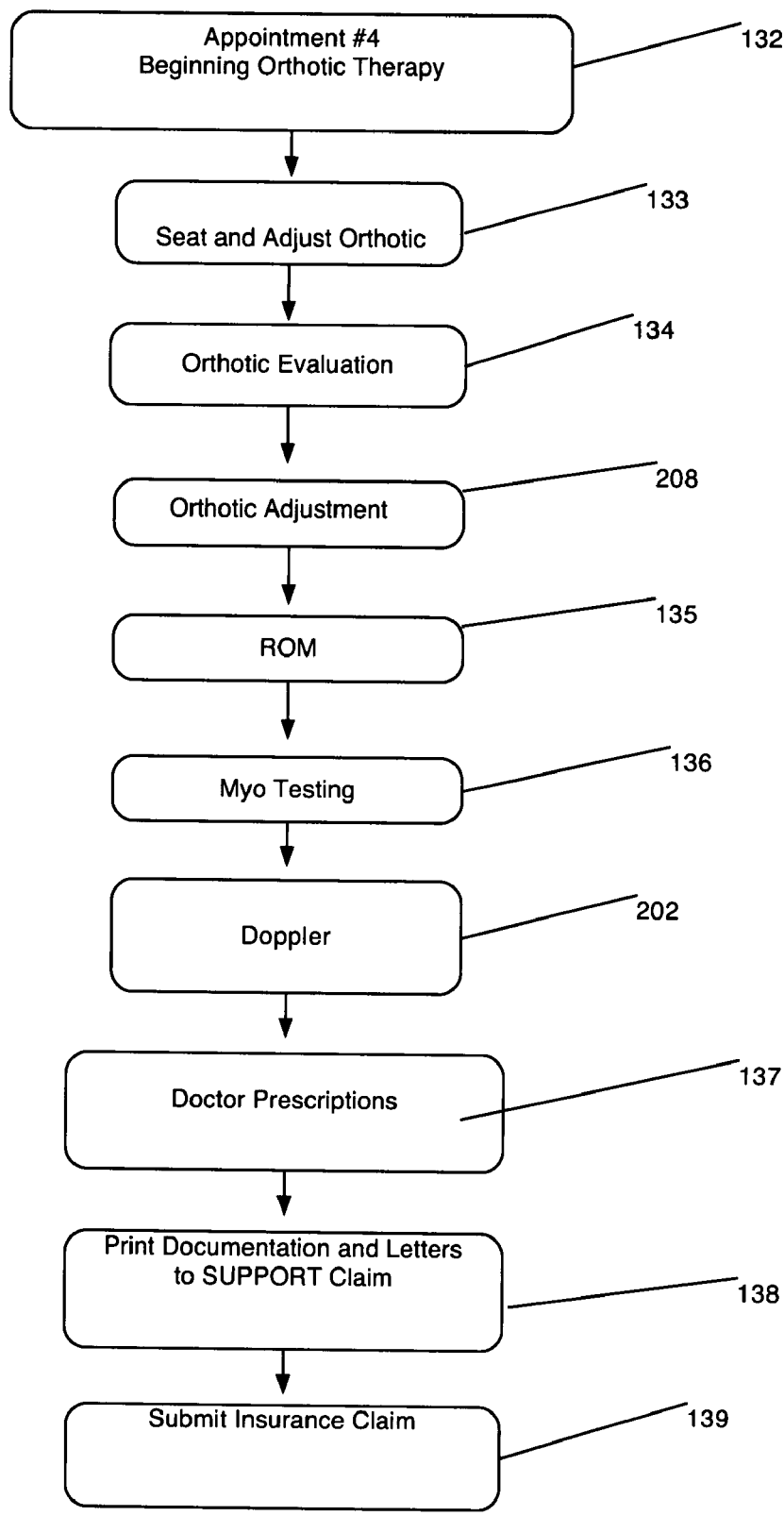
FIG. 20 is a flowchart describing the general method of obtaining, entering and processing information for the beginning of orthotic therapy for the Fourth Appointment.
Figure 21A:
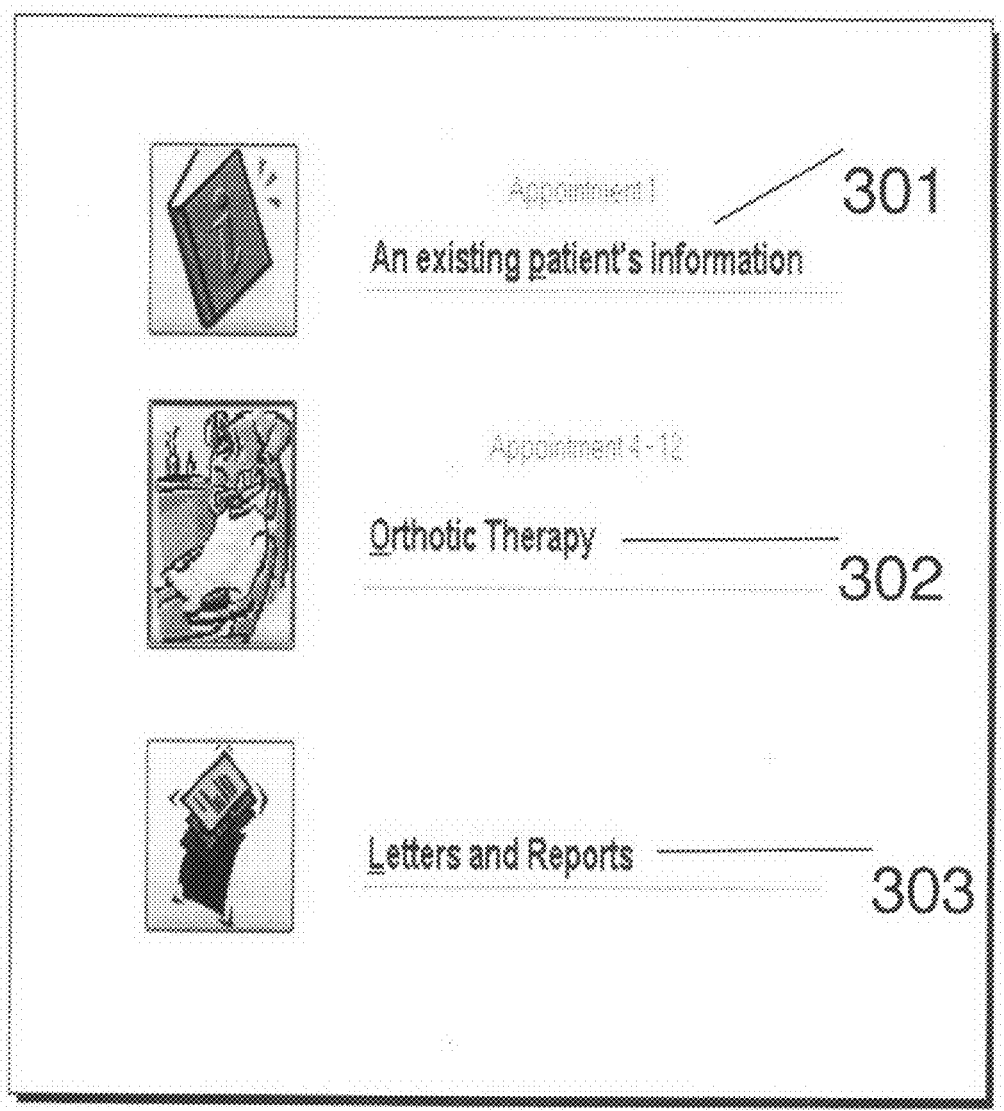
Figure 21B:
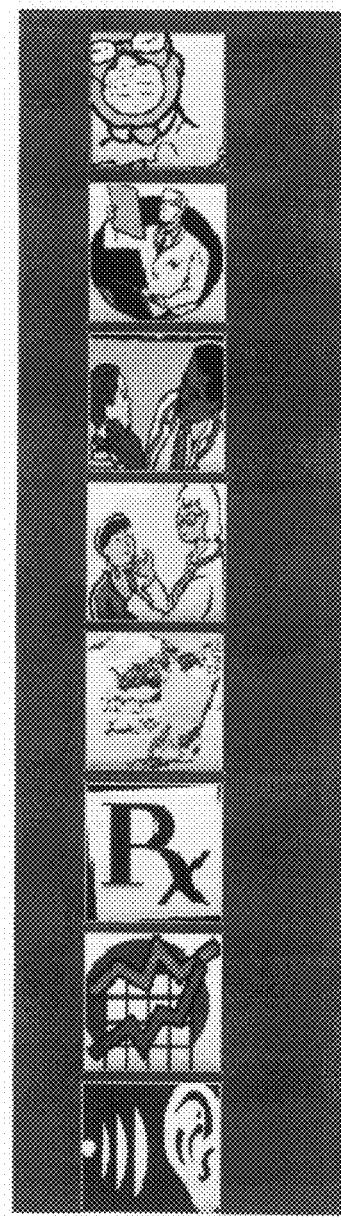
Figure 21C:
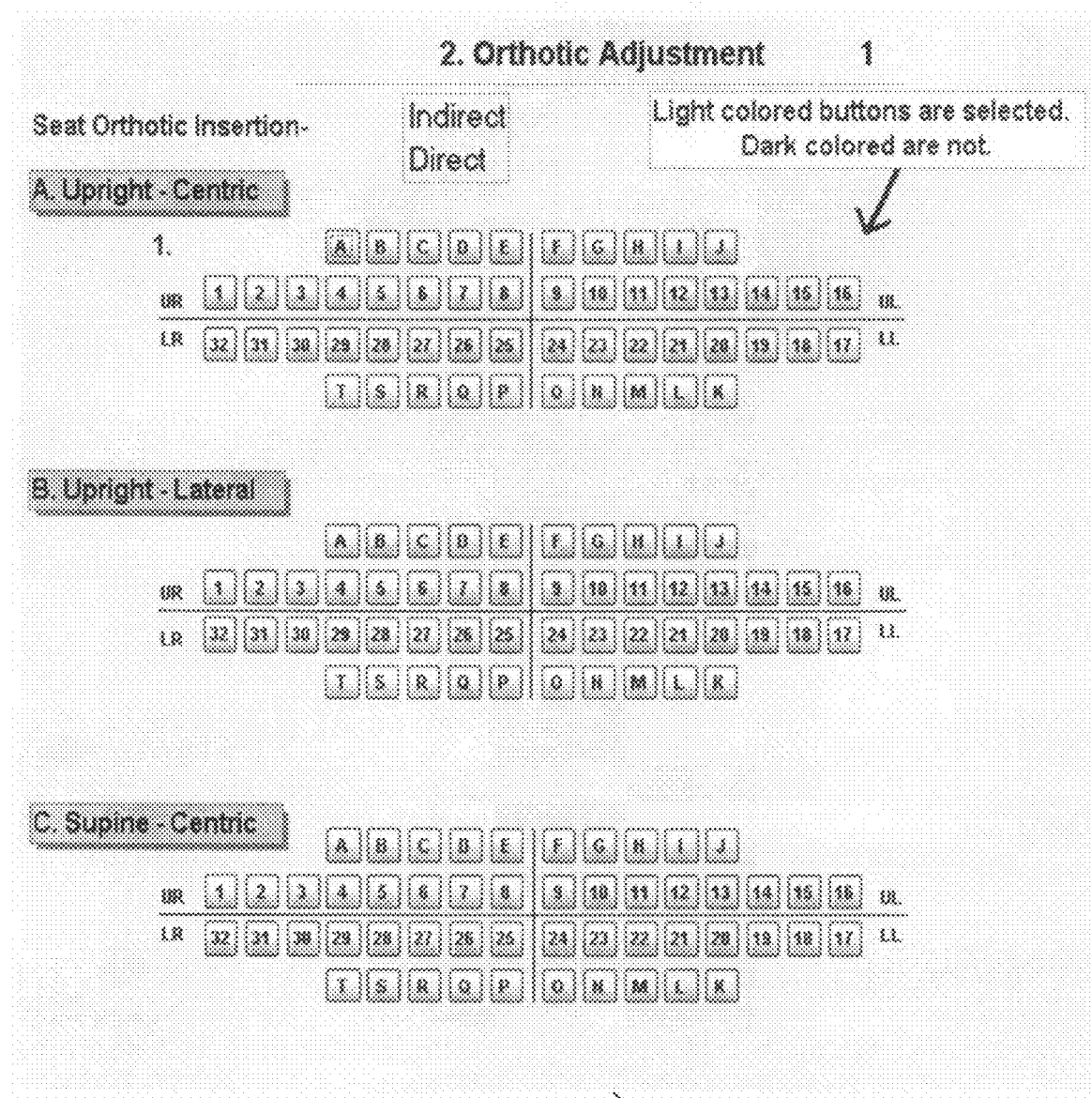
Figure 22A:
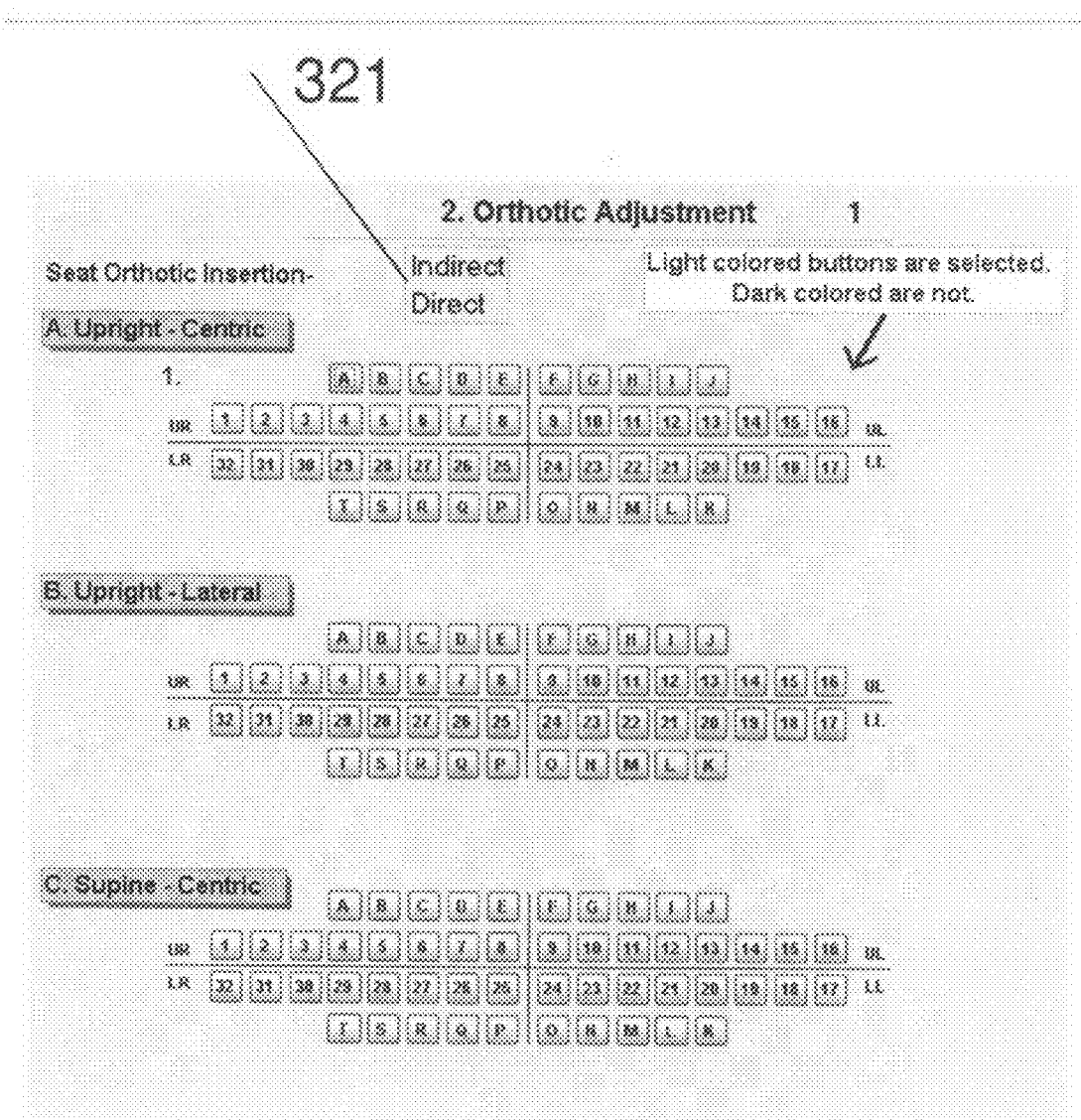
Figure 24:
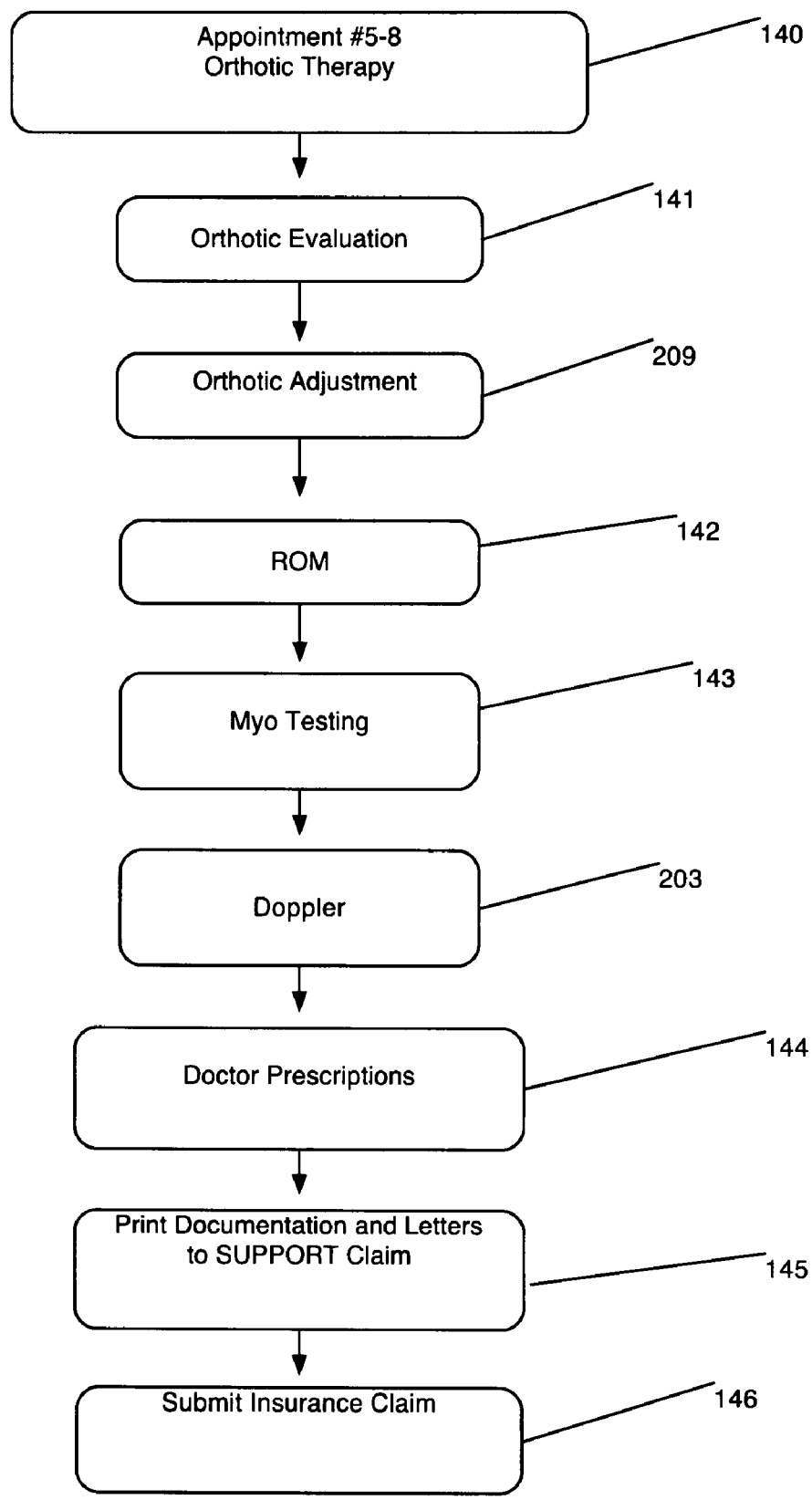
FIG. 24 is a flowchart describing the general method of obtaining, entering and processing information for continuing orthotic therapy information for the Fifth through Eighth Appointments.
Figure 25:
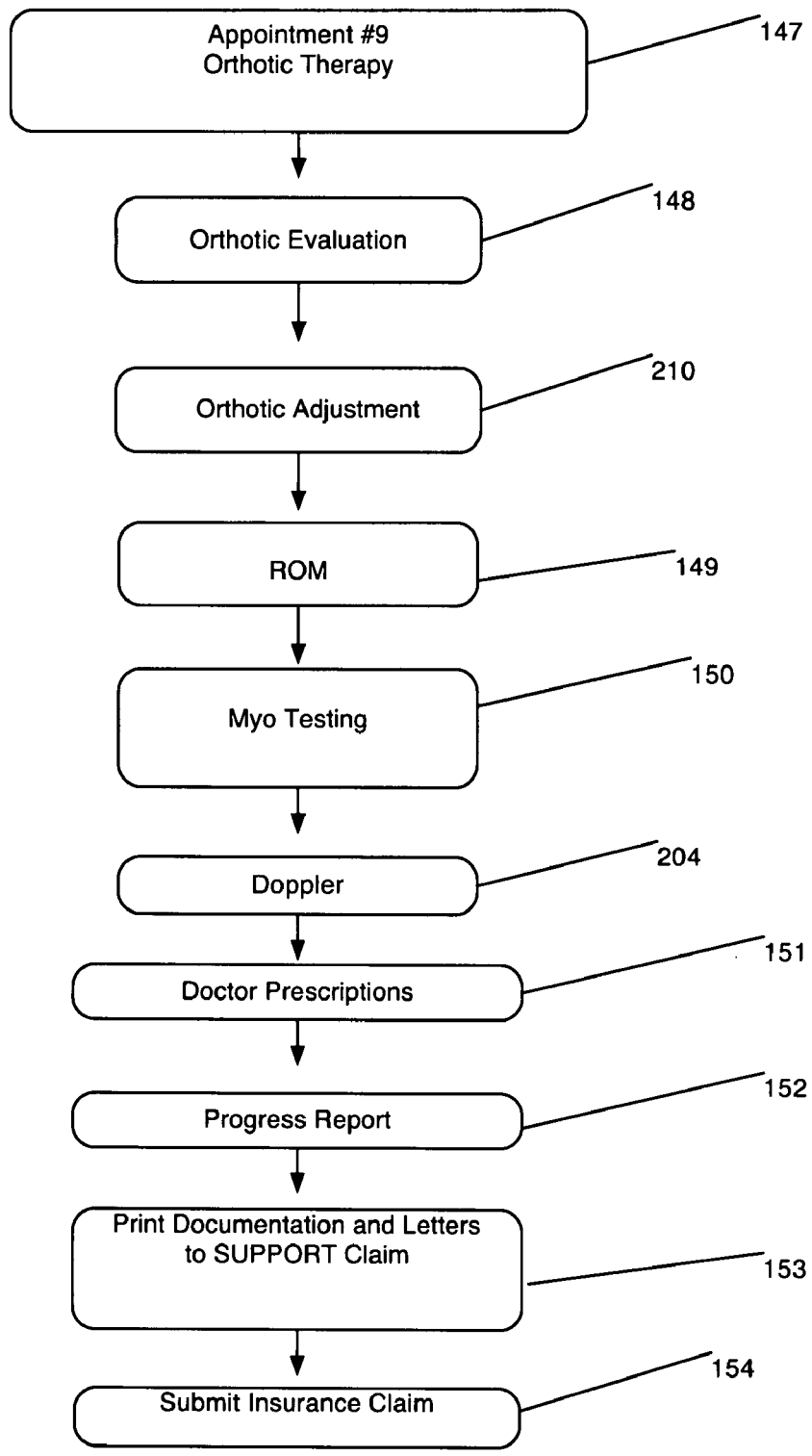
FIG. 25 is a flowchart describing the general method of obtaining, entering and processing information for continuing orthotic therapy information for the Ninth Appointment.
Figure 26:
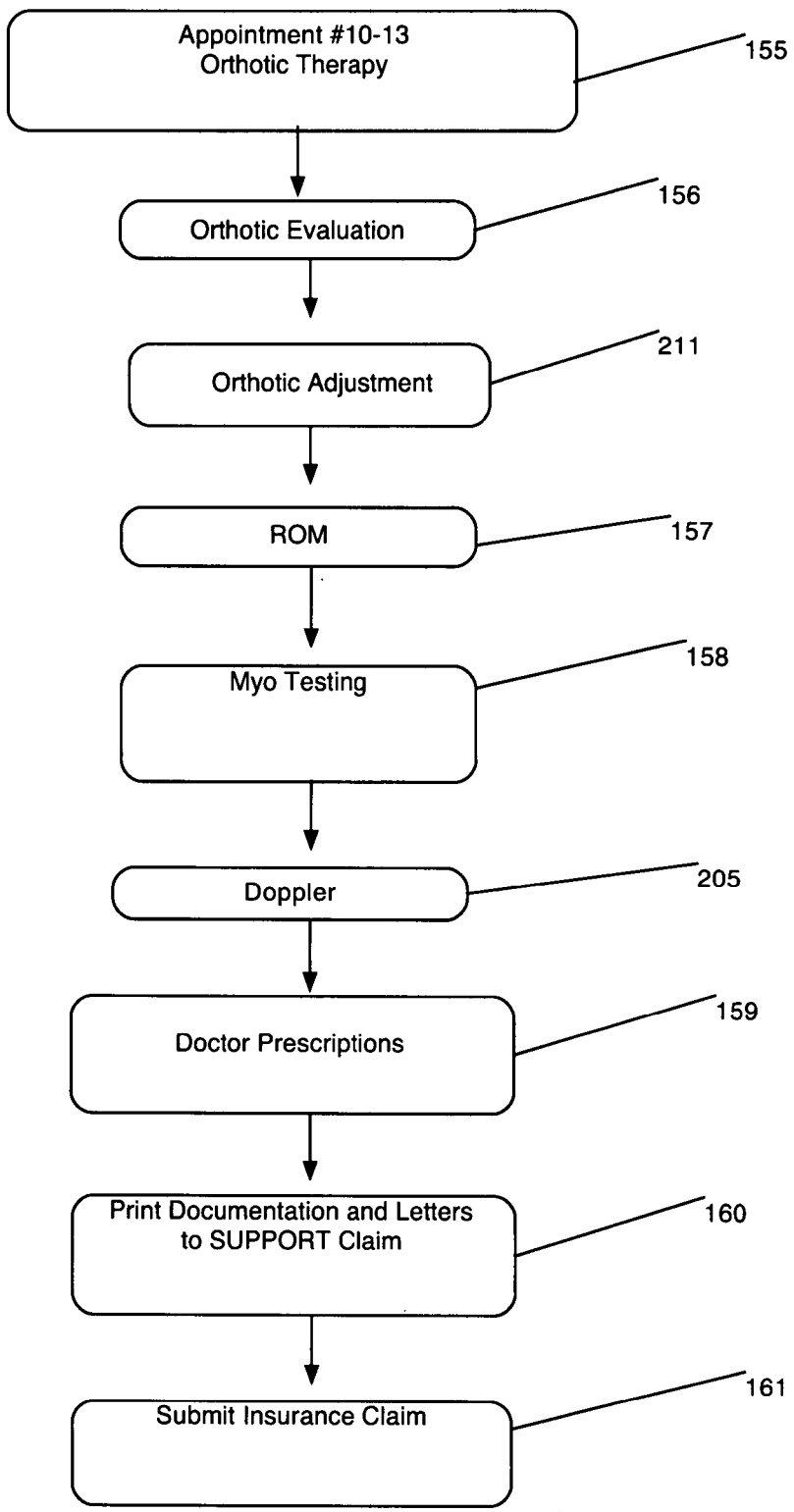
FIG. 26 is a flowchart describing the general method of obtaining, entering and processing information for continuing orthotic therapy information for the Tenth through Thirteenth Appointments.
Figure 27:
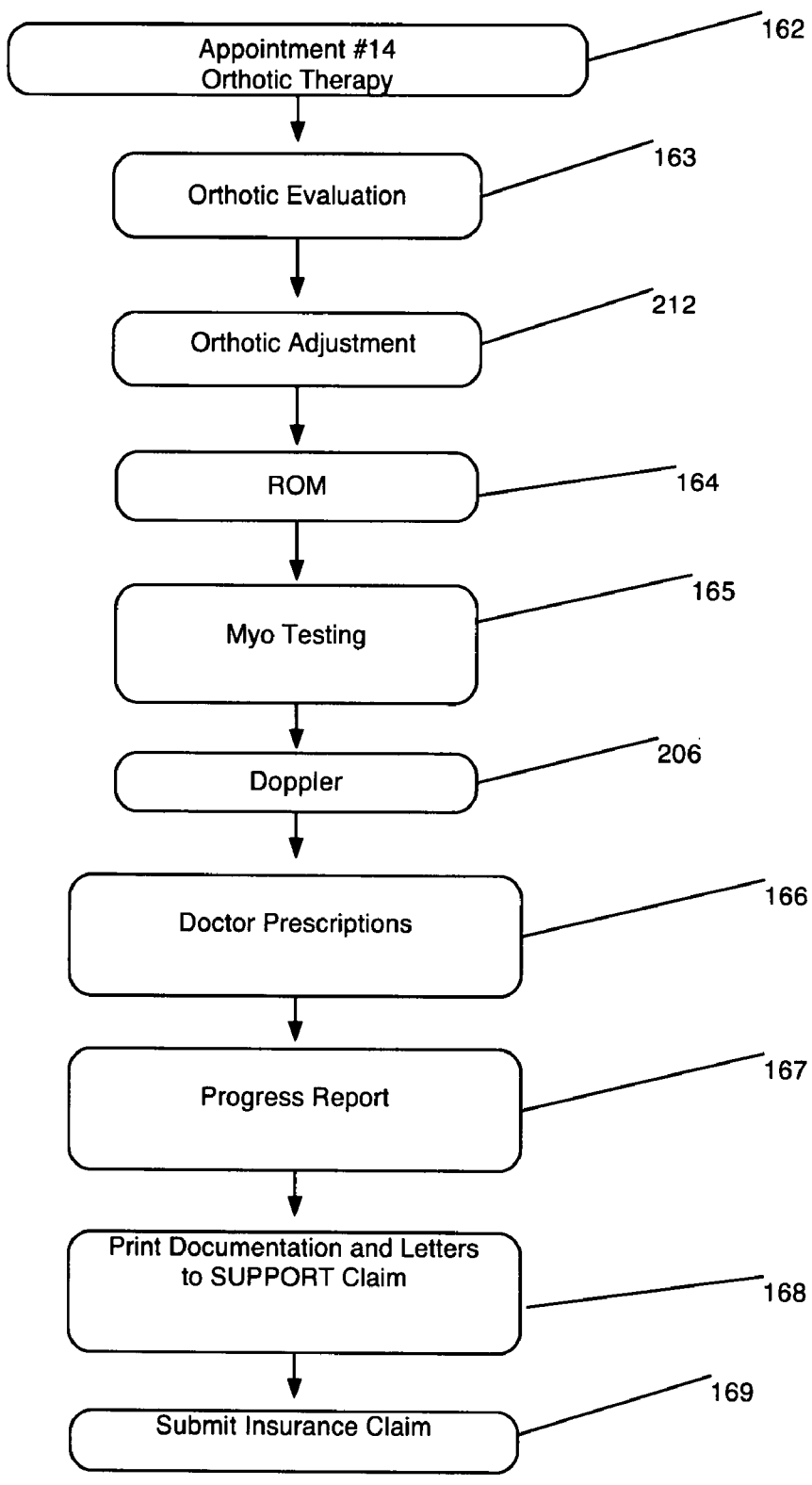
FIG. 27 is a flowchart describing the general method of obtaining, entering and processing information for continuing orthotic therapy information for the Fourteenth Appointment.
Figure 28:
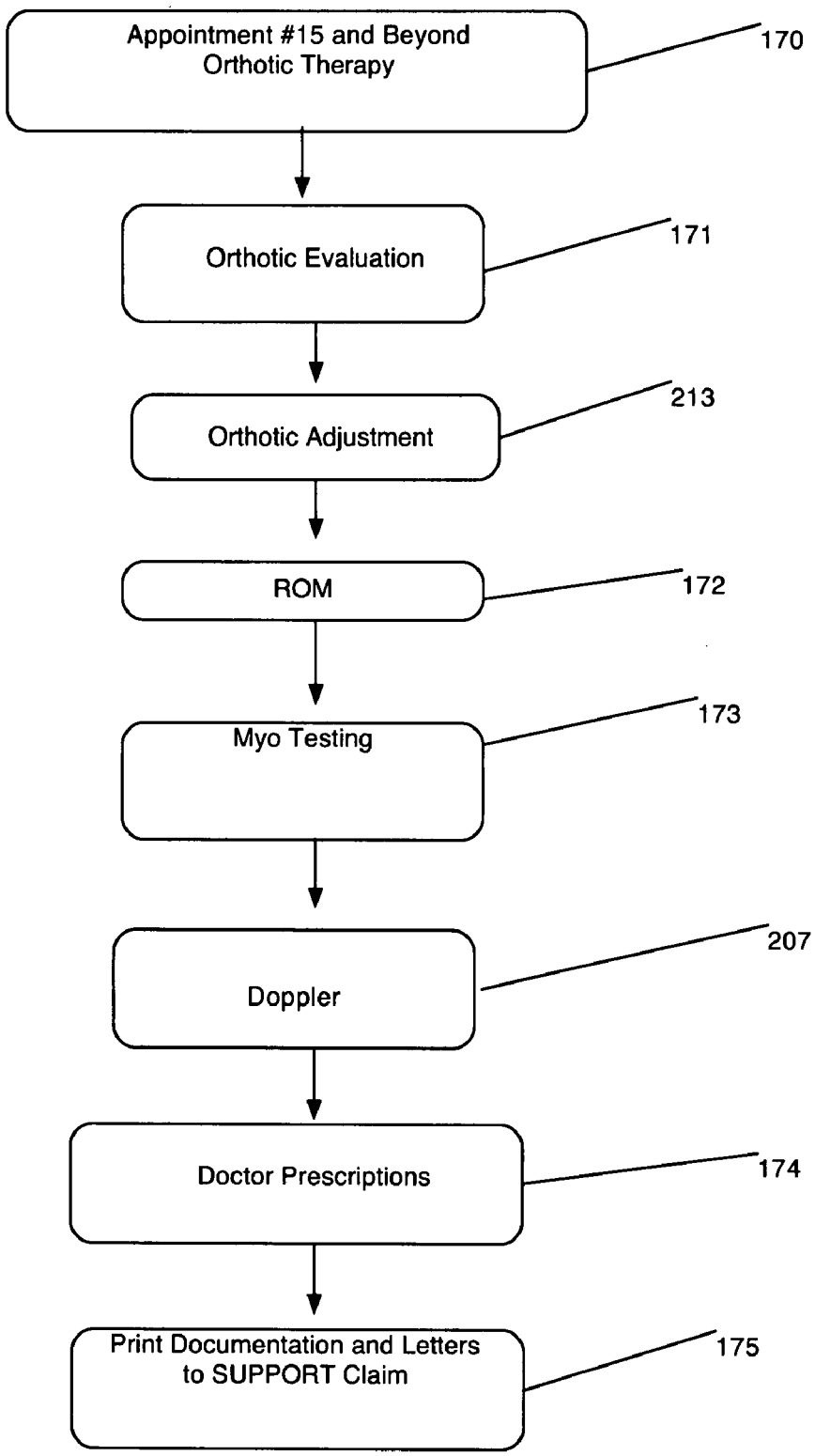
FIG. 28 is a flowchart describing the general method of obtaining, entering and processing information for continuing orthotic therapy information for the Fifteenth Appointment and beyond.
Figure 29:
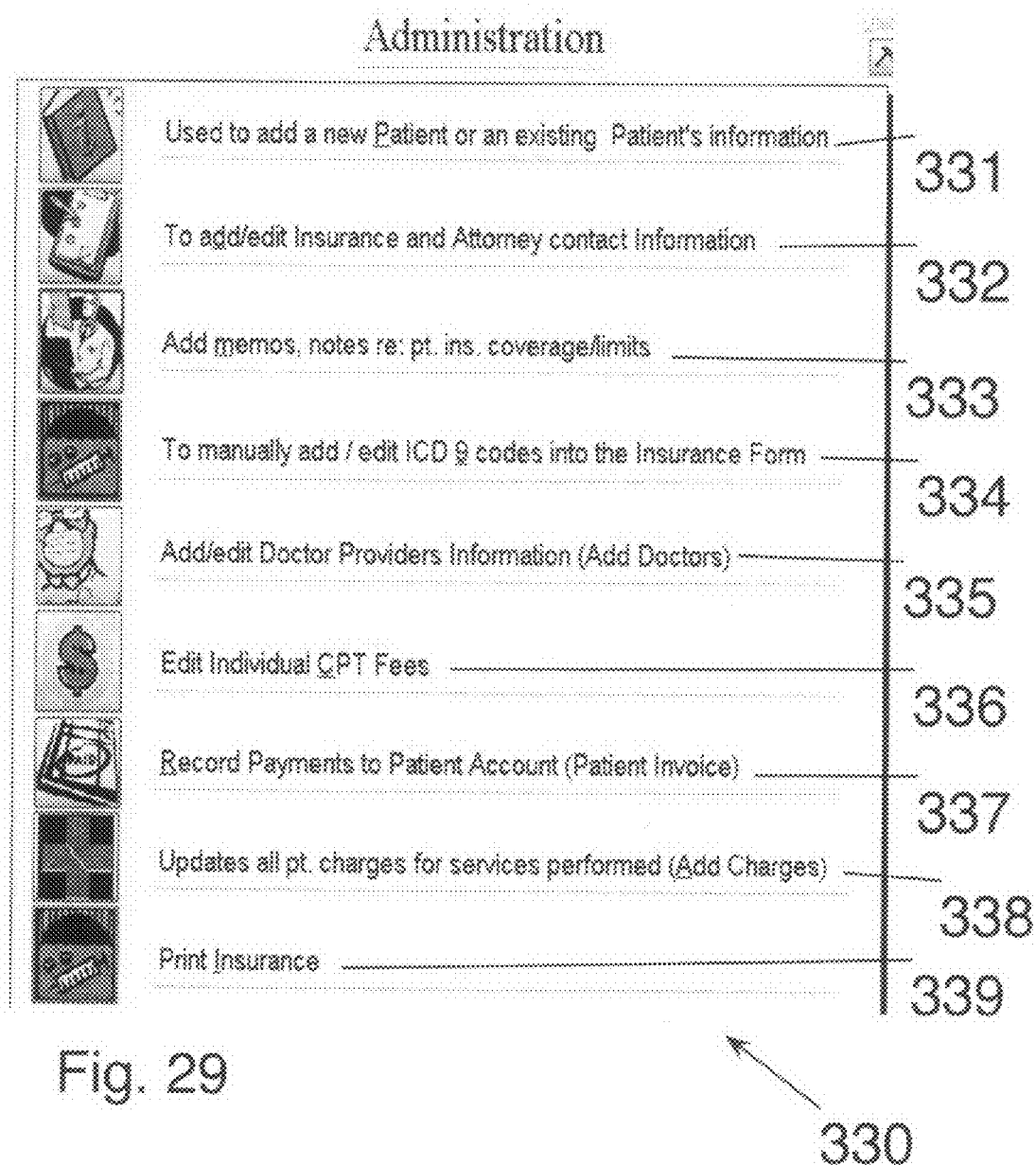
Figure 32A:
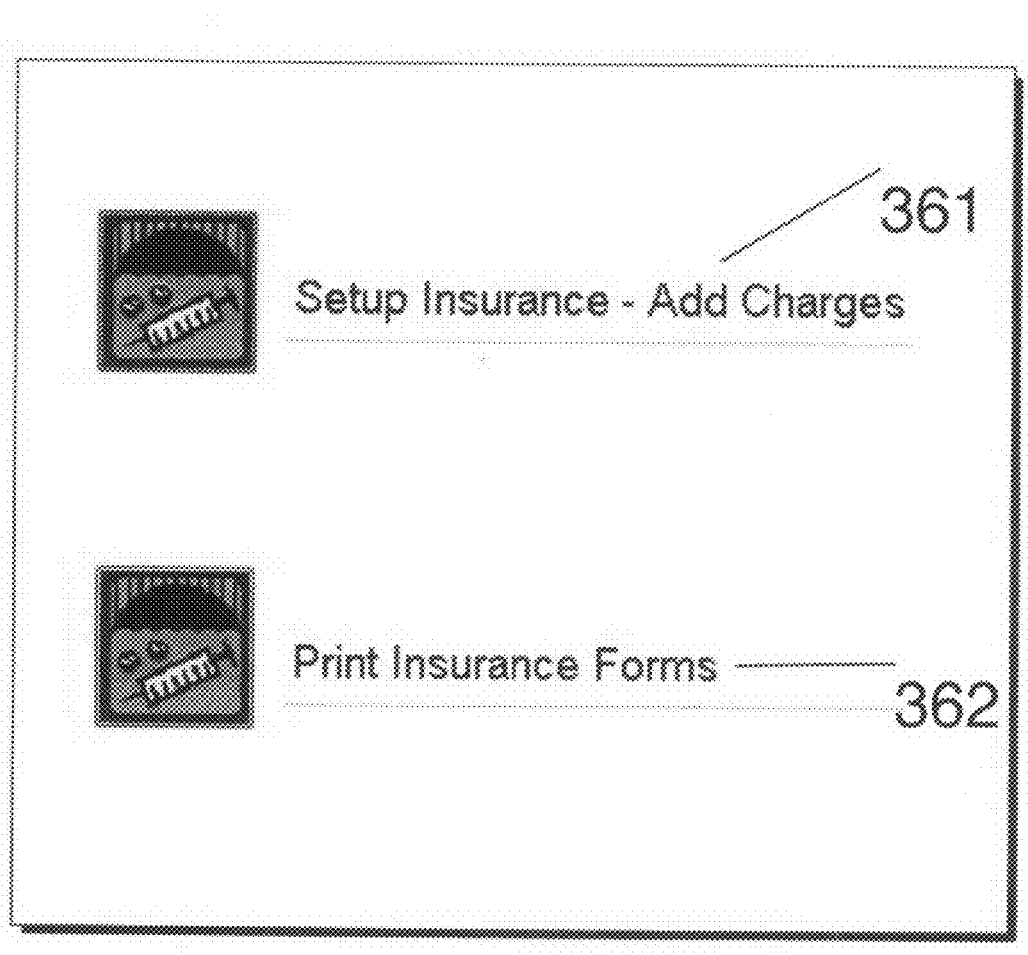
Figure 32C:
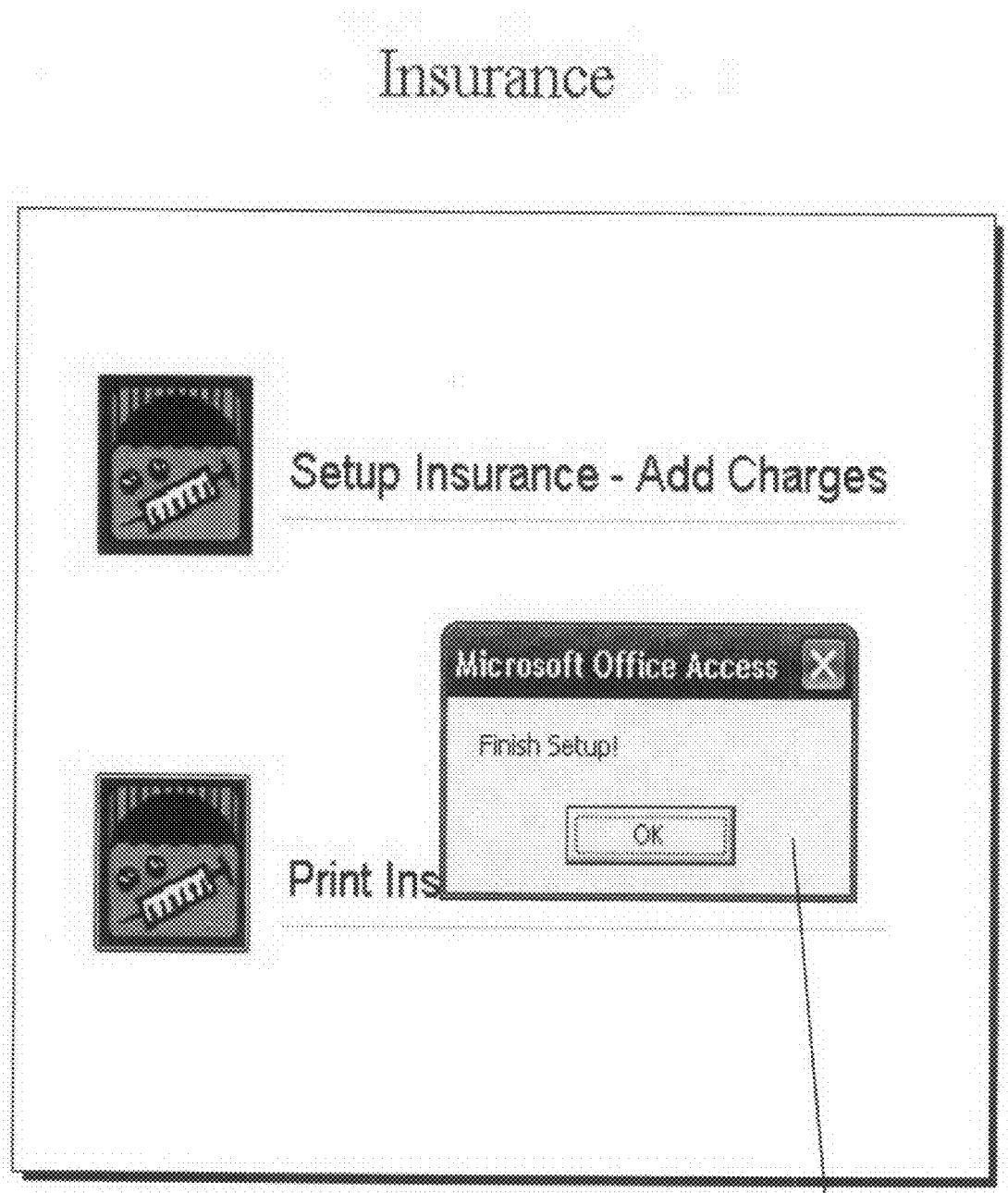
Figure 34A:
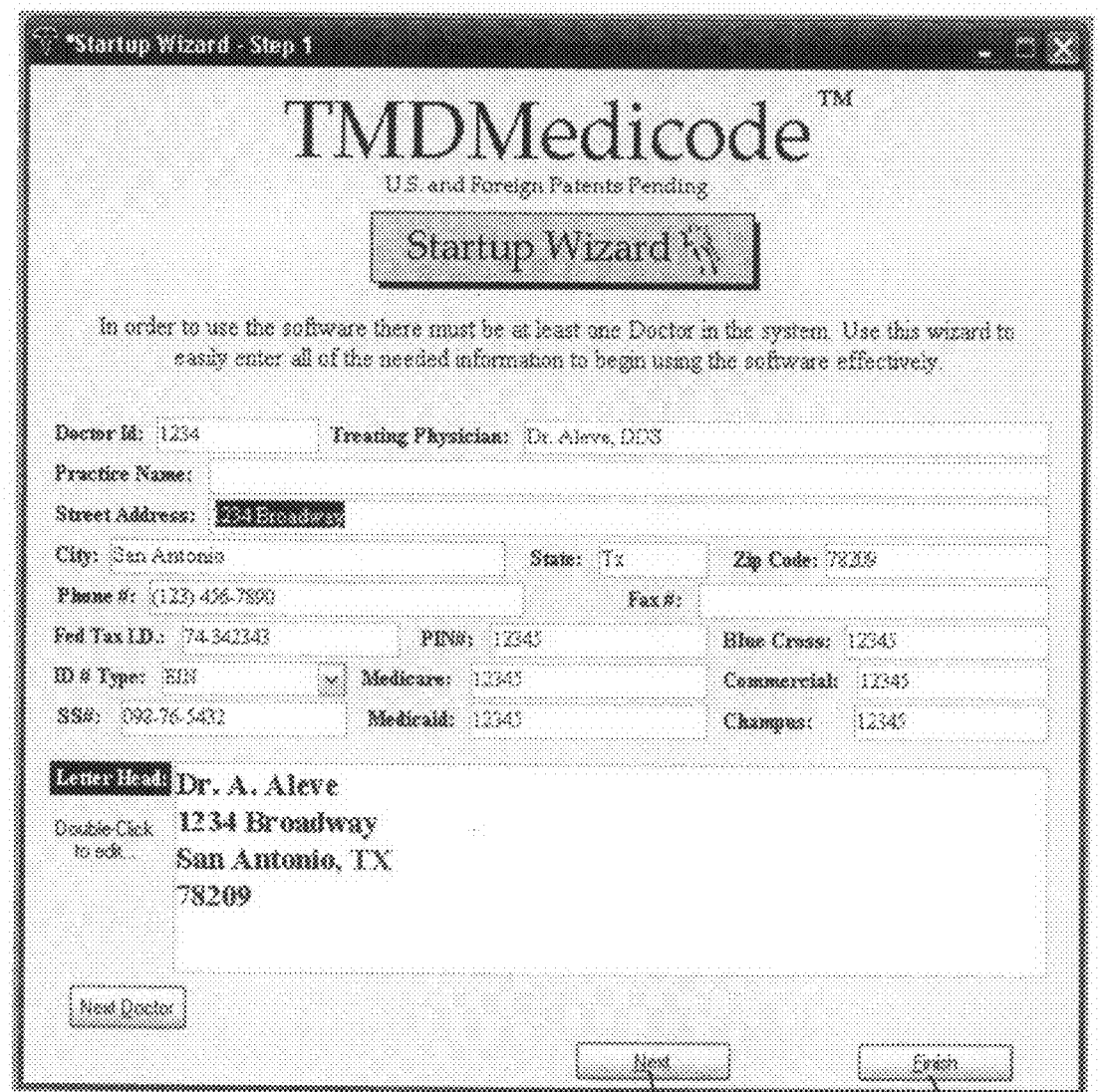
Figure 34B:
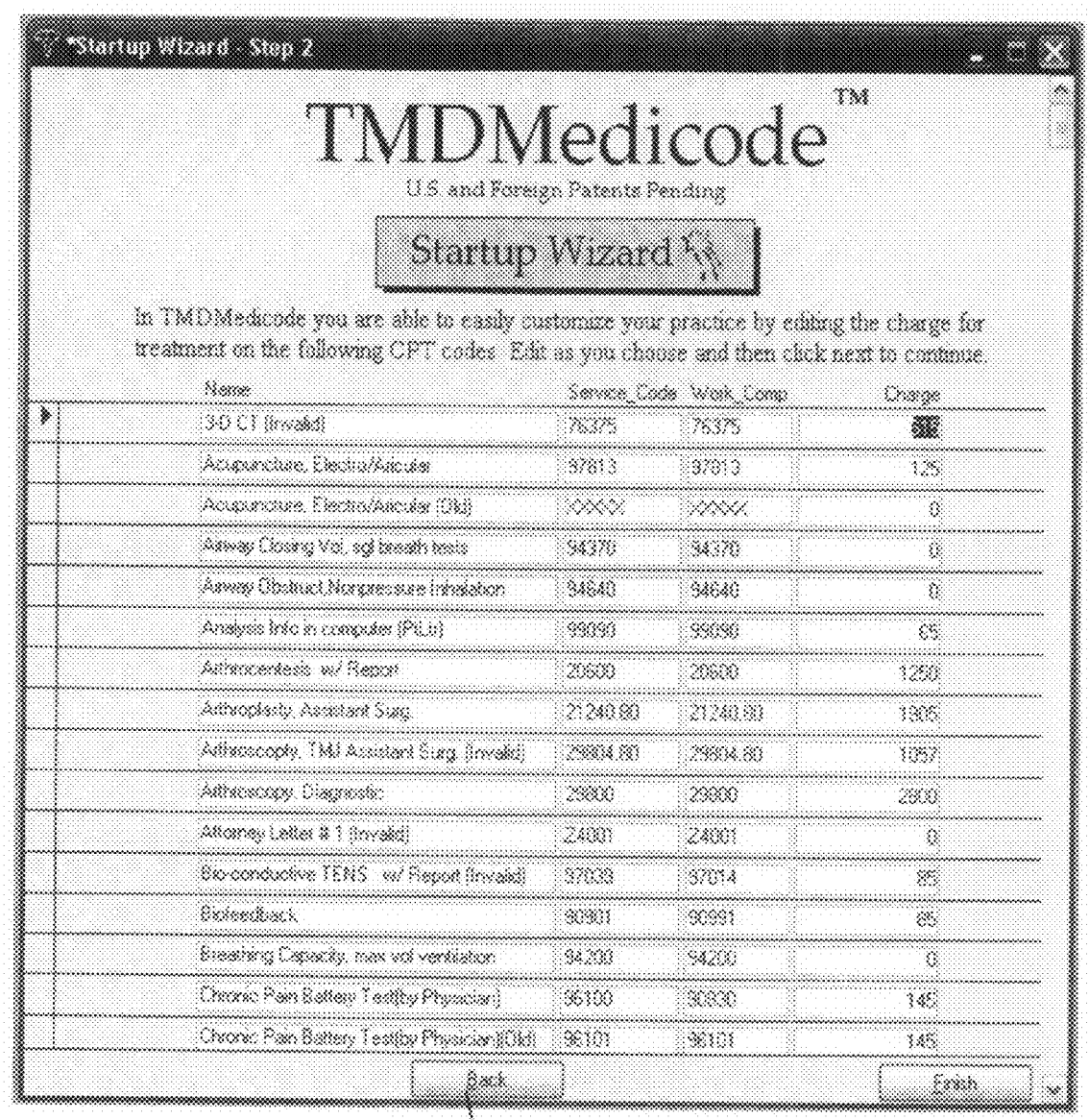
Figure 34C:
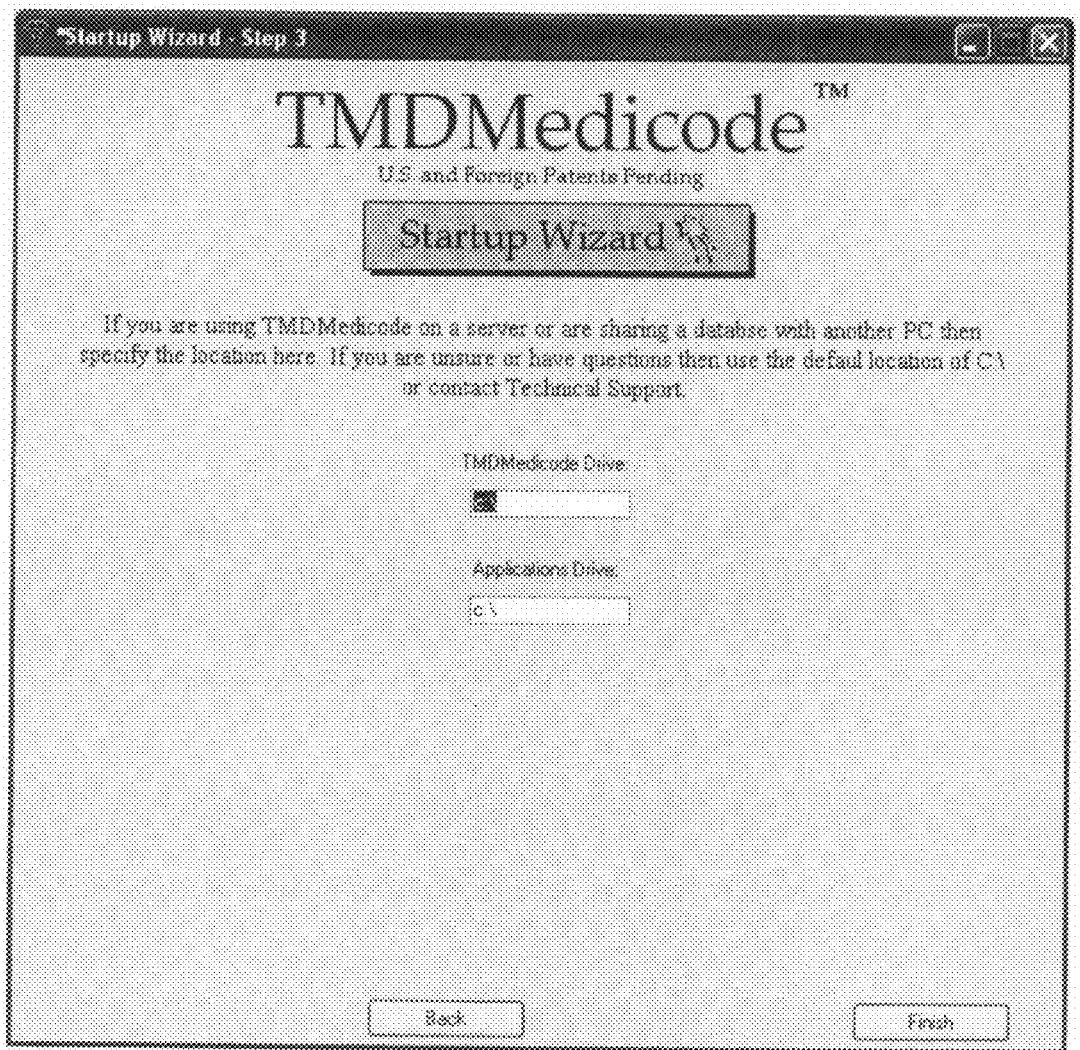

FIG. 2 is a flow diagram showing the various modules and subroutines of the invention and how the user 64 may navigate through system 50. Navigation through the system 50 may be accomplished via a graphical user interface environment of point-and-click icons and menu choices that directly links a user 64 to desired sections. It is understood that selecting, pointing, clicking, choosing, and the like refer to the use of a mouse and mouse pointer, a stylus, a keyboard or any other device for selecting according to the principles of the invention. The system 50 is accessed initially through Startup 72. Startup 72 allows access to Main Menu 76 or System Setup 74. From Menu 76, system 50 permits the user 64 access to Patient Information Module 78, TMD Diagnosis Module 80, TMD Therapy Module 82, Administration Module 84 and Letters and Reports Module 86. All information and data entered into the system 50 from any point updates database 56, 68 for that patient.

Database 56, 68 contain schedules of the ICD 9 codes and CPT codes relating to the medical diagnostics and treatments performed by the Dentist. When the dentist performs a diagnostic or treatment step, the entry into the system of the action performed by the Dentist causes system 50 to record to database 56, 68 that the action took place. System 50 records to database 56, 68 that the action was performed, looks up the corresponding ICD 9 or CPT medical code, looks up the cost of the ICD 9 or CPT code, and records all of this information to the patients file in database 56, 68. When reports are later generated, the action performed and its corresponding ICD 9 or CPT medical code is printed, along with the current cost being charged by the Dentist for that step. Although the action is being performed by a dentist, medical ICD 9 and CPT codes are generated so that the diagnostic and treatment steps taken may be submitted by the Dentist as medical claims rather than dental claims.

It is further understood that modules and subroutines within said modules may link to each other even though FIG. 2 may not show the link. It is also understood that examples of system screens, menus, menu choices and other user interactive screens shown herein are examples of the system 50 user 64 interface, and that the actual interactive screens may differ in appearance due to the differences in software and hardware being used.

FIGS. 1, 3, 4, 5, 6A-6D, 7A-7C, 8, 9A-9C, 10A-10B, 11A-11D, 12A-12C illustrate the sequence of steps and examples of system user interface screens for the First Appointment, which includes initially accessing the system 50, entering new patient information, tests and evaluations to be performed, entering diagnostic results and documenting the information obtained in the First Appointment. The patient is given a date and time for their first appointment (step 101). Either at the Office or in advance, the patient fills out forms regarding basic patient background information, medical history, insurance information and trauma history (step 102). System 50 allows the user 64 to begin by accessing the program, initially bringing up System Entry Screen 176. The user 64 is presented with and may select either Startup Wizard Menu Choice 178, which is described below in the System Setup section, or Enter Menu Choice 177, which brings up Main Menu Screen 191. For The First Appointment, the selection of Patient Information Module Menu Choice 186 accesses the Patient Information Module Screen 192. From Screen 192, the user 64 is permitted by the system 50 to select the Initial Patient Form Entry Menu Choice 193, Health History Menu Choice 194 or Trauma History Menu Choice 195. By selecting Menu Choice 193, the system 50 brings up Patient Information Entry Screen 197 from which initial new patient information can be entered. Selecting Menu Choice 194 or Menu Choice 195 allows the user 64 to access Patient Selection Screen 198. By selecting a patient from the Patient List 199 and selecting the Go To Patient Button 220, the system 50 accesses that patients health and trauma records. Displayed to the user 64 is the Health/Trauma History Screen 221, from which the user 64 can access the patient's health history by selecting the Health History Menu Choice 222 or the Trauma History Menu Choice 223. Selecting Menu Choice 222 accesses the Health Questionnaire Screen 224, from which the user 64 can enter patient health information by accessing various screens which allow for data entry. An example is Health Questionnaire Section One Menu Choice 225 where the first section of the patient's medical and dental history can be entered. Selecting Menu Choice 223 accesses the Trauma Screen 226, from which the user 64 can enter patient health information by accessing various screens which allow for data entry. An example is Patient's Current Problems from Accident Menu Choice 227 where information related to current trauma problems can be entered.

Upon completing the various sections of Screen 224 and Screen 226, the user 64 is permitted to select the Done Menu Button 230. This brings the user 64 back to Screen 221. Selecting "Done" on this page accesses List of New Charges Screen 228. The system 50 allows the user 64 to click the Accept Button 229 to accept the charges, which updates the database 56, 68 regarding the information entered and amounts charged. This system 50 brings the user 64 back to Screen 191.

After entry of the preliminary data into the system 50, the doctor meets with the patient, reviews the previously entered data and begins the Initial Cranio-Mandibular Exam (CME I) (step 104).

From Screen 191, TMD Diagnosis Module Menu Choice 187 is displayed which when selected, takes the user 64 to Diagnostic Module Menu Screen 239. From Screen 239, prior to beginning the examination, the user 64 is permitted by system 50 to select the Existing Patient Information Menu Choice 240, which takes the user 64 to Screen 197 from which previously entered patient information accessed on Screen 197 in step 103 can be modified, if necessary. The system 50 allows the user 64 to begin the examination by selecting Initial CME I Menu Choice 241. From Screen 198, the system 50 displays List 199, from which the user 64 selects the desired patient name from. Selecting Button 220 accesses the CME I Initial Examination Screen 244.

From Screen 244, the Doctor can discuss the patients existing health and trauma history. By selecting the displayed Review Health and Trauma History Menu Choice 245, the system 50 acknowledges and records to the database 56, 68 that this step has been completed (step 104). Also from Screen 244, the Doctor can prescribe range of motion testing (step 105), Doppler Examination (step 106) or prescribe X-ray/CT Scans (step 107). These results are reviewed and entered into the system 50 by selecting ROM-Range of Motion Exam Menu Choice 246 and Doppler Exam Menu Choice 247, which access Mandibular Range of Motion Screen 252 and Doppler Exam Screen 253, respectively, from which the system 50 allows the findings of these exams to be entered. Clicking "Done" at any of these screens causes the system 50 to return the user 64 to Screen 244. By choosing Deliver Soft Orthotic Pain Release Menu Choice 248, the system 50 can update the database 56, 68 to acknowledge and record the fee for orthopanographic imaging. If Dental Screening Menu Choice 249 is selected, the system 50 accesses Dental Screening Screen 271. Selecting the Dental Screening Selection Icon 365 causes the system 50 to bring the user 64 to Screen 198. The user 64 is permitted to select the desired patient name from List 199. Selecting Button 220 accesses Dental Screening Data Entry Screen 272, where findings of the dental examination can be entered. Selecting "Done" from any of the Screen 244 Menu Choices causes the system 50 takes the user 64 back to Screen 244. Selecting "Done" from Screen 244 accesses Screen 228. The user 64 clicks Button 229 to accept the charges, which updates the database 56, 68 regarding the information entered and amounts charged. The system 50 brings the user 64 back to Screen 239.

A radiological report based on the results of the prescribed X-ray/CT scans is prepared by the Doctor (step 108). This report, as well as findings and procedures already entered into the system 50 and stored in database 56, 68 are used to generate documentation by the system 50 supporting the procedures performed by selecting Letters and Reports Menu Choice 243 from Screen 239. This causes the system 50 to access the Letters and Reports Screen 254, from where letters and reports may be produced containing data retrieved from database 56, 68. From Screen 254, additional screens may be accessed from which system 50 can generate documents pertaining to the patient's treatment. By choosing Letters Menu Choice 256 from Screen 254, Letters Screen 258 is displayed by system 50, allowing the user 64 to choose from Justification of Procedures Letters Menu Choice 259 and Customizable Letters Menu Choice 260. Selecting Menu Choice 259 takes the user 64 by system 50 to Justification Letters Screen 261, where the user 64 can choose from a list of various letters justifying the various procedures. Choosing Menu Choice 260 allows system 50 to bring up Print Letters and Reports Screen 262, where a list of standard and customizable letters such as procedure justification letters, attorney letters and insurance letters may be generated by system 50.

From Screen 254, system 50 can generate reports by selecting Reports Menu Choice 257, which accesses the Reports Screen 263. By selecting Report Directory Menu Choice 264, the system 50 brings up Choose Report Screen 267. From here, the user 64 can select from various reports from Report List 268. Various parameters may be specified to customize the report. Selecting Letters and Clinical Findings Menu Choice 265 causes the system 50 to take the user 64 to Screen 262.

The letters and forms that are prepared are preprinted and preformatted documents with information fields which are filled in by system 50. The information placed in the information fields is generated by system 50 through the accessing of data stored in database 56, 68. Upon a request for a document, the system accesses database 56, 68, compiles the necessary data requested by the user for that document (such as indicating that a medical procedure was administered and subsequent findings), performs any mathematical processes (such as adding charges for a total) and places the information in the appropriate field in that document.

All necessary documents to support the claim are printed (step 109). Selecting Invoices and Statements Menu Choice 266 takes the user 64 to Print Invoice Screen 269, where the user 64 can select a patient from Patient List 270 and print account statements. Selecting Update All Patient Charges Menu Choice 255 adds all charges for the procedures done to the patients file in database 56, 68 for billing purposes.

Insurance claim forms with the ICD 9 and CPT medical codes reflecting diagnosis and treatment are generated by system 50, which are submitted to the insurance provider. As explained earlier, medical ICD 9 and CPT codes are used so that although the steps being performed are done by a dentist, the claims may be submitted under the patient's medical insurance for coverage. This process is fully described in the Administration subroutines section detailed below (step 110). The patient is scheduled for the Second Appointment (step 111).

FIGS. 1, 5, 6C, 7C, 8, 9A, 13 and 14 detail the sequence of steps for the Second Appointment. The Doctor meets with the patient and discusses the findings and conclusions of the Initial Cranio-Mandibular Exam (step 112). From Screen 191, the system 50 allows the user 64 to select Menu Choice 187 to go to Screen 239. Selecting Menu Choice 241 causes the system 50 to access Screen 198. The user 64 is permitted to select the desired patient name from List 199. Selecting Button 220 links to Screen 244. By selecting Radiological Evaluation Menu Choice 250, the user 64 is taken to Diagnostic Test and X-Ray Screen 273 by system 50 where the Doctor can review the findings with the patient. Selecting "Done" from Screen 244 accesses Screen 239. Clicking done on Screen 239 brings up Screen 228. The user 64 is allowed to select Button 229 by system 50 to accept the charges, which updates the database 56, 68 regarding the information entered and amounts charged. This user 64 is brought back to Screen 239 by system 50.

Next, the patient meets with an employee of the Office who reviews the patients insurance coverage and informs the patient on costs, coverage, co-payments, deductibles and arrangements for paying the patient's out of pocket expenses (step 113). At the conclusion of the Second Appointment, the patient schedules a date and time for the Third Appointment (step 114).

FIGS. 1, 5, 6A, 7C, 8, 9C, 11A, 14, 15, 16A-16D, 17A-17C, 18A-18D, 19A-19B illustrate the sequence of steps and show examples of system user interface screens for the Third Appointment, which includes accessing the system, tests and evaluations to be performed, entering diagnostic results, prescribing treatment and documenting the information obtained in the Third Appointment.

In the Third Appointment, the patient undergoes the Comprehensive Cranio-Mandibular Exam (CME II) (step 115), which is comprised of a comprehensive battery of tests and the patient being fitted for an orthotic device. System 50 displays Screen 191 to the user 64, from which selecting Menu Choice 187 brings up Screen 239. From Screen 239, the user 64 is permitted to select the Comprehensive Cranio-Mandibular Exam (CME II) Menu Choice 242, which takes the user 64 to Screen 198. The system 50 allows the user 64 to select the desired patient name from List 199. Selecting Button 220 accesses the CME II Comprehensive Examination Screen 274. By selecting Clinical Evaluation Menu Choice 275, the user 64 is taken to a series of screens, beginning with the Summary of Subjective Complaints Screen 280, where subjective complaints can be entered (step 123). Completion of data entry on this Screen brings the user 64 to Screen 253, where the system 50 permits the results of the Doppler examination to be entered (step 201). Following is the Joint Sounds Screen 281, where the system 50 allows joint sound findings to be entered (step 124). Next the system 50 brings up the Neurological Screening Screen 282, where results of the neurological testing are entered (step 125). This is followed by the Myo Testing Screen 283 for entry of Myo testing results (step 126), the Mandibular ROM Screen 284 for Mandibular Range of Motion findings (step 127), the Head and Neck ROM Screen 285 for head and neck range of motion data (step 128), and the Postural Observation Screen 286 for postural observation result entry (step 129). Completion of Screen 286 causes the system 50 to take the user 64 back to Screen 274.

From Screen 274, the system 50 allows the user 64 to choose Radiological Evaluation Menu Choice 276, which will access and allow entry or updating of the data for Screen 273 (step 108).

From Screen 274, the user 64 is permitted by system 50 to choose Sonographic/Joint Vibration Imaging Menu Choice 277, which brings up Sonographic Imaging Screen 287. From Screen 287, the user 64 can select from various menu selections. Selecting Baseline Menu Choice 289 records to database 56, 68 that a pre-diagnostic therapy starting profile of patient's jaw sounds has been performed. Selecting Diagnostic Therapy Followup Menu Choice 290 records to database 56, 68 that post-diagnostic therapy followup imaging of the patients jaw sounds has been performed. The selection of Orthodontic/Orthopedic Followup Menu Choice 291 records to database 56, 68 the performance of an in-progress or post diagnostic therapy joint sounds record. Selecting Surgical Followup Menu Choice 292 records to database 56, 68 that a post-surgical joint sounds record has been made.

The selection of JVA/Sonogram Interpretation Menu Choice 293 causes the system 50 to access Screen 198. By selecting a patient from List 199 and selecting Button 220, New Sono Interpretation Screen 295 is displayed by system 50. By selecting "Yes" from Screen 295, the user 64 is taken to Digital Sonogram and Frequency Interpretation/Interpretation of Joint Vibration Analysis Screen 296, where sonogram and joint vibration analysis data can be entered.

The selection of IME/IMR Medical Evaluation Menu Choice 294 accesses Screen 198 by system 50. By selecting a patient from List 199 and selecting Button 220, New Medical Necessity Report Screen 297 is displayed by system 50. By selecting "Yes" from Screen 297, the user 64 is taken to Medical Necessity Screen 298, where data relating to the medical necessity of procedures can be entered.

Selecting "Done" on any of the menu choices on Screen 287 returns the user 64 by system 50 to Screen 287. Selecting "Done" on Screen 287 returns the user 64 to Screen 274.

Upon completion of the other subroutines accessed from the menu choices on the Screen 274, the user 64 is permitted by system 50 to select Diagnostic Impressions Menu Choice 278 in order to access Diagnostic Impressions Screen 288, where the user 64 can select various diagnostic findings (step 130). Selecting "Done" from Screen 274 accesses Screen 228. Clicking Button 229 causes system 50 to accept the charges, which updates database 56, 68 regarding the information entered and amounts charged. The system 50 brings the user 64 back to Screen 239.

Following the diagnostic findings (step 130) an orthotic device is prepared by taking maxillary and mandibular impressions (step 116), occlusal registration (step 117) and face bow record (step 118). A prescription for the orthotic is prepared from the measurements and is sent to a laboratory for creation of the device (step 119), followed by the receipt of the device when completed (step 120).

The Fourth Appointment is scheduled (step 121). From Screen 274, system 50 permits the selection of Letters and Reports Menu Choice 279, taking the user 64 to Screen 254. The process for generating and printing relevant documents and reports containing information retrieved from database 56, 68 (step 122) is fully described in step 109 above.

Insurance claim forms with the ICD 9 and CPT medical codes reflecting diagnosis and treatment are generated by system 50, which are submitted to the insurance provider (step 131). As explained earlier, medical ICD 9 and CPT codes are used so that although the steps being performed are done by a dentist, the claims may be submitted under the patient's medical insurance for coverage. This process is fully described in the Administration subroutines section detailed below.

Figure 11D:
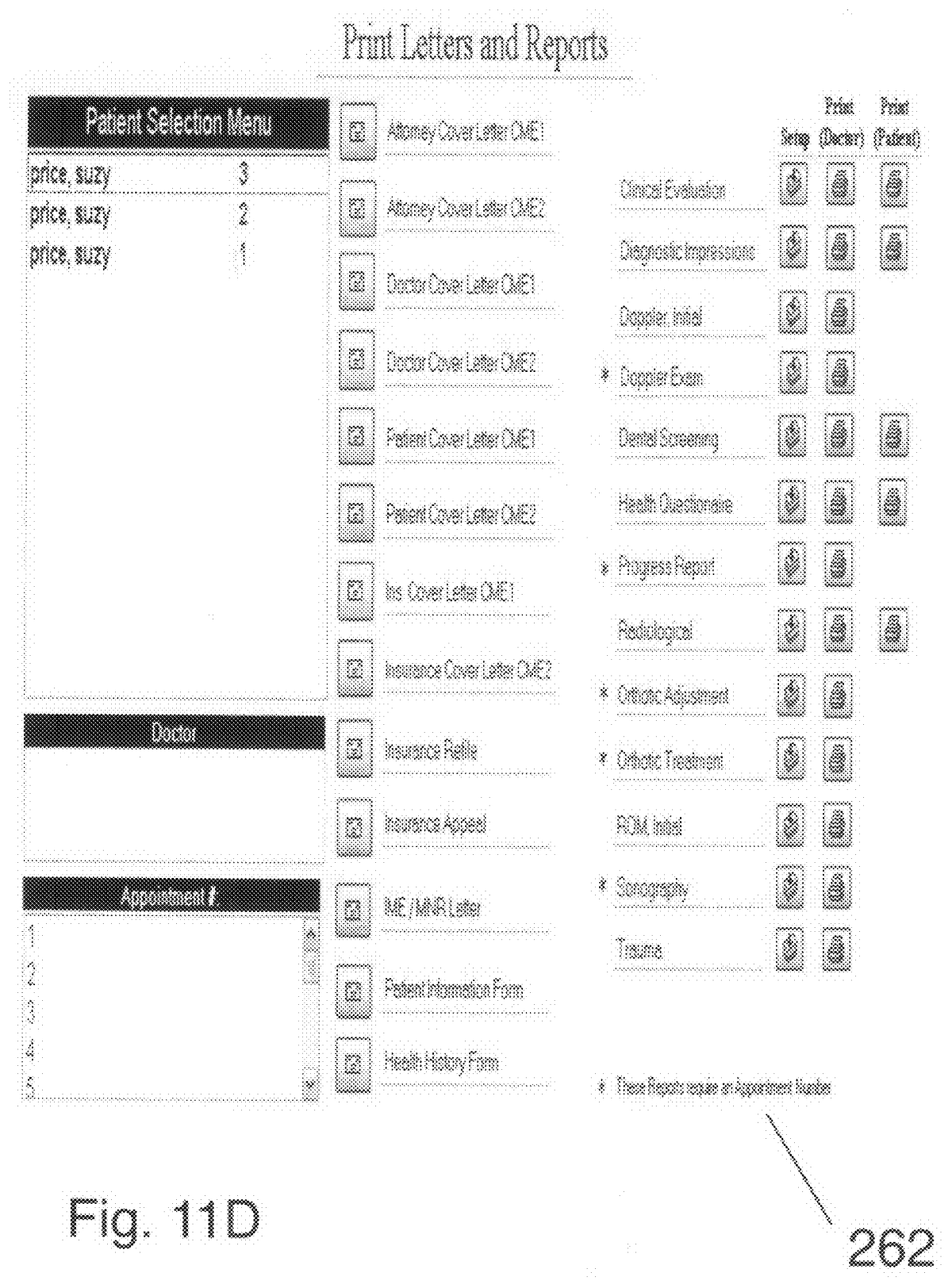

FIGS. 1, 5, 6B-6C, 8, 11A 20, 21A-21D, 22A-22D, 23A illustrate the sequence of steps and shows examples of system user interface screens for the Fourth Appointment, which involves fitting the orthotic device, beginning orthotic therapy, tests and evaluations, entering diagnostic results, prescribing treatment and documenting the information obtained in the Fourth Appointment. The user 64 is permitted by system 50 to access Screen 191 and select the TMD Treatment Therapy Module Menu Choice 188 (alternatively, the user 64 can choose Menu Choice 242 from Screen 239). System 50 takes the user 64 to Diagnostic Therapy Module Screen 300. From this screen, the user 64 can select the Existing Patient Information Menu Choice 301, which takes the user 64 to Screen 197 from which previously entered patient information can be modified, if necessary. To begin orthotic therapy (step 132), the selecting of Orthotic Therapy Menu Choice 302 from Screen 300 accesses Screen 198 by system 50. From Screen 198, the user 64 is permitted by system 50 to select the desired patient name from List 199. Selecting Button 220 brings up Diagnostic Orthotic Therapy Screen 304. The Doctor fits and adjusts the orthotic device to the patient. The user 64 selects Seat Orthotic Menu Choice 305, which accesses Orthotic Adjustment Screen 312, where adjustments to the orthotic device are recorded (step 133).

When done with this menu choice and the remaining menu choices of Screen 304, the user 64 is returned by system 50 to Screen 304.

Selecting Orthotic Evaluation Menu Choice 306 accesses Orthotic Evaluation Screen 313, where entry of data relating to the functionality of the orthotic device is performed (step 134). Selecting Orthotic Adjustment Menu Choice 307 brings the user 64 to Orthotic Adjustment Screen 314, where adjustments to the orthotic device are recorded (step 208). Selecting ROM Evaluation Menu Choice 308 takes the user 64 to ROM Evaluation Screen 315, where range of motion test results can be entered (step 135). Selecting Myo Testing Menu Choice 309 accesses Myo Testing Screen 316, where data entry for muscle testing can be entered by the user 64 (step 136). Doppler Menu Choice 320 links to Doppler Examination Screen 317, where the findings of Doppler auscultation testing can be recorded (step 202). Selecting Doctor Prescription Menu Choice 310 allows the user 64 to enter various prescription drugs and therapies into the system 50 through Doctor Prescriptions Screen 318 (step 137). When the user 64 selects Done, they are returned to Screen 300. From Screen 300, Letters and Reports Menu Choice 303 can be selected, taking the user 64 to Screen 254. All entries are recorded by system 50 to database 56, 68. The process for generating and printing relevant documents and reports containing information retrieved from database 56, 68 (step 138) is fully described in step 109 above.

Insurance claim forms with the ICD 9 and CPT medical codes reflecting diagnosis and treatment are generated, which are submitted to the insurance provider (step 139). As explained earlier, medical ICD 9 and CPT codes are used so that although the steps being performed are done by a dentist, the claims may be submitted under the patient's medical insurance for coverage. This process is fully described in the Administration subroutines section detailed below.

FIGS. 1, 5, 6B, 8, 11A, 21A, 21B, 21D, 22A-22D, 23A, 24 illustrate the sequence of steps and examples of system user interface screens for the Fifth through Eighth Appointments, which involves continuing orthotic therapy, tests and evaluations, entering diagnostic results, prescribing treatment and documenting the information obtained in the Fifth through Eighth Appointments. System 50 permits the user 64 to enter this information by accessing Screen 191 and allowing user 64 to select the Menu Choice 188 (alternatively, the user 64 can choose Menu Choice 242 from Screen 239). System 50 allows the user 64 to view Screen 300. From this screen, the user 64 can select the Menu Choice 301, which takes the user 64 to Screen 197 from which previously entered patient information can be modified, if necessary. To continue orthotic therapy (step 140), the user 64 is permitted to select Menu Choice 302 from Screen 300, bringing up Screen 304. Selecting Menu Choice 306 accesses Screen 313, where entry of data relating to the functionality of the orthotic device is performed (step 141). Selecting Menu Choice 307 brings the user 64 to Screen 314, where adjustments to the orthotic device are recorded (step 209), either as a direct seat where the orthotic device is fitted directly in the patients mouth, or an indirect seat, where the device is fitted to a model and then placed in the patient's mouth. This is recorded by selecting "direct" or "indirect" in Selection Box 321. Selecting Menu Choice 308 takes the user 64 to Screen 315, where range of motion test results can be entered (step 142). Selecting Menu Choice 309 accesses Screen 316, where data entry for muscle testing can be entered by the user 64 (step 143). Doppler Menu Choice 320 links to Screen 317, where the findings of Doppler auscultation testing can be recorded (step 203). Selecting Menu Choice 310 allows the user 64 to enter various prescription drugs and therapies into system 50 through Screen 318 (step 144). System 50 allows the user 64 to select "Done" and is returned to Screen 300. All entries are recorded to database 56, 68 by system 50. From Screen 300, Menu Choice 303 can be selected, taking the user 64 Screen 254. The process for generating and printing relevant documents and reports containing information retrieved from database 56, 68 (step 145) is fully described in step 109 above.

Insurance claim forms with the ICD 9 and CPT medical codes reflecting diagnosis and treatment are generated by system 50, which are submitted to the insurance provider (step 146). As explained earlier, medical ICD 9 and CPT codes are used so that although the steps being performed are done by a dentist, the claims may be submitted under the patient's medical insurance for coverage. This process is fully described in the Administration subroutines section detailed below.

FIGS. 1, 5, 6B, 8, 11A, 21A, 21B, 21D, 22A-22D, 23A-23B, 25 illustrate the sequence of steps and examples of system user interface screens for the Ninth Appointment, which involves continuing orthotic therapy, tests and evaluations, entering diagnostic results, prescribing treatment and documenting the information obtained in the Ninth Appointment. System 50 permits the user 64 to enter this information into the system 50 by accessing Screen 191 and selecting the Menu Choice 188 (alternatively, the user 64 can choose Menu Choice 242 from Screen 239). This takes the user 64 to Screen 300. From this screen, the user 64 is permitted to select the Menu Choice 301, which takes the user 64 to Screen 197 from which previously entered patient information can be modified, if necessary. To continue orthotic therapy (step 147), the user 64 selects Menu Choice 302 from Screen 300, bringing up Screen 304. Selecting Menu Choice 306 accesses Screen 313, where entry of data relating to the functionality of the orthotic device is performed (step 148). Selecting Menu Choice 307 brings the user 64 to Screen 314, where adjustments to the orthotic device are recorded (step 210). Selecting Menu Choice 308 takes the user 64 to Screen 315, where range of motion test results can be entered (step 149). Selecting Menu Choice 309 accesses Screen 316, where data entry for muscle testing can be entered by the user 64 (step 150). Doppler Menu Choice 320 links to Screen 317, where the findings of Doppler auscultation testing can be recorded (step 204). Selecting Menu Choice 310 allows the user 64 to enter various prescription drugs and therapies into system 50 through Screen 318 (step 151). Selecting Progress Report Menu Choice 311 accesses Progress Report Screen 319, where the Doctor can enter findings that detail the progress of the therapy and treatment (step 152). System 50 allows the user 64 to select "Done" and is returned to Screen 300. All entries are recorded to database 56, 68 by system 50. From Screen 300, Letters and Reports Menu Choice 303 can be selected, taking the user 64 to Screen 254. The process for generating and printing relevant documents and reports containing information retrieved from database 56, 68 (step 153) is fully described in step 109 above.

Insurance claim forms with the ICD 9 and CPT medical codes reflecting diagnosis and treatment are generated by system 50, which are submitted to the insurance provider (step 154). As explained earlier, medical ICD 9 and CPT codes are used so that although the steps being performed are done by a dentist, the claims may be submitted under the patient's medical insurance for coverage. This process is fully described in the Administration subroutines section detailed below.

FIGS. 1, 5, 6B, 8, 11A, 21A, 21B, 21D, 22A-22D, 23A, 26 illustrate the sequence of steps and examples of system user interface screens for the Tenth through Thirteenth Appointments, which involves continuing orthotic therapy, tests and evaluations, entering diagnostic results, prescribing treatment and documenting the information obtained in the Tenth through Thirteenth Appointments. System 50 permits the user 64 to enter this information into system 50 by accessing Screen 191 and selecting Menu Choice 188 (alternatively, the user 64 can choose Menu Choice 242 from Screen 239). This takes the user 64 to Screen 300. From this screen, the user 64 can select the Menu Choice 301, which takes the user 64 to Screen 197 from which previously entered patient information can be modified, if necessary. To continue orthotic therapy (step 155), the user 64 is permitted to select Menu Choice 302 from Screen 300, bringing up Screen 304. Selecting Menu Choice 306 accesses Screen 313, where entry of data relating to the functionality of the orthotic device is performed (step 156). Selecting Menu Choice 307 brings the user 64 to Screen 314, where adjustments to the orthotic device are recorded (step 211). Selecting Menu Choice 308 takes the user 64 to Screen 315, where range of motion test results can be entered (step 157). Selecting Menu Choice 309 accesses Screen 316, where data entry for muscle testing can be entered by the user 64 (step 158). Selecting Menu Choice 310 allows the user 64 to enter various prescription drugs and therapies into system 50 through Screen 318 (step 159). Doppler Menu Choice 320 links to Screen 253, where the findings of Doppler auscultation testing can be recorded (step 205). System 50 allows the user 64 to select "Done" and is returned to Screen 300. All entries are recorded to database 56, 68 by system 50. From Screen 300, Menu Choice 303 can be selected, taking the user 64 to Screen 254. The process for generating and printing relevant documents and reports containing information retrieved from database 56, 68 (step 160) is fully described in step 109 above.

Insurance claim forms with the ICD 9 and CPT medical codes reflecting diagnosis and treatment are generated by system 50, which are submitted to the insurance provider (step 161). As explained earlier, medical ICD 9 and CPT codes are used so that although the steps being performed are done by a dentist, the claims may be submitted under the patient's medical insurance for coverage. This process is fully described in the Administration subroutines section detailed below.

FIGS. 1, 5, 6B, 8, 11A, 21A, 21B, 21D, 22A-22D, 23A-23B, 27 illustrate the sequence of steps and examples of system user interface screens for Appointment 14, which involves continuing orthotic therapy, tests and evaluations, entering diagnostic results, prescribing treatment and documenting the information obtained in the Appointment 14. System 50 permits the user 64 to enter this information by accessing Screen 191 and selecting the Menu Choice 188 (alternatively, the user 64 can choose Menu Choice 242 from Screen 239). This takes the user 64 to Screen 300. From this screen, the user 64 can select the Menu Choice 301, which takes the user 64 to Screen 197 from which previously entered patient information can be modified, if necessary. To continue orthotic therapy (step 162), the user 64 is permitted to select Menu Choice 302 from Screen 300, bringing up Screen 304. Selecting Menu Choice 306 accesses Screen 313, where entry of data relating to the functionality of the orthotic device is performed (step 163). Selecting Menu Choice 307 brings the user 64 to Screen 314, where adjustments to the orthotic device are recorded (step 212). Selecting Menu Choice 308 takes the user 64 to Screen 315, where range of motion test results can be entered (step 164). Selecting Menu Choice 309 accesses Screen 316, where data entry for muscle testing can be entered by the user 64 (step 165). Doppler Menu Choice 320 links to Screen 317, where the findings of Doppler auscultation testing can be recorded (step 206). Selecting Menu Choice 310 allows the user 64 to enter various prescription drugs and therapies into system 50 through Screen 318 (step 166). Selecting Menu Choice 311 accesses Screen 319, where the Doctor can enter findings that detail the progress of the therapy and treatment (step 167). System 50 allows the user 64 to select "Done" and is returned to Diagnostic Screen 300. All entries are recorded to database 56, 68 by system 50. From Screen 300, Menu Choice 303 can be selected, taking the user 64 to Screen 254. The process for generating and printing relevant documents and reports containing information retrieved from database 56, 68 (step 168) is fully described in step 109 above.

Insurance claim forms with the ICD 9 and CPT medical codes reflecting diagnosis and treatment are generated by system 50, which are submitted to the insurance provider (step 169). As explained earlier, medical ICD 9 and CPT codes are used so that although the steps being performed are done by a dentist, the claims may be submitted under the patient's medical insurance for coverage. This process is fully described in the Administration subroutines section detailed below.

FIGS. 1, 5, 6B, 8, 11A, 21A, 21B, 21D, 22A-22D, 23A, 28 illustrate the sequence of steps and examples of system user interface screens for the Fifteenth Appointment and beyond, which involves continuing orthotic therapy, tests and evaluations, entering diagnostic results, prescribing treatment and documenting the information obtained in the Fifteenth Appointment and beyond. System 50 permits the user 64 to this information into the system 50 by accessing Screen 191 and selecting the Menu Choice 188 (alternatively, the user 64 can choose Menu Choice 242 from Screen 239). This takes the user 64 to Screen 300. From this screen, the user 64 can select the Menu Choice 301, which takes the user 64 to Screen 197 from which previously entered patient information can be modified, if necessary. To continue orthotic therapy (step 170), the user 64 is permitted to select Menu Choice 302 from Screen 300, bringing up Screen 304. Selecting Menu Choice 306 accesses Screen 313, where entry of data relating to the functionality of the orthotic device is performed (step 171). Selecting Menu Choice 307 brings the user 64 to Screen 314, where adjustments to the orthotic device are recorded (step 213). Selecting Menu Choice 308 takes the user 64 to Screen 315, where range of motion test results can be entered (step 172). Selecting Menu Choice 309 accesses Screen 316, where data entry for muscle testing can be entered by the user 64 (step 173). Doppler Menu Choice 320 links to Screen 317, where the findings of Doppler auscultation testing can be recorded (step 207). Selecting Menu Choice 310 allows the user 64 to enter various prescription drugs and therapies into system 50 through Screen 318 (step 174). The user 64 selects "Done" and is returned to Screen Module 300. All entries are recorded to database 56, 68 by system 50. From Screen 300, Menu Choice 303 can be selected, taking the user 64 to Screen 254. The process for generating and printing relevant documents and reports containing information retrieved from database 56, 68 (step 160) is fully described in step 109 above.

Insurance claim forms with the ICD 9 and CPT medical codes reflecting diagnosis and treatment are generated by system 50, which are submitted to the insurance provider (step 176). As explained earlier, medical ICD 9 and CPT codes are used so that although the steps being performed are done by a dentist, the claims may be submitted under the patient's medical insurance for coverage. This process is fully described in the Administration subroutines section detailed below.

FIGS. 1, 4-5, 29, 30A-30D, 31A-31C, 32A-32D, 33, 34A-34C illustrate the sequence of steps and system user interface screens within the System Setup and Administrative subroutines.

From Screen 191, system 50 allows the user 64 to select Administration Menu Choice 189, which links to Administration Screen 330. For any of the Menu Choices, selecting "Done" will cause system 50 to take the user 64 back to Screen 330. Selecting Add New Patient Menu Choice 331 accesses Patient Information Screen 345, where new patient information can be added or existing patient information can be modified, as in step 103. Selecting Add/Edit Insurance and Attorney Contact Information Menu Choice 332 brings up Contact Info Screen 346, where attorney and insurance company information can be added or modified. Selecting Add Memos/Notes Menu Choice 333 allows the user 64 to view Insurance Information Screen 347, where insurance company information such as group numbers and claim numbers can be entered. Choosing Add/Edit ICD 9 Codes Menu Choice 334 brings up Doctor Information Screen 348, where ICD 9 diagnosis codes can be manually added or edited. The Add/Edit Doctor Information Menu Choice 335 accesses the Providers Screen 349, where additional Doctors providing services using the system 50 can be added or existing Doctor information can be modified. Selecting Edit CPT Fees Menu Choice 336 brings up the Chargeable Services Screen 350, where the fees charged for services can be changed based on its CPT code. Selecting Record Payments Menu Choice 337 links to Paid Invoices Screen 351, where the user 64 can enter amounts paid by the patient or the patient's insurance company. Selecting Add Charges Menu Choice 338 causes the system 50 to update all current charges not already entered into the database 56, 68, bringing accounts current for all services provided. Selecting the Print Insurance Menu Choice 339 accesses the Insurance Screen 360, which contains the Setup Insurance-Add Charges Menu Choice 361 and Print Insurance Forms Menu Choice 362. Selecting Setup Insurance-Add Charges Menu Choice 361 takes the user 64 to Insurance Information Screen 363, where information relating to the insurance provider can be entered or amended. Selecting Done from Screen 363 take the user 64 to Insurance Setup Finish Screen 364, where the user 64 acknowledges completion of the entry of the insurance information, which returns the user 64 to Screen 360 All entries are recorded to database 56, 68 by system 50.

Selecting Menu Choice 362 allows the user 64 to access Print Insurance Screen 365. From Patient List 366, the user 64 can select a patient and display Insurance Form Display Screen 367. From here, the user 64 may print medical health insurance forms with ICD 9 diagnosis codes and CPT treatment codes that have been automatically entered based on services performed by the Doctor and entered into the system 50. Selecting "Done" takes the user 64 back to Screen 360.

From Screen 176, the user 64 is permitted by system 50 to select either Menu Choice 177 or Menu Choice 178. By selecting Menu Choice 178, the user 64 is taken to Startup Wizard Screen 179, where system 50 configuration may be performed. From Screen 179, the user may add the names and information for Doctors providing services using the system 50. From Screen 179 and subsequent screens accessed from Menu Choice 178, the user 64 can continue forward to the next user interface screen by selecting Menu Choice Next 181, go back to the previous user interface screen by selecting Menu Choice Back 182 or exit back to Screen 176 by selecting Menu Choice Finish 183. Selecting Menu Choice 181 from Screen 179 takes the user 64 to CPT Code Screen 184, where the user 64 can customize CPT treatment codes.

Selecting Menu Choice 181 on Screen 184 takes the user 64 to Location Configuration Screen 185, where the user 64 can set the location of the server and the application. By selecting Menu Choice 183, the user 64 is taken to Screen 191. All entries from this subroutine are recorded to database 56, 68 by system 50.

The invention can be practiced with additional steps for processing or paying insurance claims or for communicating the status of submitted claims to health care providers and patients by system 50. For instance, when a claim has been submitted and approved, an explanation of benefits can be automatically created and sent to the provider, the patient, and/or to an employer of the patient. Electronic funds transfer can be used to execute payment from insurers to health care providers for approved claims by system 50.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. Although the present invention has been described in terms of the foregoing preferred embodiments, such description has been for exemplary purposes only and, as will be apparent to those of ordinary skill in the art, many alternatives, equivalents, and variations of varying degrees will fall within the scope of the present invention. That scope, accordingly, is not to be limited in any respect by the foregoing detailed description; rather, it is defined only by the claims that follow.

I claim:

1. A method of examining, diagnosing, treating, and generating documentation for temporomandibular joint disorders in dental patients, comprising:
   (a) evaluating a dental patient during a first appointment, wherein the evaluation includes performing at least a Doppler examination;
   (b) storing and processing patient information, evaluation results, and treatments within a computer system;
   (c) generating documentation after the first appointment regarding the patient's temporomandibular joint disorder, wherein the documentation includes insurance claim forms for submission to the patient's medical insurance provider and to the patient's dental insurance provider;
   (d) establishing an examination and treatment protocol for the patient's temporomandibular joint disorder, wherein the protocol comprises a sequence of examinations and treatments for the temporomandibular joint disorder that conform to medical insurance industry standards to maximize benefit payments by insurance providers;
   (g) generating documentation after the second appointment regarding the patient's temporomandibular joint disorder, wherein said documentation includes insurance claim forms for submission to the patient's insurance provider;
   (i) generating documentation after each appointment regarding the patient's temporomandibular joint disorder, wherein said documentation includes insurance claim forms for submission to the patient's insurance provider.

2. The method of claim 1, wherein the storing and processing of patient information, evaluation results and treatments within a computer system includes:
   (a) providing an input means for entering and creating new data items in a database stored within a memory storage device accessible by a central processing unit;
   (b) providing an input means to enter and store patient information, evaluation results and treatments into said database; and
   (c) a data item mapping means for associating inputted patient information, evaluation results and treatments stored in said database with at least one data item definition in said database to generate and populate field entries in documents.

3. The method of claim 2, wherein the documents generated are medical insurance claim forms containing fields populated with standard insurance industry medical codes for diagnosis and treatments.

4. The method of claim 3, wherein the documents generated are support documents, including but not limited to letters and forms.

5. The method of claim 3, wherein the standard insurance industry medical codes are ICD-9 medical insurance codes for diagnosis and CPT medical insurance codes for treatments.

6. The method of claim 5, wherein the documents generated are support documents, including but not limited to letters and forms.

7. The method of claim 2, wherein the documents generated are dental insurance claims forms.

8. The method of claim 7, wherein the documents generated are support documents, including but not limited to letters and forms.

9. A computer program embodied on a computer system readable medium for examining, diagnosing, treating, and generating documentation for temporomandibular joint disorders in dental patients comprising: (a) instructions for evaluating a dental patient during a first appointment, wherein the evaluation includes performing at least a Doppler examination; (b) instructions for storing and processing patient information, evaluation results, and treatments within a computer system; and
   (c) instructions for generating documentation after the first appointment regarding the patient's temporomandibular joint disorder, wherein the documentation includes insurance claim forms for submission to the patient's medical insurance provider and to the patient's dental insurance provider;
   (d) instructions for establishing an examination and treatment protocol for the patient's temporomandibular joint disorder, wherein the protocol comprises a sequence of examinations and treatments for the temporomandibular joint disorder that conform to medical insurance industry standards to maximize benefit payments by insurance providers;
   (g) instructions for generating documentation after the second appointment regarding the patient's temporomandibular joint disorder, wherein said documentation includes insurance claim forms for submission to the patient's insurance provider;
   (i) instructions for generating documentation after each appointment regarding the patient's temporomandibular joint disorder, wherein said documentation includes insurance claim forms for submission to the patient's insurance provider.

10. The computer program of claim 9, wherein the instructions for storing and processing patient information, evaluation results and treatments within a computer system includes:

(a) instructions for providing an input means for entering and creating new data items in a database stored within a memory storage device accessible by a central processing unit;

(b) instructions for providing an input means to enter and store patient information, evaluation results and treatments into said database; and (c) instructions for providing a data item mapping means for associating inputted patient information, evaluation results and treatments stored in said database with at least one data item definition in said database to generate and populate field entries in documents.

11. The computer program of claim 10, wherein the computer program further includes instructions for generating documents consisting of medical insurance claim forms containing fields populated with standard insurance industry medical codes for diagnosis and treatments.

12. The computer program of claim 11, wherein the computer program further includes instructions for generating documents, wherein the generated documents are support documents, including but not limited to forms and letters.

13. The computer program of claim 11, wherein the computer program further includes instructions to populate the medical insurance claim form fields containing standard insurance industry medical codes with ICD-9 medical insurance codes for diagnosis and CPT medical insurance codes for treatments.

14. The computer program of claim 13, wherein the computer program further includes instructions for generating documents, wherein the generated documents are support documents, including but not limited to forms and letters.

15. The computer program of claim 10, wherein the computer program further includes instructions for generating documentation, consisting of dental insurance claims forms.

16. The computer program of claim 15, wherein the computer program further includes instructions for generating documents, wherein the generated documents are support documents, including but not limited to forms and letters.

* * * * *